(12) United States Patent
Schwink et al.

(10) Patent No.: US 8,853,412 B2
(45) Date of Patent: Oct. 7, 2014

(54) PYRROLIDINONE DERIVATIVES AS GPR119 MODULATORS FOR THE TREATMENT OF DIABETES, OBESITY, DYSLIPIDEMIA AND RELATED DISORDERS

(71) Applicants: Lothar Schwink, Frankfurt am Main (DE); Martin Bossart, Frankfurt am Main (DE); Heiner Glombik, Frankfurt am Main (DE); Matthias Gossel, Frankfurt am Main (DE); Dieter Kadereit, Frankfurt am Main (DE); Thomas Klabunde, Frankfurt am Main (DE); Thomas Maier, Frankfurt am Main (DE); Siegfried Stengelin, Frankfurt am Main (DE)

(72) Inventors: Lothar Schwink, Frankfurt am Main (DE); Martin Bossart, Frankfurt am Main (DE); Heiner Glombik, Frankfurt am Main (DE); Matthias Gossel, Frankfurt am Main (DE); Dieter Kadereit, Frankfurt am Main (DE); Thomas Klabunde, Frankfurt am Main (DE); Thomas Maier, Frankfurt am Main (DE); Siegfried Stengelin, Frankfurt am Main (DE)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 14/048,425

(22) Filed: Oct. 8, 2013

(65) Prior Publication Data
US 2014/0099333 A1 Apr. 10, 2014

(30) Foreign Application Priority Data
Oct. 9, 2012 (EP) .................................... 12306231

(51) Int. Cl.
*C07D 401/00* (2006.01)
*A61K 31/44* (2006.01)
*A61K 31/497* (2006.01)
*C07D 401/12* (2006.01)
*A61K 31/4545* (2006.01)
*C07D 413/14* (2006.01)
*A61K 31/4439* (2006.01)
*C07D 401/14* (2006.01)
*C07D 407/14* (2006.01)
*C07D 417/14* (2006.01)
*C07D 207/12* (2006.01)
*C07D 405/14* (2006.01)
*A61K 31/444* (2006.01)
*A61K 31/4015* (2006.01)

(52) U.S. Cl.
CPC ............ *A61K 31/497* (2013.01); *C07D 401/12* (2013.01); *A61K 31/4545* (2013.01); *C07D 413/14* (2013.01); *A61K 31/4439* (2013.01); *C07D 401/14* (2013.01); *C07D 407/14* (2013.01); *C07D 417/14* (2013.01); *C07D 207/12* (2013.01); *A61K 46/06* (2013.01); *C07D 405/14* (2013.01); *A61K 31/444* (2013.01); *A61K 31/4015* (2013.01)
USPC ........................................ 546/278.4; 514/340

(58) Field of Classification Search
None
See application file for complete search history.

(56) References Cited

FOREIGN PATENT DOCUMENTS

| EP | 1 795 524 A1 | 6/2007 |
|---|---|---|
| WO | WO 2004/110994 A1 | 12/2004 |
| WO | WO 2010/048149 A2 | 4/2010 |
| WO | WO 2011/146335 A1 | 11/2011 |
| WO | WO 2012/037393 A1 | 3/2012 |
| WO | WO 2013/070463 A2 | 5/2013 |

*Primary Examiner* — Heidi Reese
(74) *Attorney, Agent, or Firm* — Scully, Scott, Murphy & Presser, P.C.

(57) ABSTRACT

The present invention relates to pyrrolidinone derivatives. The pyrrolidinone derivatives are GPR119 modulators and useful for the prevention and/or treatment of diabetes, obesity, dyslipidemia and related disorders. The invention furthermore relates to the use of pyrrolidinone derivatives as active ingredients in pharmaceuticals, and pharmaceutical compositions comprising them.

31 Claims, No Drawings

PYRROLIDINONE DERIVATIVES AS GPR119 MODULATORS FOR THE TREATMENT OF DIABETES, OBESITY, DYSLIPIDEMIA AND RELATED DISORDERS

The present invention relates to pyrrolidinone derivatives of the formula I

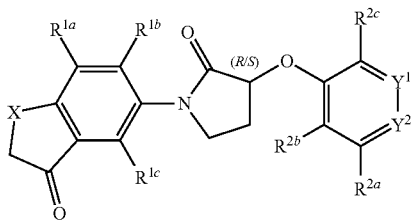

in which $R^{1a}$, $R^{1b}$, $R^{1c}$, $R^{2a}$, $R^{2b}$, $R^{2c}$, X, $Y^1$ and $Y^2$ are defined as indicated below. The pyrrolidinone derivatives I are GPR119 modulators and useful for the prevention and/or treatment of diabetes, obesity, dyslipidemia and related disorders. The invention furthermore relates to the use of pyrrolidinone derivatives of the formula I as active ingredients in pharmaceuticals, and pharmaceutical compositions comprising them.

GPR119 is a G-protein coupled receptor which is expressed predominantly in the beta cells of the pancreas and in the K- and L-cells of the intestine. In vitro studies have shown, that agonists of GPR119, via activation of the cAMP pathway in gut and pancreas derived cell lines, mediate the secretion of GLP-1 and insulin respectively. This supports the hypothesis, that modulators of GPR119, agonists in particular, may have utility to treat diabetes and related disorders by augmenting the secretion of insulin and intestinal hormones like GIP, GLP-1 and PYY. As the secretion of insulin was found to be strictly glucose-dependent, induction of hypoglycemic episodes may largely be avoided. Furthermore beneficial effects like reduced food intake may be expected from the release of intestinal peptides. Stimulation of the beta cell by activation of GPR119 may also improve beta cell function and beta cell mass. Studies of GPR119 agonists in rodents showed the predicted glucose lowering effects. For some such animal studies decreased food intake and weight loss was reported. Recently clinical trials with GPR119 agonists added evidence for a positive impact on lipid parameters i.e. elevation of HDL together with lowering of LDL and triglycerides in humans. WO2013/070463A2 discloses that GPR119 agonists may be used to treat abnormalities in blood lipids. In summary, modulators of GPR119, agonists in particular, may have therapeutic utility in the prevention and/or treatment of metabolic disorders in mammals and especially in humans. Examples of such disorders and diseases include type 2 diabetes mellitus, type 1 diabetes mellitus, impaired glucose tolerance, insulin resistance, loss of beta cell function, hyperglycemia, hypercholesterolemia, dyslipidemia, hypertriglyceridemia, syndrome X, metabolic syndrome, obesity, fatty liver, steatosis, steatohepatitis, cirrhosis, micro- and marcovascular disorders, high blood pressure, chronic low grade inflammation, retinopathy, neuropathy, nephropathy, atherosclerosis, coronary heart disease, endothelial dysfunction and bone-related diseases such as osteoporosis, rheumatoid arthritis or osteoarthritis.

Several modulators of GPR119 are known. For example WO2011146335 and WO2012037393 describe piperidinyl-substituted lactams as GPR119 modulators. WO2010048149 describes heterocyclic modulators of GPR119 for the treatment of disease and their preparation. WO2004110994 describes the preparation of piperazinyl-aryloxy and piperazinyl-heteroaryloxy-N-aryl lactams as 5-HT1B ligands.

It was an aim of the invention to provide novel compounds as active ingredients in pharmaceuticals.

It was an aim of the invention to provide novel compounds which will lower blood glucose in mammals and which are suitable for prevention and/or treatment of diabetes, obesity, dyslipidemia and related disorders.

A further aim was to provide novel GPR119 modulators, especially agonists, which can be used therapeutically for the prevention and/or treatment of diabetes, obesity, dyslipidemia and related disorders.

Accordingly a subject of the invention is a compound of the formula I

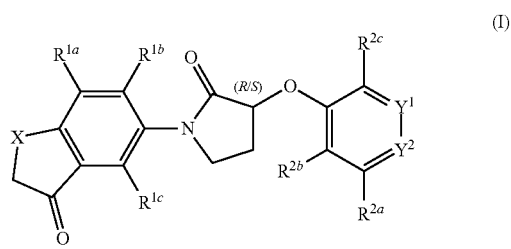

in which
X is selected from the series consisting of $CH_2$ and $CH_2$—$CH_2$;
$R^{1a}$ is selected from the series consisting of H, F, Cl, Br, $(C_1-C_6)$-alkyl and ON;
$R^{1b}$ is selected from the series consisting of H, F, Cl and $(C_1-C_6)$-alkyl;
$R^{1c}$ is selected from the series consisting of H, F, Cl and $(C_1-C_6)$-alkyl;
$R^{2a}$ is selected from the series consisting of H, F, Cl, Br, $(C_1-C_6)$-alkyl, CN, $CO_2R^5$ and $CONR^5R^{5'}$;
$R^{2b}$ is selected from the series consisting of H, F, Cl and $(C_1-C_6)$-alkyl;
$R^{2c}$ is selected from the series consisting of H, F, Cl and $(C_1-C_6)$-alkyl;
$R^5$, $R^{5'}$ are independently of each other selected from the series consisting of H and $(C_1-C_4)$-alkyl;
one of the groups $Y^1$ and $Y^2$ is N, N-oxide or $CR^{2d}$, the other is C—Z—$R^3$—$R^4$;
$R^{2d}$ is selected from the series consisting of H, F, Cl and $(C_1-C_4)$-alkyl;
Z is selected from the series consisting of a bond, O, CO, COO, S, SO and $SO_2$;
$R^3$ is selected from the series consisting of a bond and $(CR^6R^{6'})_n$,
$R^6$, $R^{6'}$ are independently of each other selected from the series consisting of H and $(C_1-C_6)$-alkyl, which is unsubstituted or monofluorinated;
n is selected from the series consisting of 1, 2, 3, 4 and 5;
$R^4$ is selected from the series consisting of $(C_1-C_6)$-alkyl, mono-, di- or trifluorinated $(C_1-C_6)$-alkyl, $(C_2-C_6)$-alkenyl, $(C_2-C_6)$-alkynyl, $CO_2R^5$, $OR^7$, $NR^8R^{8'}$, $SR^9$, $(C_3-C_8)$-cycloalkyl, a 4- to 6-membered saturated or partially unsaturated heterocycle, which comprises one or two identical or different ring heteroatoms selected from the series consisting of N and O, phenyl, a 5- to 6-membered heteroaryl, which comprises one, two or three identical or different ring heteroatoms selected from the series consisting of N, O and S, wherein all cyclic groups within $R^4$ are unsubstituted or substituted by one to three identical or different substituents selected from the series consisting of $(C_1-C_4)$-alkyl, $(C_1-C_4)$-alkanoyl, hydroxy-$(C_0-C_4)$-alkyl, $(C_1-C_3)$-alkoxy-$(C_0-C_4)$-alkyl, oxo (=O), F and Cl;

$R^7$ is selected from the series consisting of H, $(C_1-C_6)$-alkyl, hydroxy-$(C_1-C_4)$-alkyl and $(C_1-C_3)$-alkoxy-$(C_1-C_4)$-alkyl;

$R^8$, $R^{8'}$ are independently of each other selected from the series consisting of H and $(C_1-C_6)$-alkyl and $R^9$ is $(C_1-C_6)$-alkyl;

in any of its stereoisomeric forms, or a mixture of stereoisomeric forms in any ratio, or a physiologically acceptable salt thereof, or a physiologically acceptable solvate of any of them.

In another group of embodiments
the 3-position of the central pyrrolidinone ring has (R)-configuration.

In another group of embodiments
X is $CH_2$.

In another group of embodiments
$R^{1a}$ is selected from the series consisting of H, F, Cl, methyl and CN.

In another group of embodiments
$R^{1a}$ is F.

In another group of embodiments
$R^{1b}$ is H.

In another group of embodiments
$R^{1c}$ is selected from the series consisting of H, F and methyl.

In another group of embodiments
$R^{2a}$ is selected from the series consisting of H, F, Cl, methyl and CN.

In another group of embodiments
$R^{2b}$ is H.

In another group of embodiments
$R^{2c}$ is H.

In another group of embodiments
$R^{2d}$ is H.

In another group of embodiments
$Y^1$ is N and
$Y^2$ is C—Z—$R^3$—$R^4$.

In another group of embodiments
Z is O,
$Y^1$ is C—Z—$R^3$—$R^4$ and
$Y^2$ is N.

In another group of embodiments
Z is selected from the series consisting of O, S and bond.

In another group of embodiments
Z is O.

In another group of embodiments
$R^3$ is selected from the series consisting of a bond and $(CR^6R^{6'})_n$;

n is selected from the series consisting of 1, 2 and 3; and
$R^6$, $R^{6'}$ are independently of each other H or $(C_1-C_2)$-alkyl, and the overall number of carbon atoms in a $(CR^6R^{6'})_n$ group is below or equal to eight (8).

In another group of embodiments
$R^3$ is a bond.

In another group of embodiments
$R^3$ is selected from the series consisting of $CH_2$ and $CH_2$—$CH_2$.

In another group of embodiments
$R^4$ is selected from the series consisting of $(C_1-C_6)$-alkyl, mono-, di- or trifluorinated $(C_1-C_6)$-alkyl, $O(C_1-C_4)$-alkyl, $(C_3-C_8)$-cycloalkyl, a 4- to 6-membered heterocycle, which comprises one or two ring oxygen atoms, wherein all cyclic groups within $R^4$ are unsubstituted or substituted by $(C_1-C_4)$-alkyl.

In another group of embodiments
$R^4$ is $(C_3-C_6)$-cycloalkyl, which is unsubstituted or substituted by methyl.

In another group of embodiments
$R^3$ is selected from the series consisting of $CH_2$ and $CH_2$—$CH_2$ and
$R^4$ is $(C_3-C_6)$-cycloalkyl, which is unsubstituted or substituted by methyl.

In another group of embodiments the compound of the formula I is a compound of the formula Ia

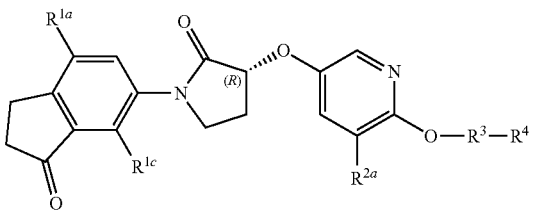

(Ia)

wherein
$R^{1a}$ is selected from the series consisting of H, F, Cl, $(C_1-C_4)$-alkyl and CN;
$R^{1c}$ is selected from the series consisting of H, F and $(C_1-C_4)$-alkyl;
$R^{2a}$ is selected from the series consisting of H, F, Cl, $(C_1-C_4)$-alkyl and CN;
$R^3$ is selected from the series consisting of a bond and $(CR^6R^{6'})_n$;
n is selected from the series consisting of 1, 2 and 3;
$R^6$, $R^{6'}$ are independently of each other H or $(C_1-C_2)$-alkyl, and the overall number of carbon atoms in a $(CR^6R^{6'})_n$ group is below or equal to eight (8) and
$R^4$ is selected from the series consisting of $(C_1-C_6)$-alkyl, mono-, di- or trifluorinated $O(C_1-C_4)$-alkyl, $(C_3-C_8)$-cycloalkyl, a 4- to 6-membered heterocycle, which comprises one or two ring oxygen atoms, wherein all cyclic groups within $R^4$ are unsubstituted or substituted by $(C_1-C_4)$-alkyl.

In another group of embodiments
X is selected from the series consisting of $CH_2$ and $CH_2$—$CH_2$;
$R^{1a}$ is selected from the series consisting of H, F, Cl, Br, $(C_1-C_4)$-alkyl and CN;
$R^{1b}$ is H;
$R^{1c}$ is selected from the series consisting of H, F and methyl;
$R^{2a}$ is selected from the series consisting of H, F, CN, $CO_2R^5$, $CONR^5R^{5'}$ and $(C_1-C_4)$-alkyl;
$R^{2b}$ is H;
$R^{2c}$ is H;
$R^5$, $R^{5'}$ are independently of each other selected from the series consisting of H and $(C_1-C_4)$-alkyl;
one of the groups $Y^1$ and $Y^2$ is N, N-oxide or $CR^{2d}$, the other is C—Z—$R^3$—$R^4$;
$R^{2d}$ is H;
Z is selected from the series consisting of a bond, O, CO, COO, S and SO;
$R^3$ is selected from the series consisting of a bond and $(CR^6R^{6'})_n$;
n is selected from the series consisting of 1, 2, 3, 4 and 5;

$R^6$, $R^{6'}$ are independently of each other selected from the series consisting of H, methyl, ethyl and 2-fluoro-ethyl, and the overall number of carbon atoms in a $(CR^6R^{6'})_n$ group is below or equal to eight (8);

$R^4$ is selected from the series consisting of $(C_1-C_6)$-alkyl, mono-, di- or trifluorinated $(C_1-C_6)$-alkyl, $(C_4-C_6)$-alkenyl, $CO_2R^5$, $OR^7$, $NR^8R^{8'}$, $SR^9$, $(C_3-C_6)$-cycloalkyl, a 4- to 6-membered heterocycle, which comprises one or two oxygen atoms or one nitrogen atom, phenyl, a 5- to 6-membered heteroaryl, which comprises one or two nitrogen atoms, one nitrogen and one oxygen atom, one nitrogen and one sulfur atom or two nitrogen atoms and one oxygen atom, wherein all cyclic groups within $R^4$ are unsubstituted or mono-substituted by substituents selected from the series consisting of F, $(C_1-C_4)$-alkyl, hydroxymethyl, acetyl, hydroxyl and oxo (=O);

$R^7$ is selected from the series consisting of H, methyl, ethyl and hydroxy-ethyl;

$R^8$, $R^{8'}$ are independently of each other $(C_1-C_4)$-alkyl and $R^9$ is methyl.

or a physiologically acceptable salt thereof, or a physiologically acceptable solvate of any of them.

In another group of embodiments

X is selected from the series consisting of $CH_2$ and $CH_2$—$CH_2$;

$R^{1a}$ is selected from the series consisting of H, F, Cl, Br, $(C_1-C_4)$-alkyl and CN;

$R^{1b}$ is H;

$R^{1c}$ is selected from the series consisting of H, F and methyl;

$R^{2a}$ is selected from the series consisting of H, F and $(C_1-C_4)$-alkyl;

$R^{2b}$ is H;

$R^{2c}$ is H;

one of the groups $Y^1$ and $Y^2$ is N, N-oxide or $CR^{2d}$, the other is C—Z—$R^3$—$R^4$;

$R^{2d}$ is H;

Z is selected from the series consisting of a bond, O, CO, COO, S and SO;

$R^3$ is selected from the series consisting of a bond and $(CR^6R^{6'})_n$, n is selected from the series consisting of 1, 2, 3, 4 and 5;

$R^6$, $R^{6'}$ are independently of each other selected from the series consisting of H, methyl, ethyl and 2-fluoro-ethyl, and the overall number of carbon atoms in a $(CR^6R^{6'})_n$ group is below or equal to eight (8);

$R^4$ is selected from the series consisting of $(C_1-C_6)$-alkyl, mono-, di- or trifluorinated $(C_1-C_6)$-alkyl, $(C_4-C_6)$-alkenyl, $CO_2R^5$, $OR^7$, $NR^8R^{8'}$, SW, $(C_3-C_6)$-cycloalkyl, a 4- to 6-membered heterocycle, which comprises one or two oxygen atoms or one nitrogen atom, phenyl, a 5- to 6-membered heteroaryl, which comprises one or two nitrogen atoms, one nitrogen and one oxygen atom, one nitrogen and one sulfur atom or two nitrogen atoms and one oxygen atom, wherein all cyclic groups within $R^4$ are unsubstituted or mono-substituted by substituents selected from the series consisting of F, $(C_1-C_4)$-alkyl, hydroxymethyl, acetyl, hydroxyl and oxo (=O);

$R^5$ is $(C_1-C_4)$-alkyl;

$R^7$ is selected from the series consisting of H, methyl, ethyl and hydroxy-ethyl;

$R^8$, $R^{8'}$ are independently of each other $(C_1-C_4)$-alkyl and $R^9$ is methyl.

In another group of embodiments $R^3$ is selected from the series consisting of a bond, $CH_2$, $(CH_2)_2$, $(CH_2)_3$, $(CH_2)_4$, $(CH_2)_5$, $CH(CH_3)$, $CH(C_2H_5)$, $CH(CH_3)$—$CH_2$, $CH(C_2H_5)$—$CH_2$, $CH_2$—$CH(CH_3)$, $CH_2$—$C(CH_3)_2$—$CH_2$, $(CH_2)_2$—$CH(CH_3)$ and $(CH_2)_2$—$C(CH_3)$—$(CH_2)_2$, and $CH(CH_2$—$CH_2$—F)—$CH_2$.

In another group of embodiments $R^4$ is selected from the series consisting of $(C_1-C_6)$-alkyl, mono-, di- or trifluorinated $(C_1-C_5)$-alkyl, pentenyl, OH, O-methyl, O-ethyl, O-ethylene-OH, S-methyl, $N(CH(CH_3)_2)_2$, $N(CH_3)$—$(CH_2)_3$—$CH_3$, $COOC_2H_5$, $(C_3-C_6)$-cycloalkyl, which is unsubstituted or mono-substituted by OH or methyl, a 4- to 6-membered heterocycle selected from the series consisting of oxetane, tetrahydrofuran, tetrahydropyran, [1,3]dioxolane, piperidine and pyrrolidine, which are unsubstituted or mono-substituted by substituents selected from the series consisting of methyl, acetyl and oxo (=O), phenyl, fluoro-phenyl, a 5- to 6-membered heteroaryl selected from the series consisting of imidazole, oxazole, pyrazole, thiazole, oxadiazole, pyridine and pyrazine, which are unsubstituted or mono-substituted by substitutents selected form the series consisting of methyl, isopropyl and hydroxymethyl.

In another group of embodiments $R^4$ is selected from the series consisting of $(C_1-C_6)$-alkyl, mono-, di- or trifluorinated pentenyl, OH, O-methyl, O-ethyl, O-ethylene-OH, S-methyl, $N(CH(CH_3)_2)_2$, $COOC_2H_5$, $(C_3-C_6)$-cycloalkyl, which is unsubstituted or mono-substituted by OH or methyl, a 4- to 6-membered heterocycle selected from the series consisting of oxetane, tetrahydrofuran, tetrahydropyran, [1,3]dioxolane, piperidine and pyrrolidine, which are unsubstituted or mono-substituted by substituents selected from the series consisting of methyl, acetyl and oxo (=O), phenyl, fluoro-phenyl, a 5- to 6-membered heteroaryl selected from the series consisting of imidazole, oxazole, pyrazole, pyridine and pyrazine, which are unsubstituted or mono-substituted by methyl.

In another embodiment compounds of the formula I are encompassed selected from the series consisting of Examples 1-01 to 1-20, 2-01 to 2-79, 3-01 to 3-21, 4-01 to 4-03, 5-01 to 5-10, 6-01, 7-01, 8-01 to 8-05 and 9-01 to 9-03.

In another embodiment compounds of the formula I are encompassed selected from the following list:

(R)-1-(7-Fluoro-3-oxo-indan-5-yl)-3-[6-(1-methyl-butoxy)-pyridin-3-yloxy]-pyrrolidin-2-one, (R)-3-(6-Ethoxy-pyridin-3-yloxy)-1-(7-fluoro-3-oxo-indan-5-yl)-pyrrolidin-2-one, (R)-1-(7-Fluoro-3-oxo-indan-5-yl)-3-[6-(2-methyl-butoxy)-pyridin-3-yloxy]-pyrrolidin-2-one, (R)-3-(6-sec-Butoxy-pyridin-3-yloxy)-1-(7-fluoro-3-oxo-indan-5-yl)-pyrrolidin-2-one, (R)-1-(7-Fluoro-3-oxo-indan-5-yl)-3-(6-pentyloxy-pyridin-3-yloxy)-pyrrolidin-2-one, (R)-1-(7-Fluoro-3-oxo-indan-5-yl)-3-(6-propoxy-pyridin-3-yloxy)-pyrrolidin-2-one, (R)-1-(7-Fluoro-3-oxo-indan-5-yl)-3-[6-(3-methyl-butoxy)-pyridin-3-yloxy]-pyrrolidin-2-one, (R)-1-(7-Fluoro-3-oxo-indan-5-yl)-3-(6-isobutoxy-pyridin-3-yloxy)-pyrrolidin-2-one, (R)-1-(7-Fluoro-3-oxo-indan-5-yl)-3-(6-isopropoxy-pyridin-3-yloxy)-pyrrolidin-2-one, (R)-3-[6-(2,2-Difluoro-ethoxy)-pyridin-3-yloxy]-1-(7-fluoro-3-oxo-indan-5-yl)-pyrrolidin-2-one, (R)-1-(7-Fluoro-3-oxo-indan-5-yl)-3-[6-(3,3,3-trifluoro-propoxy)-pyridin-3-yloxy]-pyrrolidin-2-one, (R)-3-[6-(2-Fluoro-1-fluoromethyl-ethoxy)-pyridin-3-yloxy]-1-(7-fluoro-3-oxo-indan-5-yl)-pyrrolidin-2-one, (R)-1-(7-Fluoro-3-oxo-indan-5-yl)-3-[6-(3-fluoro-propoxy)-pyridin-3-yloxy]-pyrrolidin-2-one, (R)-1-(7-Fluoro-3-oxo-indan-5-yl)-3-[6-(2,2,2-trifluoro-ethoxy)-pyridin-3-yloxy]-pyrrolidin-2-one and
(R)-3-(6-Butylsulfanyl-pyridin-3-yloxy)-1-(7-fluoro-3-oxo-indan-5-yl)-pyrrolidin-2-one.
In another embodiment compounds of the formula I are encompassed selected from the following list:
(R)-3-(6-Cyclopentyloxy-pyridin-3-yloxy)-1-(7-fluoro-3-oxo-indan-5-yl)-pyrrolidin-2-one,
(R)-3-(6-Cyclohexyloxy-pyridin-3-yloxy)-1-(7-fluoro-3-oxo-indan-5-yl)-pyrrolidin-2-one,
(R)-3-(6-Cyclobutoxy-pyridin-3-yloxy)-1-(7-fluoro-3-oxo-indan-5-yl)-pyrrolidin-2-one and
(R)-3-(6-Cyclopropoxy-pyridin-3-yloxy)-1-(7-fluoro-3-oxo-indan-5-yl)-pyrrolidin-2-one.
In another embodiment compounds of the formula I are encompassed selected from the following list:
(R)-3-[6-(2-Cyclopropyl-ethoxy)-pyridin-3-yloxy]-1-(7-fluoro-3-oxo-indan-5-yl)-pyrrolidin-2-one,
(R)-3-(6-Cyclopropylmethoxy-pyridin-3-yloxy)-1-(7-fluoro-3-oxo-indan-5-yl)-pyrrolidin-2-one,
(R)-3-[6-(1-Cyclopropyl-ethoxy)-pyridin-3-yloxy]-1-(7-fluoro-3-oxo-indan-5-yl)-pyrrolidin-2-one,
(R)-1-(7-Fluoro-3-oxo-indan-5-yl)-3-[6-(2-methyl-cyclopropylmethoxy)-pyridin-3-yloxy]-pyrrolidin-2-one,
(R)-1-(7-Fluoro-3-oxo-indan-5-yl)-3-[6-(1-methyl-cyclopropylmethoxy)-pyridin-3-yloxy]-pyrrolidin-2-one,
(R)-3-(6-Cyclopropylmethoxy-5-fluoro-pyridin-3-yloxy)-1-(7-fluoro-3-oxo-indan-5-yl)-pyrrolidin-2-one and
(R)-3-(6-Cyclopropylmethoxy-5-methyl-pyridin-3-yloxy)-1-(7-fluoro-3-oxo-indan-5-yl)-pyrrolidin-2-one.
In another embodiment compounds of the formula I are encompassed selected from the following list:
(R)-1-(7-Fluoro-3-oxo-indan-5-yl)-3-[6-(tetrahydro-furan-3-yloxy)-pyridin-3-yloxy]-pyrrolidin-2-one,
(R)-1-(7-Fluoro-3-oxo-indan-5-yl)-3-[6-(tetrahydro-pyran-4-yloxy)-pyridin-3-yloxy]-pyrrolidin-2-one,
(R)-1-(7-Fluoro-3-oxo-indan-5-yl)-3-[6-(tetrahydro-pyran-3-yloxy)-pyridin-3-yloxy]-pyrrolidin-2-one,
(R)-3-[6-(3-Ethoxy-propoxy)-pyridin-3-yloxy]-1-(7-fluoro-3-oxo-indan-5-yl)-pyrrolidin-2-one and
(R)-1-(7-Fluoro-3-oxo-indan-5-yl)-3-[6-((S)-2-methoxy-propoxy)-pyridin-3-yloxy]-pyrrolidin-2-one.
In another embodiment compounds of the formula I are encompassed selected from the following list:
(R)-3-[4-(2-Cyclopropyl-ethoxy)-phenoxy]-1-(7-fluoro-3-oxo-indan-5-yl)-pyrrolidin-2-one,
(R)-3-(6-Cyclopropylmethoxy-pyridin-3-yloxy)-1-(7-fluoro-3-oxo-indan-5-yl)-pyrrolidin-2-one,
(R)-1-(7-Fluoro-3-oxo-indan-5-yl)-3-[6-(tetrahydro-pyran-4-yloxy)-pyridin-3-yloxy]-pyrrolidin-2-one,
(R)-3-(6-Ethoxy-pyridin-3-yloxy)-1-(7-fluoro-3-oxo-indan-5-yl)-pyrrolidin-2-one,
(R)-1-(7-Fluoro-3-oxo-indan-5-yl)-3-(6-isopropoxy-pyridin-3-yloxy)-pyrrolidin-2-one and
(R)-3-(6-Cyclopropoxy-pyridin-3-yloxy)-1-(7-fluoro-3-oxo-indan-5-yl)-pyrrolidin-2-one.

Structural elements such as groups, substituents, hetero ring members, numbers or other features, for example alkyl groups, groups like $R^5$, $R^6$, $R^{6'}$ etc., which can occur several times in the compounds of the formula I, can all independently of one another have at each occurrence any of the indicated meanings and can in each case be identical to or different from one another. For example, the alkyl groups in a dialkylamino group can be identical or different.

Herein, the terms "including" and "comprising" are used in their open, non-limiting sense. As used herein, the terms "($C_1$-$C_6$)" and so forth refer to moieties having 1 to 6 carbon atoms and so forth, respectively. Within composed terms like "hydroxy-($C_0$-$C_4$)-alkyl" the option "($C_0$)-alkyl refers to a bond (i.e. in this case a directly bound hydroxy group), or in case of an unsubstituted "($C_0$)-alkyl" it refers to a hydrogen.

The term "alkyl", as used herein, refers to saturated, monovalent hydrocarbon radicals. The term "alkenyl", as used herein, refers to monovalent hydrocarbon radicals, which contain at least one carbon-carbon double bond, wherein each double bond can have E- or Z-configuration. The term "alkynyl", as used herein, refers to monovalent hydrocarbon radicals, which contain at least one carbon-carbon triple bond. The alkyl, alkenyl and alkynyl groups can be linear, i.e. straight-chain, or branched. This also applies when they are part of other groups, for example alkyloxy groups (=alkoxy groups, O-alkyl groups), alkyloxycarbonyl groups or alkyl-substituted amino groups, or when they are substituted. Depending on the respective definition, the number of carbon atoms in an alkyl group can be 1, 2, 3, 4, 5 or 6, or 1, 2, 3, or 4. Examples of alkyl are methyl, ethyl, propyl including n-propyl and isopropyl, butyl including n-butyl, sec-butyl, isobutyl and tert-butyl, pentyl including n-pentyl, 1-methylbutyl, isopentyl, neopentyl and tert-pentyl, hexyl including n-hexyl, 3,3-dimethylbutyl and isohexyl. Double bonds and triple bonds in alkenyl groups and alkynyl groups respectively can be present in any positions. Examples of alkenyl and alkynyl are ethenyl, prop-1-enyl, prop-2-enyl (=allyl), but-2-enyl, 2-methylprop-2-enyl, 3-methylbut-2-enyl, hex-3-enyl, hex-4-enyl, prop-2-ynyl (=propargyl), but-2-ynyl, but-3-ynyl, hex-4-ynyl or hex-5-ynyl. Substituted alkyl groups, alkenyl groups and alkynyl groups can be substituted in any positions, provided that the respective compound is sufficiently stable and is suitable for the desired purpose such as use as a drug substance. The prerequisite that a specific group and a compound of the formula I are sufficiently stable and suitable for the desired purpose such as use as a drug substance, applies in general with respect to the definitions of all groups in the compounds of the formula I.

Independently of one another and independently of any other substituents, alkyl groups, divalent alkyl groups, alkenyl groups, alkynyl groups, cycloalkyl groups and heterocycloalkyl groups are optionally substituted by one or more fluorine substituents which can be located in any positions, i.e., the said groups can be unsubstituted by fluorine substituents or substituted by fluorine substituents, for example by 1, 2 or 3, by 1 or 2, or by 1 fluorine substituents. Examples of fluorine-substituted said groups are trifluoromethyl, difluoromethyl and fluoromethyl.

The term "alkanediyl" or "alkylene"", as used herein, refers to saturated, divalent hydrocarbon radicals. The term "alkenediyl", as used herein, refers to divalent hydrocarbon radicals, which contain at least one carbon-carbon double bond, wherein each double bond can have E- or Z-configuration. The term "alkyndiyl", as used herein, refers to divalent hydrocarbon radicals, which contain at least one carbon-carbon triple bond. As far as applicable, the preceding explanations regarding alkyl, alkenyl and alkynyl groups apply correspondingly to alkanediyl, alkendiyl and alkyndiyl groups, which thus can likewise be linear and branched. Examples of divalent alkyl groups are —$CH_2$— (=methylene), —$CH_2$—$CH_2$—, —$CH_2$—$CH_2$—$CH_2$—, —$CH_2$—$CH_2$—$CH_2$—$CH_2$—, —$CH(CH_3)$—, —$C(CH_3)_2$—, —$CH(CH_3)$—$CH_2$—, —$CH_2$—$CH(CH_3)$—, —$C(CH_3)_2$—$CH_2$— and —$CH_2$—$C(CH_3)_2$—.

The term "cycloalkyl", as used herein, unless otherwise indicated, refers to a mono-valent radical of a saturated hydrocarbon ring system, which is monocyclic. In a monocyclic cycloalkyl group the number of ring carbon atoms can be for example 3, 4, 5, 6, 7 or 8. In one embodiment of the invention, the number of ring carbon atoms in a cycloalkyl group, independently of the number of ring carbon atoms in any other cycloalkyl group is 3, 4, 5 or 6, in another embodiment 3 or 4, in another embodiment 3, in another embodiment 5 or 6, in another embodiment 5, in another embodiment 6. Examples of cycloalkyl groups are cyclopropyl, cyclobutyl, cyclopentyl and cyclohexyl. The term "heterocycle", as used herein, unless otherwise indicated, refers to a cycloalkyl as defined above, in which 1, 2, 3 or 4 carbon atoms are replaced by nitrogen or oxygen atoms, provided that the heterocycloalkyl system is stable and suitable as a subgroup for the desired purpose of the compound of the formula I such as use as a drug substance. Depending on the definition of the respective heterocyclic group, in one embodiment of the invention the number of ring heteroatoms which can be present in a heterocyclic group, independently of the number of ring heteroatoms in any other heterocyclic group, is 1 or 2, in another embodiment 2, in another embodiment 1, wherein the ring heteroatoms can be identical or different. The heterocycloalkyl group can be attached by any ring carbon atom or saturated ring nitrogen atom, with the exception of spiro- or bridgehead atoms.

Exemplary monocyclic heterocycloalkyl groups are derived from, but not limited to, the ring systems azetidine, oxetane, pyrrolidine, tetrahydrofuran, 1,3-dioxolane, piperidine, piperazine, morpholine, tetrahydropyran or 1,4-dioxane:

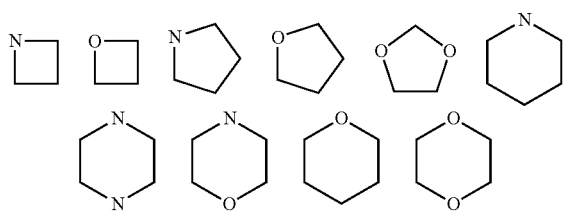

In one embodiment monocyclic heterocycloalkyl groups are derived from azetidine, pyrrolidine, piperidine, piperazine or morpholine:

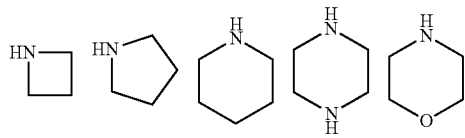

The term "aryl", as used herein, refers to a radical derived from an aromatic hydro-carbon by removal of one hydrogen, such as phenyl.

The term "heteroaryl" as used herein, refers to a radical derived from a fully unsaturated monocyclic ring system, in which 1, 2 or 3 carbon atoms are replaced by heteroatoms. The ring heteroatoms are generally chosen from N, O and S, wherein N includes ring nitrogen atoms which carry a hydrogen atom or a substituent as well as ring nitrogen atoms which do not carry a hydrogen atom or a substituent. Ring heteroatoms can be located in any position, provided that the heterocyclic system is stable and suitable as a subgroup for the desired purpose of the compound of the formula I such as use as a drug substance. Heteroaryl radicals are derived from 5-membered or 6-membered monocyclic rings.

Exemplary heteroaryl systems are derived from, but not limited to, the following ring systems: pyrrole, furan, thiophene, imidazole, pyrazole, oxazole (=[1,3]oxazole), isoxazole (=[1,2]oxazole), thiazole (=[1,3]thiazole), isothiazole (=[1,2]thiazole), [1,2,3]triazole, [1,2,4]triazole, [1,2,4]oxadiazole, [1,3,4]oxadiazole, [1,2,4]thiadiazole, [1,3,4]thiadiazole, pyridine, pyridazine, pyrimidine, pyrazine, [1,2,3]triazine, [1,2,4]triazine or [1,3,5]triazine:

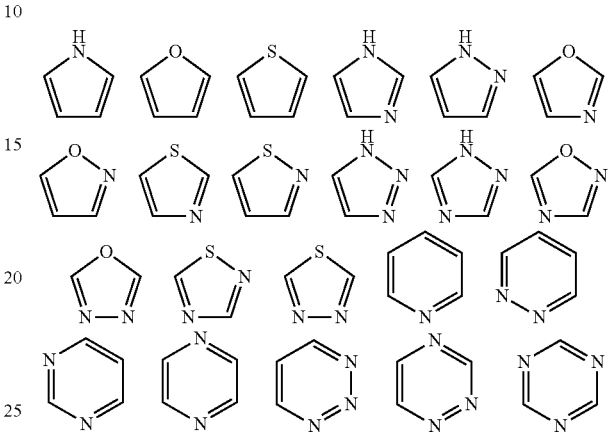

Groups like phenyl and residues of aromatic heterocycles which are optionally substituted by one or more substituents, can be unsubstituted or substituted, for example by 1, 2 or 3, or by 1 or 2, or by 1, identical or different substituents which can be located in any positions. Aromatic nitrogen heterocycles which in the parent ring system carry a hydrogen atom on a ring nitrogen atom in a 5-membered ring, such as a pyrrole or imidazole ring, for example, can be substituted on ring carbon atoms and/or on such ring nitrogen atoms. In one embodiment of the invention, substituents on such ring nitrogen atoms are chosen from $(C_1-C_4)$-alkyl groups, i.e. such ring nitrogen atoms in aromatic heterocycles carry a hydrogen atom or a $(C_1-C_4)$-alkyl substituent. When it is stated with respect to ring nitrogen atoms in aromatic heterocycles and any other heterocycles that they can carry a hydrogen atom or a substituent, such ring nitrogen atoms either carry a hydrogen atom or a substituent or they do not carry a hydrogen atom or substituent. Ring nitrogen atoms which carry a hydrogen atom or a substituent, occur in a nitrogen-containing aromatic 5-membered ring as is present in pyrrole or imidazole for example, and in a non-aromatic ring including a saturated ring. Ring nitrogen atoms which do not carry a hydrogen atom or a substituent unless they are present in positively charged form, including any further ring nitrogen atoms in addition to ring nitrogen atoms which carry a hydrogen atom or a substituent, occur in an aromatic ring as is present in thiazole, imidazole or pyridine, for example, and in a non-aromatic ring in which they are part of a double bond, and they occur as ring nitrogen atoms via which a ring is bonded. Suitable ring nitrogen atoms in aromatic heterocycles in the compounds of the formula I, such as the ring nitrogen atom in a pyridine ring, can in general also be present as N-oxide or as quaternary salt, for example as N—$(C_1-C_4)$-alkyl salt such as N-methyl salt, wherein in one embodiment of the invention the counter anion in such quaternary salt is a physiologically acceptable anion which is derived from an acid that forms a physiologically acceptable salt.

In monosubstituted phenyl groups, the substituent can be located in the 2-position, the 3-position or the 4-position. In disubstituted phenyl groups, the substituents can be located in 2,3-position, 2,4-position, 2,5-position, 2,6-position, 3,4-position or 3,5-position. In trisubstituted phenyl groups, the substituents can be located in 2,3,4-position, 2,3,5-position, 2,3,6-position, 2,4,5-position, 2,4,6-position or 3,4,5-position.

Ring heteroatoms can be located in any positions, provided that the heterocyclic system is known in the art and is stable and suitable as a subgroup for the desired purpose of the compound of the formula I such as use as a drug substance. In one embodiment of the invention, two ring oxygen atoms cannot be present in adjacent ring positions of any heterocycle, in another embodiment two ring heteroatoms chosen from oxygen and sulfur cannot be present in adjacent ring positions of any heterocycle. Substituents on heterocyclic groups can be located in any positions. For example, in a pyridin-2-yl group substituents can be located in the 3-position and/or 4-position and/or 5-position and/or 6-position, in a pyridin-3-yl group substituent can be located in the 2-position and/or 4-position and/or 5-position and/or 6-position, in a pyridin-4-yl group substituents can be located in the 2-position and/or 3-position and/or 5-position and/or 6-position.

When an oxo group is bonded to a carbon atom, it replaces two hydrogen atoms on a carbon atom of the parent system. Thus, if a $CH_2$ group in a chain or a ring is substituted by oxo, i.e. by a doubly bonded oxygen atom, it becomes a CO group.

Evidently, an oxo group cannot occur as a substituent on a carbon atom in an aromatic ring such as in a phenyl group, for example.

The present invention includes all stereoisomeric forms of the compounds of the formula I and their salts and solvates. With respect to each chiral center, independently of any other chiral center, the compounds of the formula I can be present in S configuration or substantially S configuration, or in R configuration or substantially R configuration, or as a mixture of the S isomer and the R isomer in any ratio. The invention includes all possible enantiomers and diastereomers and mixtures of two or more stereoisomers, for example mixtures of enantiomers and/or diastereomers, in all ratios. Thus, compounds according to the invention which can exist as enantiomers can be present in enantiomerically pure form, both as levorotatory and as dextrorotatory antipodes, and in the form of mixtures of the two enantiomers in all ratios including racemates. In the case of a E/Z isomerism, or cis/trans isomerism, for example on double bonds or rings such as cycloalkyl rings, the invention includes both the E form and Z form, or the cis form and the trans form, as well as mixtures of these forms in all ratios. In one embodiment of the invention, a compound which can occur in two or more stereoisomeric forms is a pure, or substantially pure, individual stereoisomer. The preparation of individual stereoisomers can be carried out, for example, by separation of a mixture of isomers by customary methods, for example by chromatography or crystallization, by the use of stereochemically uniform starting materials in the synthesis, or by stereoselective synthesis. Optionally, a derivatization can be carried out before a separation of stereoisomers. The separation of a mixture of stereoisomers can be carried out at the stage of the compound of the formula I or at the stage of a starting material or an intermediate during the synthesis. The present invention also includes all tautomeric forms of the compounds of the formula I and their salts and solvates.

In case the compounds of the formula I contain one or more acidic and/or basic groups, i.e. salt-forming groups, the invention also includes their corresponding physiologically or toxicologically acceptable salts, i.e, non-toxic salts, in particular their pharmaceutically acceptable salts.

The present invention furthermore includes all solvates of compounds of the formula I, for example hydrates or adducts with alcohols such as $(C_1-C_4)$-alkanols, active metabolites of the compounds of the formula I, and also prodrugs and derivatives of the compounds of the formula I which in vitro may not necessarily exhibit pharmacological activity but which in vivo are converted into pharmacologically active compounds, for example esters or amides of carboxylic acid groups.

The compounds of the present invention can be widely combined with other pharmacologically active compounds, such as all drugs mentioned in the Rote Liste 2012, e.g. all antidiabetics mentioned in the Rote Liste 2012, chapter 12, all weight-reducing agents or appetite suppressants mentioned in the Rote Liste 2012, chapter 1, all lipid-lowering agents mentioned in the Rote Liste 2012, chapter 58, all antihypertensives mentioned in the Rote Liste 2012 chapter 17, all nephroprotectives mentioned in the Rote Liste, or all diuretics mentioned in the Rote Liste 2012, chapter 36.

The active ingredient combinations can be applied either by separate administration of the active ingredients to the patient or in the form of combination products in which a plurality of active ingredients are present in one pharmaceutical preparation. When administered separately, administration may occur simultaneously or sequentially, in any order. The amount of the compound of the invention and the other pharmaceutically active ingredient(s) and the relative timings of administration will be selected in order to achieve the desired combined therapeutic effect. The administration of the combination may be concomitantly in: (1) a unitary pharmaceutical composition including all pharmaceutically active ingredients; or (2) separate pharmaceutical compositions each including at least one of the pharmaceutically active ingredients. Alternatively, the combination may be administered separately in a sequential manner wherein one treatment agent is administered first and the other second or vice versa. Such sequential administration may be close in time or remote in time.

Most of the active ingredients mentioned hereinafter are disclosed in the USP Dictionary of USAN and International Drug Names, US Pharmacopeia, Rockville 2012.

Therapeutic agents which are suitable for combinations include, for example, antidiabetic agents such as:

Insulin and insulin derivatives, for example: insulin glargine (e.g. Lantus®), insulin glulisine (e.g. Apidra®), insulin detemir (e.g. Levemir®), insulin lispro (e.g. Humalog®, Liprolog®), insulin degludec (e.g. DegludecPlus®, IdegLira (NN9068)), insulin aspart and aspart formulations (e.g. NovoLog®), basal insulin and analogues (e.g. LY2605541, LY2963016), PEGylated insulin lispro (e.g. LY-275585), long-acting insulins (e.g. NN1436, Insumera (PE0139), AB-101, AB-102, Sensulin LLC), intermediate-acting insulins (e.g. Humulin®N, Novolin®N), fast-acting and short-acting insulins (e.g. Humulin®R, Novolin®R, Linjeta®(VIAject®), PH20 insulin, NN1218, HinsBet®), premixed insulins, SuliXen®, NN1045, insulin plus Symlin®, ACP-002 insulin, and oral, inhalable, transdermal and buccal or sublingual insulins (e.g. Exubera®, Nasulin®, Afrezza®, insulin tregopil, TPM-02 Insulin, Capsulin®, Cobalamin® oral insulin, ORMD-0801, Oshadi oral insulin, NN1953, NN1954, NN1956, VIAtab®). Also suitable are those insulin derivatives which are bonded to albumin or another protein by a bifunctional linker.

Glucagon-like-peptide 1 (GLP-1), GLP-1 analogues, and GLP-1 receptor agonists, for example: lixisenatide (e.g. Lyxumia®), exenatide (e.g. exendin-4, rExendin-4, Byetta®, Bydureon®, exenatide NexP), liraglutide (e.g. Victoza®), semaglutide, taspoglutide, albiglutide, dulaglutide, ACP- 003, CJC-1134-PC, GSK-2374697, PB-1023, TTP-054, langlenatide (HM-11260C), CM-3, AB-201, ORMD-0901, NN9924, NN9926, NN9927, Nodexen, Viador-GLP-1, CVX-096, ZYOG-1, ZYD-1, ZP-3022, CAM-2036, DA-3091, DA-15864, ARI-2651, ARI-2255, exenatide-XTEN (VRS-859), exenatide-XTEN+Glucagon-XTEN (VRS-859+AMX-808) and polymer-bound GLP-1 and GLP-1 analogues.

Dual GLP-1/GIP agonists (e.g. RG-7697 (MAR-701), MAR-709, BHM081, BHM089, BHM098).

Dual GLP-1/glucagon receptor agonists (e.g. BHM-034, OAP-189 (PF-05212389, TKS-1225), TT-401/402, ZP2929, LAPS-HMOXM25, MOD-6030).

Dual GLP-1/gastrin agonists (e.g. ZP-3022).

Other suitable combination partners are:

Further gastrointestinal peptides such as peptide YY 3-36 (PYY3-36) or analogues thereof and pancreatic polypeptide (PP) or analogues thereof.

Glucagon receptor agonists or antagonists, glucose-dependent insulinotropic polypeptide (GIP) receptor agonists or antagonists, ghrelin antagonists or inverse agonists, xenin and analogues thereof.

Dipeptidyl peptidase-IV (DPP-4) inhibitors, for example: alogliptin (e.g. Nesina®, Kazano®), linagliptin (e.g. Ondero®, Trajenta®, Tradjenta®, Trayenta®), saxagliptin (e.g. Onglyza®, Komboglyze XR®), sitagliptin (e.g. Januvia®, Xelevia®, Tesavel®, Janumet®, Velmetia®, Juvisync®, Janumet XR®), anagliptin, teneligliptin (e.g. Tenelia®), trelagliptin, vildagliptin (e.g. Galvus®, Galvumet®), gemigliptin, omarigliptin, evogliptin, dutogliptin, DA-1229, MK-3102, KM-223, KRP-104, PBL-1427, Pinoxacin hydrochloride, and Ari-2243.

Sodium-dependent glucose transporter 2 (SGLT-2) inhibitors, for example: canagliflozin, dapagliflozin, remogliflozin, remogliflozin etabonate, sergliflozin, empagliflozin, ipragliflozin, tofogliflozin (RO-4998452), luseogliflozin, ertugliflozin (PF-04971729), EGT-0001442, LIK-066, SBM-TFC-039, and KGA-3235 (DSP-3235). Dual inhibitors of SGLT-2 and SGLT-1 (e.g. LX-4211, LIK066). SGLT-1 inhibitors (e.g. LX-2761, KGA-3235) or SGLT-1 inhibitors in combination with anti-obesity drugs such as ileal bile acid transfer (IBAT) inhibitors (e.g. GSK-1614235+GSK-2330672).

Biguanides (e.g. metformin, buformin, phenformin).

Thiazolidinediones (e.g. pioglitazone, rivoglitazone, rosiglitazone, troglitazone), glitazone analogues (e.g. lobeglitazone).

Peroxisome proliferator-activated receptors (PPAR-)(alpha, gamma or alpha/gamma) agonists or modulators (e.g. aleglitazar, muraglitazar, tesaglitazar, saroglitazar (e.g. Lipaglyn®), GFT-505).

Sulfonylureas (e.g. tolbutamide, glibenclamide, glimepiride, Amaryl®, glipizide) and meglitinides (e.g. nateglinide, repaglinide, mitiglinide).

Alpha-glucosidase inhibitors (e.g. acarbose, miglitol, voglibose).

Amylin and amylin analogues (e.g. pramlintide, Symlin®).

G-protein coupled receptor 119 (GPR119) agonists (e.g. GSK-1292263, PSN-821, MBX-2982, APD-597, ARRY-981, ZYG-19, DS-8500, HM-47000, YH-Chem1).

GPR40 agonists (e.g. fasiglifam (TAK-875), TUG-424, P-1736, P-11187, JTT-851, GW9508, CNX-011-67, AM-1638, AM-5262).

GPR120 agonists and GPR142 agonists.

Systemic or low-absorbable TGR5 (GPBAR1=G-protein-coupled bile acid receptor 1) agonists (e.g. INT-777, XL-475, SB756050).

Other suitable combination partners are:

Diabetes immunotherapeutics, for example: oral C—C chemokine receptor type 2 (CCR-2) antagonists (e.g. CCX-140), interleukin 1 beta (IL-111) antagonists (e.g. AC-201), or oral monoclonal antibodies (MoA) (e.g. methalozamide, WP808, PAZ-320, P-1736, PF-05175157, PF-04937319).

Anti-inflammatory agents for the treatment of the metabolic syndrome and diabetes, for example: nuclear factor kappa B inhibitors (e.g. Triolex®).

Adenosine monophosphate-activated protein kinase (AMPK) stimulants, for example: Imeglimin (PXL-008), Debio-0930 (MT-63-78), R-481.

Inhibitors of 11-beta-hydroxysteroid dehydrogenase 1 (11-beta-HSD-1) (e.g. LY2523199, BMS770767, RG-4929, BMS816336, AZD-8329, HSD-016, BI-135585).

Activators of glucokinase (e.g. PF-04991532, TTP-399 (GK1-399), GKM-001 (ADV-1002401), ARRY-403 (AMG-151), TAK-329, TMG-123, ZYGK1).

Inhibitors of diacylglycerol O-acyltransferase (DGAT) (e.g. pradigastat (LCQ-908)), inhibitors of protein tyrosine phosphatase 1 (e.g. trodusquemine), inhibitors of glucose-6-phosphatase, inhibitors of fructose-1,6-bisphosphatase, inhibitors of glycogen phosphorylase, inhibitors of phosphoenol pyruvate carboxykinase, inhibitors of glycogen synthase kinase, inhibitors of pyruvate dehydrogenase kinase.

Modulators of glucose transporter-4, somatostatin receptor 3 agonists (e.g. MK-4256).

One or more lipid lowering agents are also suitable as combination partners, for example: 3-hydroxy-3-methylglutaryl-coenzym-A-reductase (HMG-CoA-reductase) inhibitors such as simvastatin (e.g. Zocor®, Inegy®, Simcor®), atorvastatin (e.g. Sortis®, Caduet®), rosuvastatin (e.g. Crestor®), pravastatin (e.g. Lipostat®, Selipran®), fluvastatin (e.g. Lescol®), pitavastatin (e.g. Livazo®, Livalo®), lovastatin (e.g. Mevacor®, Advicor), mevastatin (e.g. Compactin®), rivastatin, cerivastatin (Lipobay®), fibrates such as bezafibrate (e.g. Cedur® retard), ciprofibrate (e.g. Hyperlipen®), fenofibrate (e.g. Antara®, Lipofen®, Lipanthyl®), gemfibrozil (e.g. Lopid®, Gevilon®), etofibrate, simfibrate, ronifibrate, clinofibrate, clofibride, nicotinic acid and derivatives thereof (e.g. niacin, including slow release formulations of niacin), nicotinic acid receptor 1 agonists (e.g. GSK-256073), PPAR-delta agonists, acetyl-CoA-acetyltransferase (ACAT) inhibitors (e.g. avasimibe), cholesterol absorption inhibitors (e.g. ezetimibe, Ezetrol®, Zetia®, Liptruzet®, Vytorin®, S-556971), bile acid-binding substances (e.g. cholestyramine, colesevelam), ileal bile acid transport (IBAT) inhibitors (e.g. GSK-2330672, LUM-002), microsomal triglyceride transfer protein (MTP) inhibitors (e.g. lomitapide (AEGR-733), SLx-4090, granotapide), modulators of proprotein convertase subtilisin/kexin type 9 (PCSK9) (e.g. alirocumab (REGN727/SAR236553), AMG-145, LGT-209, PF-04950615, MPSK3169A, LY3015014, ALD-306, ALN-PCS, BMS-962476, SPC5001, ISIS-394814, 1B20, LGT-210, 1 D05, BMS-PCSK9Rx-2, SX-PCK9, RG7652), LDL receptor up-regulators, for example liver selective thyroid hormone receptor beta agonists (e.g. eprotirome (KB-2115), MB07811, sobetirome (QRX-431), VIA-3196, ZYT1), HDL-raising compounds such as: cholesteryl ester transfer protein (CETP) inhibitors (e.g. torcetrapib, anacetrapib (MK0859), dalcetrapib, evacetrapib, JTT-302, DRL-17822, TA-8995, R-1658, LY-2484595, DS-1442), ATP-binding cassette (ABC1) regulators, lipid metabolism modulators (e.g. BMS-823778, TAP-301, DRL-21994, DRL-21995), phospholipase A2 (PLA2) inhibitors (e.g. darapladib, Tyrisa®, varespladib, rilapladib), ApoA-I enhancers (e.g. RVX-208, CER-001, MDCO-216, CSL-112), cholesterol synthesis inhibitors (e.g. ETC-1002), lipid metabolism modulators (e.g. BMS-823778, TAP-301, DRL-21994, DRL-21995) and omega-3 fatty acids and derivatives thereof (e.g. icosapent ethyl (AMR101), Epanova®, AKR-063, NKPL-66, PRC-4016, CAT-2003).

Other suitable combination partners are one or more active substances for the treatment of obesity, such as for example:

Bromocriptine (e.g. Cycloset®, Parlodel®), phentermine and phentermine formulations or combinations (e.g. Adipex-P, Ionamin, Qsymia®), benzphetamine (e.g. Didrex®), diethylpropion (e.g. Tenuate®), phendimetrazin (e.g. Adipost®, Bontril®), bupropion and combinations (e.g. Zyban®, Wellbutrin XL®, Contrave®, Empatic®), sibutramine (e.g. Reductil®, Meridia®), topiramat (e.g. Topamax®), zonisamid (e.g. Zonegran®), tesofensine, opioid antagonists such as naltrexone (e.g. Naltrexin®, naltrexone bupropion), cannabinoid receptor 1 (CB1) antagonists (e.g. TM-38837), melanin-concentrating hormone (MCH-1) antagonists (e.g. BMS-830216, ALB-127158(a)), MC4 receptor agonists and partial agonists (e.g. AZD-2820, RM-493), neuropeptide Y5 (NPY5) or NPY2 antagonists (e.g. velneperit, S-234462), NPY4 agonists (e.g. PP-1420), beta-3-adrenergic receptor agonists, leptin or leptin mimetics, agonists of the 5-hydroxytryptamine 2c (5HT2c) receptor (e.g. lorcaserin, Belviq®), pramlintide/metreleptin, lipase inhibitors such as cetilistat (e.g. Cametor®), orlistat (e.g. Xenical®, Calobalin®), angiogenesis inhibitors (e.g. ALS-L1023), betahistidin and histamine H3 antagonists (e.g. HPP-404), AgRP (agouti related protein) inhibitors (e.g. TTP-435), serotonin re-uptake inhibitors such as fluoxetine (e.g. Fluctine®), duloxetine (e.g. Cymbalta®), dual or triple monoamine uptake inhibitors (dopamine, norepinephrine and serotonin re-uptake) such as sertraline (e.g. Zoloft®), tesofensine, methionine aminopeptidase 2 (MetAP2) inhibitors (e.g. beloranib), and antisense oligonucleotides against production of fibroblast growth factor receptor 4 (FGFR4) (e.g. ISIS-FGFR4Rx) or prohibitin targeting peptide-1 (e.g. Adipotide®).

Moreover, combinations with drugs for influencing high blood pressure, chronic heart failure or atherosclerosis, for example: nitric oxide donors, AT1 antagonists or angiotensin II (AT2) receptor antagonists such as telmisartan (e.g. Kinzal®, Micardis®), candesartan (e.g. Atacand®, Blopress®), valsartan (e.g. Diovan®, Co-Diovan®), losartan (e.g. Cosaar®), eprosartan (e.g. Teveten®), irbesartan (e.g. Aprovel®, CoAprovel®), olmesartan (e.g. Votum®, Olmetec®), tasosartan, azilsartan (e.g. Edarbi®), dual angiotensin receptor blockers (dual ARBs), angiotensin converting enzyme (ACE) inhibitors, ACE-2 activators, renin inhibitors, prorenin inhibitors, endothelin converting enzyme (ECE) inhibitors, endothelin receptor (ET1/ETA) blockers, endothelin antagonists, diuretics, aldosterone antagonists, aldosterone synthase inhibitors, alpha-blockers, antagonists of the alpha-2 adrenergic receptor, beta-blockers, mixed alpha-/beta-blockers, calcium antagonists, calcium channel blockers (CCBs), nasal formulations of the calcium channel blocker diltiazem (e.g. CP-404), dual mineralocorticoid/CCBs, centrally acting antihypertensives, inhibitors of neutral endopeptidase, aminopeptidase-A inhibitors, vasopeptide inhibitors, dual vasopeptide inhibitors such as neprilysin-ACE inhibitors or neprilysin-ECE inhibitors, dual-acting AT receptor-neprilysin inhibitors, dual AT1/ETA antagonists, advanced glycation end-product (AGE) breakers, recombinant renalase, blood pressure vaccines such as anti-RAAS (renin-angiotensin-aldosteron-system) vaccines, AT1- or AT2-vaccines, drugs based on hypertension pharmacogenomics such as modulators of genetic polymorphisms with antihypertensive response, thrombocyte aggregation inhibitors, and others or combinations thereof are suitable.

In another aspect, this invention relates to the use of a compound according to the invention or a physiologically acceptable salt thereof combined with at least one of the active substances described above as a combination partner, for preparing a medicament which is suitable for the treatment or prevention of diseases or conditions which can be affected by binding to the GPR119 and modulating its activity. This is preferably a disease in the context of the metabolic syndrome, particularly one of the diseases or conditions listed above, most particularly diabetes or obesity or complications thereof.

The use of the compounds according to the invention, or a physiologically acceptable salt thereof, in combination with one or more active substances may take place simultaneously, separately or sequentially.

The use of the compound according to the invention, or a physiologically acceptable salt thereof, in combination with another active substance may take place simultaneously or at staggered times, but particularly within a short space of time. If they are administered simultaneously, the two active substances are given to the patient together; if they are used at staggered times, the two active substances are given to the patient within a period of less than or equal to 12 hours, but particularly less than or equal to 6 hours.

Consequently, in another aspect, this invention relates to a medicament which comprises compounds according to the invention or a physiologically acceptable salt of such a compound and at least one of the active substances described above as combination partners, optionally together with one or more inert carriers and/or diluents.

The compounds according to the invention, or physiologically acceptable salt or solvate thereof, and the additional active substance to be combined therewith may both be present together in one formulation, for example a tablet or capsule, or separately in two identical or different formulations, for example as so-called kit-of-parts.

Compounds according to the invention can be administered to animals, in particular to mammals including humans, as pharmaceuticals by themselves, in mixtures with one another, or in the form of pharmaceutical compositions. The administration can be carried out orally, for example in the form of tablets, film-coated tablets, sugar-coated tablets, granules, hard and soft gelatin capsules, solutions including aqueous, alcoholic and oily solutions, juices, drops, syrups, emulsions or suspensions, rectally, for example in the form of suppositories, or parenterally, for example in the form of solutions for subcutaneous, intramuscular or intravenous injection or infusion, in particular aqueous solutions.

Suitable pharmaceutical compositions for oral administration may be in the form of separate units, for example capsules, cachets, lozenges or tablets, each of which contains a defined amount of the compound of formula I; as powders or granules; as solution or suspension in an aqueous or nonaqueous liquid; or as an oil-in-water or water-in-oil emulsion. These compositions may, as already mentioned, be prepared by any suitable pharmaceutical method which includes a step in which the active ingredient and the carrier (which may consist of one or more additional ingredients) are brought into contact. The compositions are generally produced by uniform and homogeneous mixing of the active ingredient with a liquid and/or finely divided solid carrier, after which the product is shaped if necessary. Thus, for example, a tablet can be produced by compressing or molding a powder or granules of the compound, where appropriate with one or more additional ingredients. Compressed tablets can be produced by tableting the compound in free-flowing form such as, for example, a powder or granules, where appropriate mixed with a binder, glidant, inert diluent and/or one (or more) surfactant(s)/dispersant(s) in a suitable machine. Molded tablets can be produced by molding the compound, which is in powder form and has been moistened with an inert liquid diluent, in a suitable machine.

Pharmaceutical compositions which are suitable for peroral (sublingual) administration comprise lozenges which contain a compound of formula I with a flavoring, typically sucrose, and gum arabic or tragacanth, and pastilles which comprise the compound in an inert base such as gelatin and glycerol or sucrose and gum arabic.

Coated formulations and coated slow-release formulations, especially acid- and gastric juice-resistant formulations, also belong within the framework of the invention. Suitable coatings resistant to gastric juice comprise cellulose acetate phthalate, polyvinyl acetate phthalate, hydroxypropylmethylcellulose phthalate and anionic polymers of methacrylic acid and methyl methacrylate.

Pharmaceutical compositions suitable for rectal administration are preferably in the form of single-dose suppositories. These can be produced by mixing a compound of formula I with one or more conventional solid carriers, for example cocoa butter, and shaping the resulting mixture.

Pharmaceutical compositions suitable for parenteral administration comprise preferably sterile aqueous preparations of a compound of formula I, which are preferably isotonic with the blood of the intended recipient. These preparations are preferably administered intravenously, although administration may also take place by subcutaneous, intramuscular or intradermal injection. These preparations can preferably be produced by mixing the compound with water and making the resulting solution sterile and isotonic with blood. Injectable compositions of the invention generally contain 0.1 to 5% by weight of the active compound.

Other suitable administration forms are, for example, percutaneous or topical administration, for example in the form of ointments, creams, tinctures, sprays, powders or transdermal therapeutic systems, or inhalative administration, for example in the form of nasal sprays or aerosol mixtures, or forms such as microcapsules, implants or rods.

Pharmaceutical compositions suitable for topical use on the skin are preferably in the form of ointment, cream, lotion, paste, spray, aerosol or oil. The carriers used may be petrolatum, lanolin, polyethylene glycols, alcohols and combinations of two or more of these substances. The active ingredient is generally present in a concentration of 0.1 to 15% by weight of the composition, for example 0.5 to 2%.

Transdermal administration is also possible. Pharmaceutical compositions suitable for transdermal uses may be in the form of single patches which are suitable for long-term close contact with the patient's epidermis. Such patches suitably contain the active ingredient in an aqueous solution which is buffered where appropriate, dissolved and/or dispersed in an adhesive or dispersed in a polymer. A suitable active ingredient concentration is about 1% to 35%, preferably about 3% to 15%. A particular option is for the active ingredient to be released by electrotransport or iontophoresis as described, for example, in Pharmaceutical Research, 2(6): 318 (1986).

Compounds according to the invention can additionally be used in systems for local drug delivery, for example in coated stents for preventing or reducing in-stent restenosis or by applying them locally by means of a catheter. The appropriate administration form depends, among others, on the disease to be treated and on its severity.

The dosing of compounds according to the invention to achieve the desirable therapeutic effect depends on a number of factors, for example the specific compound chosen, the intended use, the mode of administration and the clinical condition of the patient. The daily dose is generally in the range from 0.3 mg to 100 mg (typically from 3 mg to 50 mg) per day and per kilogram of body weight, for example 3-10 mg/kg/day. An intravenous dose may be, for example, in the range from 0.3 mg to 1.0 mg/kg, which can suitably be administered as infusion of 10 ng to 100 ng per kilogram and per minute. Suitable infusion solutions for these purposes may contain, for example, 0.1 ng to 100 mg, typically 1 ng to 100 mg, per milliliter. Single doses may contain, for example, 1 mg to 10 g of the active ingredient. Thus, ampoules for injections may contain, for example, from 1 mg to 100 mg, and orally administrable single-dose formulations, for example tablets or capsules, may contain, for example, from 1.0 to 1000 mg, typically from 10 to 600 mg. For prevention and/or treatment of the abovementioned conditions, the compounds of the formula I themselves may be used as the compound, but they are preferably present with a compatible carrier in the form of a pharmaceutical composition. The carrier must, of course, be acceptable in the sense that it is compatible with the other ingredients of the composition and is not harmful for the patient's health. The carrier may be a solid or a liquid or both and is preferably formulated with the compound as a single dose, for example as a tablet, which may contain 0.05% to 95% by weight of the active ingredient. Other pharmaceutically active substances may likewise be present, including other compounds of formula I. The pharmaceutical compositions of the invention can be produced by one of the known pharmaceutical methods, which essentially consist of mixing the ingredients with pharmacologically acceptable carriers and/or excipients.

Another subject of the present invention are processes for the preparation of the compounds of the formula I and their salts and solvates, by which the compounds are obtainable and which are outlined in the following.

Abbreviations

Abbreviations within this document have their common meanings unless defined otherwise herein. An exemplary list of abbreviations used, can be found below.

| | |
|---|---|
| Ac | acetyl |
| amu | atomic mass unit |
| atm | atmosphere (pressure unit, 101325 Pa) |
| BSA | bovine serum albumin |
| cAMP | cyclic adenosine monophosphate |
| cat. | catalyst/catalyzed |
| CDI | carbonyl diimidazole |
| dba | dibenzylideneacetone |
| DCM | dichloromethane |
| DEAD | diethyl azodicarboxylate |
| DIAD | diisopropyl azodicarboxylate |
| DIPEA | diisopropyl-ethyl-amine |
| DMEM | Dulbecco's modified eagle medium |
| DMF | dimethylformamide |
| DMSO | dimethylsulfoxide |
| dppf | diphenylphosphinoferrocene |
| EA | ethyl acetate |

-continued

| | |
|---|---|
| EC<sub>50</sub> | concentration causing 50% of the maximal response |
| EDC | ethyl dimethylaminopropyl carbodiimide |
| ESI | electrospray ionisation |
| FA | formic acid |
| FCS | fetal calf serum |
| GPR119 | G-protein coupled receptor 119 |
| h | hour(s) |
| Hal | halogen (atom) |
| HATU | O-(7-azabenzotriazol-1-yl)-N,N,N',N'-tetramethyl-uronium hexafluorophosphate |
| HBSS | Hank's buffered salt solution |
| HEK 293 | human embryonic kidney 293 |
| HEPES | 4-(2-hydroxyethyl)-1-piperazineethanesulfonic acid |
| HOBt | 1-hydroxy-benzotriazole |
| HPLC | high pressure liquid chromatography |
| HTRF | homogenous time-resolved fluorescence |
| IBMX | 1-methyl-3-(2-methylpropyl)-7H-purine-2,6-dione |
| LCMS | liquid chromatography coupled mass spectroscopy |
| LG | leaving group |
| MeCN | methylcyanide (acetonitrile) |
| min | minute(s) |
| MS | mass spectroscopy |
| MTBE | methyl tert.-butyl ether |
| NMP | N-methyl pyrrolidin-2-one |
| NMR | nuclear magnetic resonance (spectrum) |
| PBS | phosphate buffered saline |
| PE | petroleum ether |
| PMBCl | para-methoxybenzyl chloride |
| R<sub>t</sub> | retention time |
| r.t. | room temperature |
| SGC | silica gel chromatography |
| SiO<sub>2</sub> | silica gel (for chromatography) |
| TFA | trifluoroacetic acid |
| THF | tetrahydrofuran |
| TM | transition metal |
| TMS | tetramethylsilane |
| Ts | para-tolylsulfonyl |
| UV | ultraviolet (spectrum) |

Synthetic Methods

Variables in the formulae of the schemes represent moieties as defined above unless other meanings are given.

Detailed descriptions of the Typical Procedures to which reference is made in this section can be found in the Examples section.

Compounds of the invention having the formula I may be prepared by combining known synthetic procedures. In a first method 3-hydroxy-pyrrolidin-2-one (A) (commercially available as racemic mixture and in both enantiomeric forms) is coupled with bicyclic aryl halides B (typically Hal is Br or I) to provide intermediates C. An example for suitable coupling conditions (CuI, N,N'-dimethyl-ethane-1,2-diamine, cesium carbonate) can be found in the Typical Procedure 1. Conversion of the hydroxy group in C to a suitable leaving group (LG is for example Br, I, OTs or OPPh$_3^+$) can be accomplished with various well known reagents (e.g. PPh$_3$/I$_2$, PPh$_3$/CBr$_4$, PPh$_3$/DIAD or TsCl/NEt$_3$) providing the intermediates D, which may be isolated or may be reacted without isolation with hydroxy-aryl building blocks of type E using an appropriate base (e.g. Na$_2$CO$_3$, K$_2$CO$_3$, Cs$_2$CO$_3$ or NaH). For example the conditions in the Typical Procedure 3 may be applied to couple intermediates C and E to provide compounds I.

A second method of synthesizing compounds I starts with a pyrrolidin-2-one substituted with a leaving group (LG) in 3-position (structures F), which may be prepared by reacting A with the reagents mentioned above. Other procedures for making structures F are known (e.g. base-promoted cyclization of 2,4-dibromo-butyramide). Intermediates F may be isolated or generated in situ to react with hydroxy-aryls E (typically in the presence of a base as described above) to provide intermediates G. As a final step, copper-catalyzed coupling with aryl halides B provides the desired compounds I (Scheme 1).

Scheme 1.

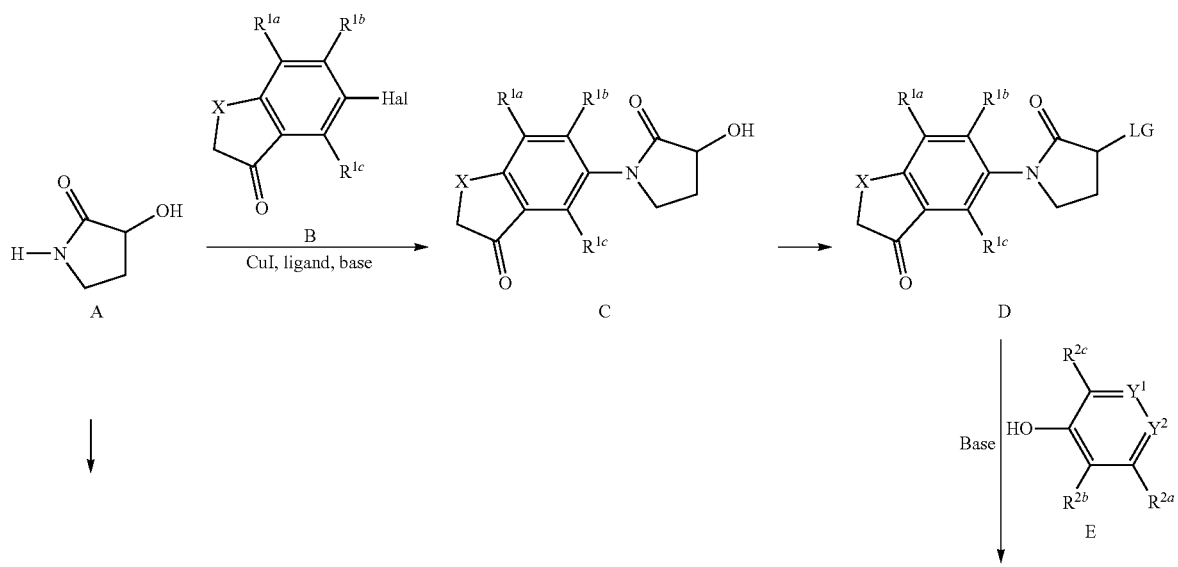

21 22

-continued

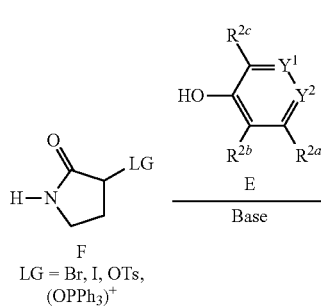 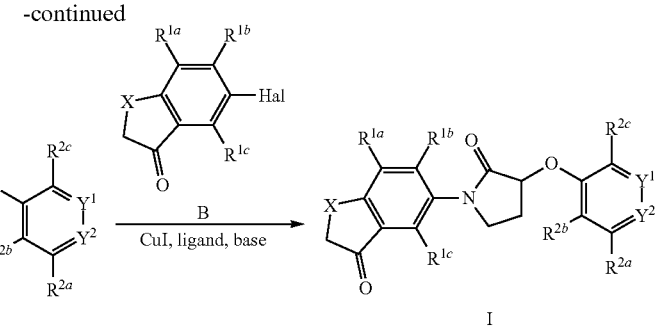

Aryl halides B (X=CH$_2$) may be prepared by Friedel-Crafts-cyclization of carbonyl chlorides derived from 3-(4-halo-phenyl)-propionic acids, which may eventually be further substituted at the positions of R$^{1a}$, R$^{1b}$ and R$^{1c}$.

Another method of synthesizing compounds I uses aryl bromides of structure H as starting points. Structures H may be obtained by the methods described above. For example an aryl halide B (R$^{1a}$=Br) may be coupled to a pyrrolidinone of type G. Further elaboration of structures H may be done by transition metal catalyzed reactions, which replace the bromo atom by other substituents like other halide, cyano or alkyl groups. Illustrative examples for such reactions can be found in Scheme 2a.

Scheme 2a.

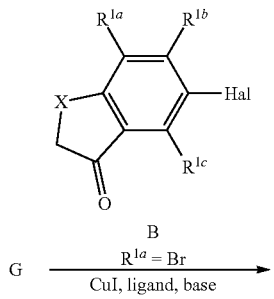

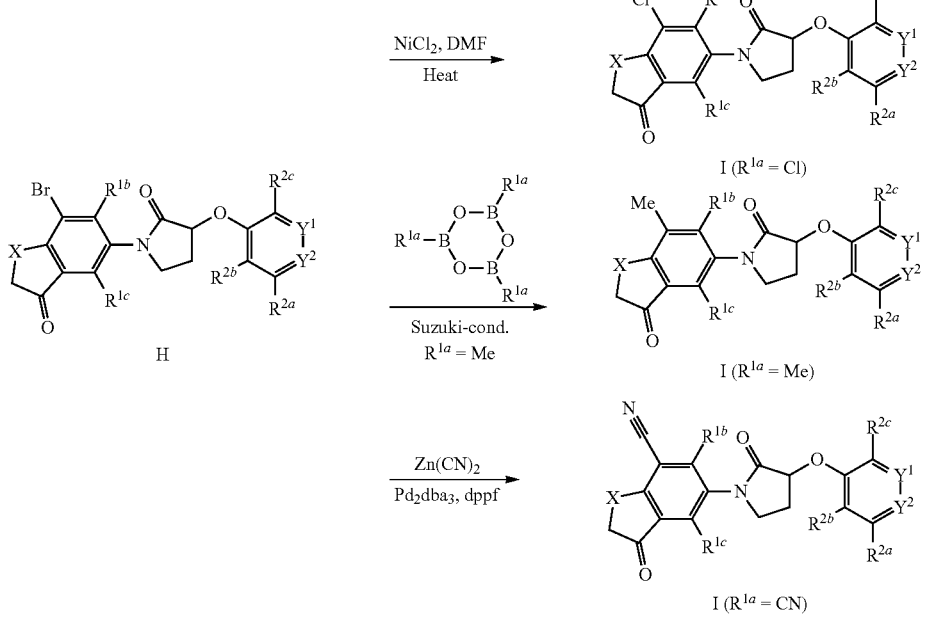

A similar approach to another variety of compounds I is depicted in Scheme 2b.

Scheme 2b.

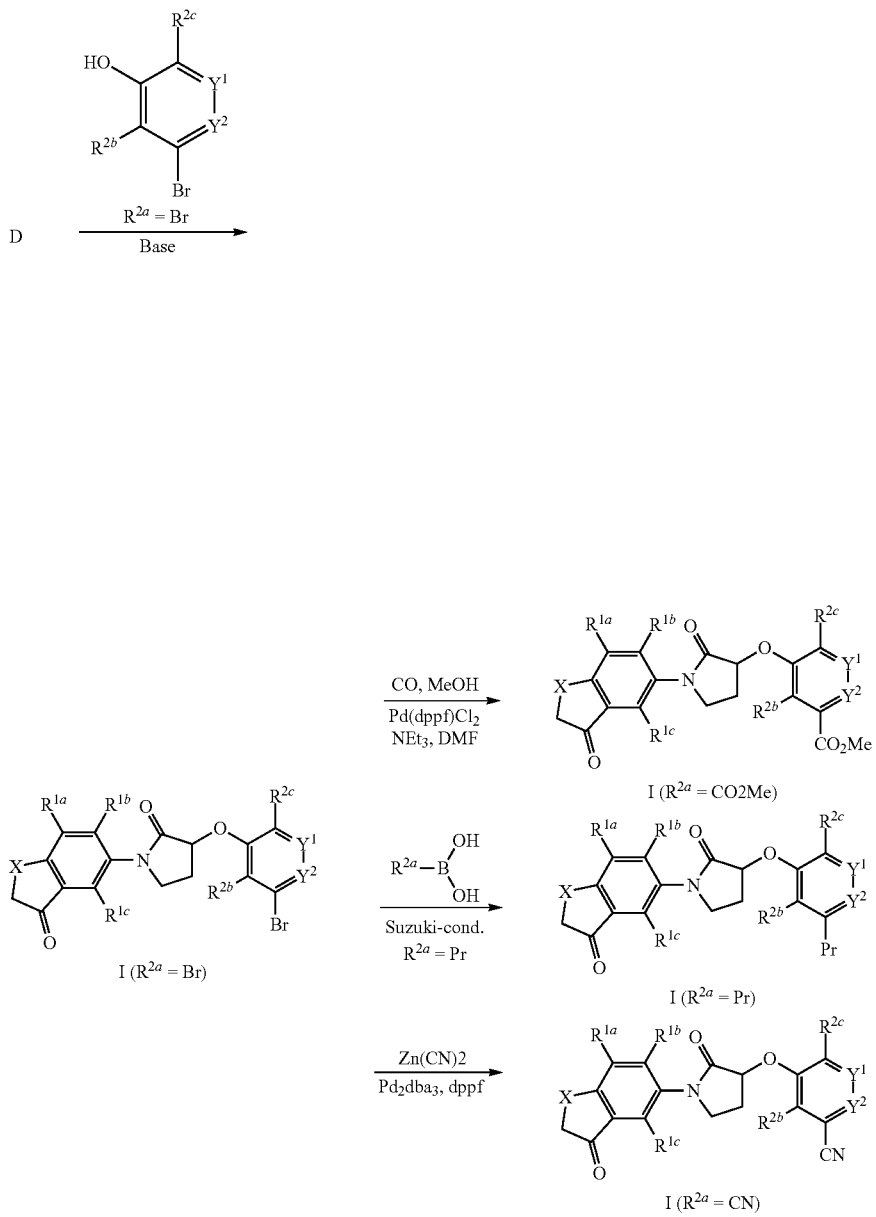

Certain compounds I ($Y^1$=N, $Y^2$=Z—$R^3$—$R^4$, Z=O, S) may be prepared by coupling aryl halides B with hydroxy-pyridines E ($Y^1$=N, $Y^2$=Z—$R^3$—$R^4$, Z=O, S). Said hydroxy-pyridines E may be prepared by displacement of a halide (F, Cl, Br or I) in the 2-position of 5-bromo-2-halo-pyridines, which are substituted with $R^{2a}$, $R^{2b}$ and $R^{2c}$, using nucleophiles of the type HZ—$R^3$—$R^4$ (Z=O, S) followed by conversion of the 5-bromo-substituent to a hydroxy group (e.g. by oxidation of a boronate group introduced by palladium catalyzed coupling with bis-pinacolato-diboron). See Typical Procedure 6 for conditions for the nucleophilic displacement reaction, Typical Procedures 5 and 5a for examples of boronate-oxidation conditions, Typical Procedure 4 for an example of conditions to install a boronate group and Scheme 3 for illustration of the overall method. A benzyl group ($R^3$—$R^4$=CH$_2$—Ph) in compounds I ($Y^1$=N, $Y^2$=Z—$R^3$—$R^4$, Z=O, S) may be cleaved for example by hydrogenolysis (for example following Typical Procedure 7) to provide intermediates J, which may be alkylated by LG-$R^{3'}$—$R^{4'}$, $R^{3'}$ and $R^{4'}$ being defined like $R^3$ and $R^4$ respectively, to yield compounds I ($Y^1$=N, $Y^2$=Z=O, S).

For example, the structure J may be a 2-hydroxy-pyridine (Z=O), which may be alkylated under Mitsunobu-conditions (PPh$_3$/DIAD; see for example Typical Procedure 3) starting with alcohols HO—$R^{3'}$—$R^{4'}$. Triphenylphosphine may be introduced into the reaction as polymer. DIAD may be replaced by other azodicarboxylates (e.g. DEAD).

Scheme 3.

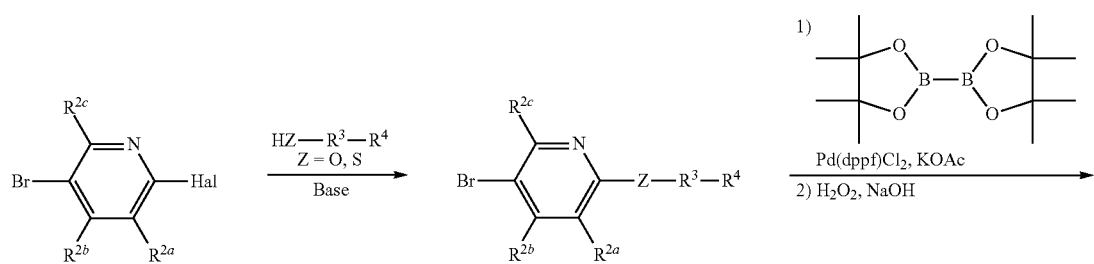

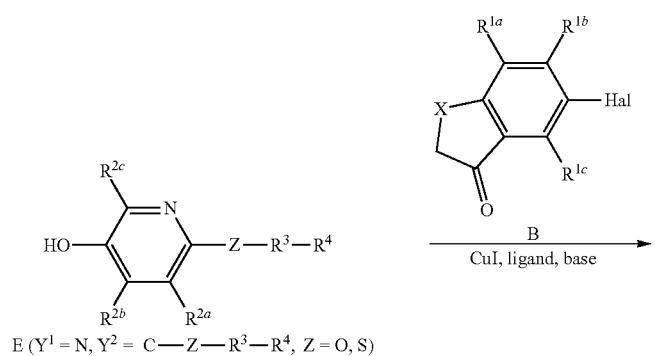

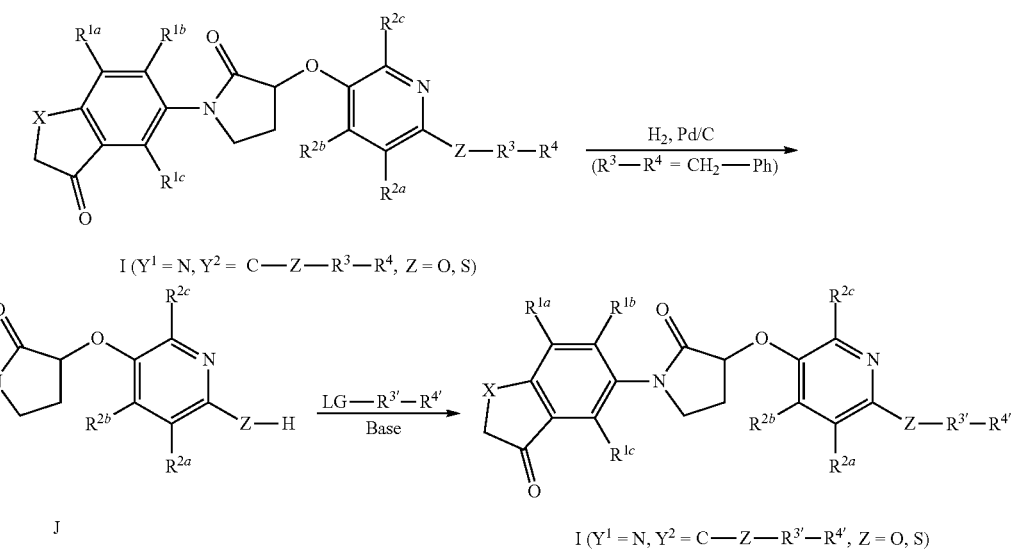

Certain other compounds of the invention may be prepared by reaction of hydroxy-pyrrolidinones C with bromo-pyridinols and subsequent transition metal catalyzed replacement of the Br-atom by Z—$R^3$—$R^4$. For example 2-bromo-pyridin-4-ol (substituted with $R^{2a}$, $R^{2b}$ and $R^{2c}$) may be used followed by transition metal catalyzed alkoxylation to prepare compounds I ($Y^1$=C—O—$R^3$—$R^4$, $Y^2$=N). See for example Typical Procedure 10 for conditions of palladium catalyzed alkoxylations and Scheme 4 for illustration of the overall method.

Scheme 4.

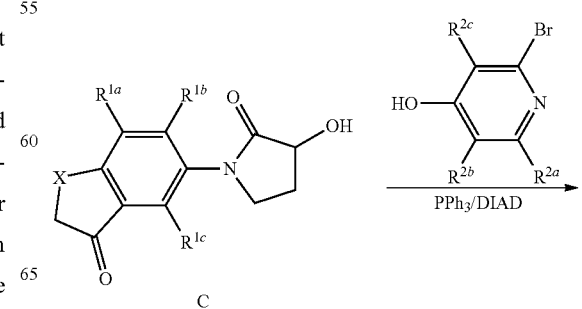

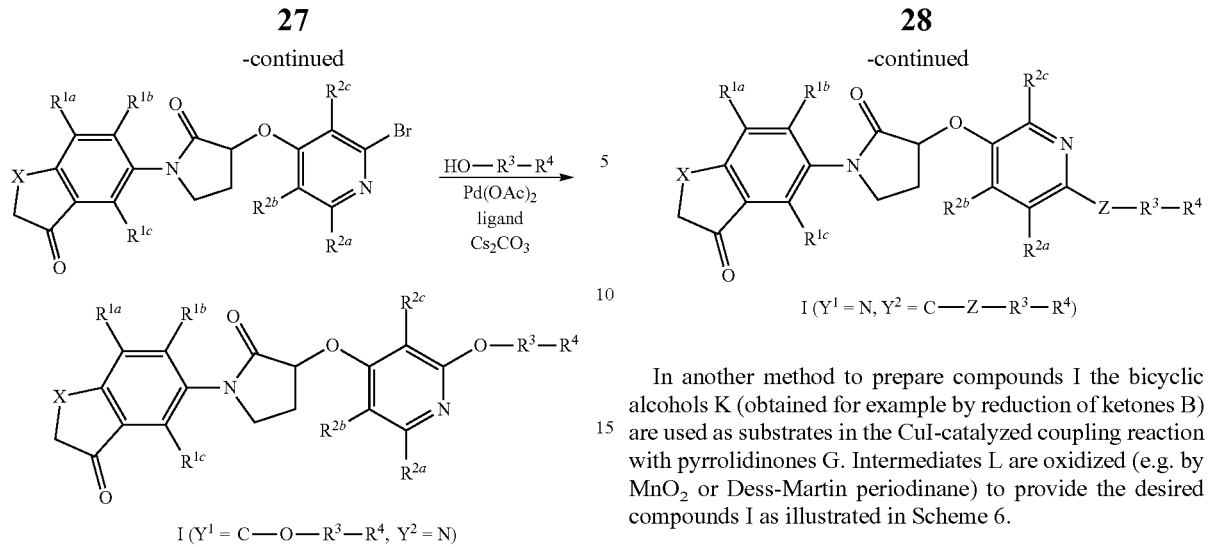

Variation of the order of the steps in the synthetic sequence provides further methods to prepare compounds I. For example intermediates F may be reacted with 6-bromo-pyridin-3-ols and subsequently the bromo-substituent may be exchanged for Z—R³—R⁴ (see Typical Procedure 8 for an example of bromide displacement with sulfur nucleophiles) to provide intermediates G (Y¹=N, Y²=Z—R³—R⁴) In a last step coupling with aryl halides B again provides compounds I (Y¹=N, Y²=Z—R³—R⁴) as illustrated in Scheme 5.

Scheme 5.

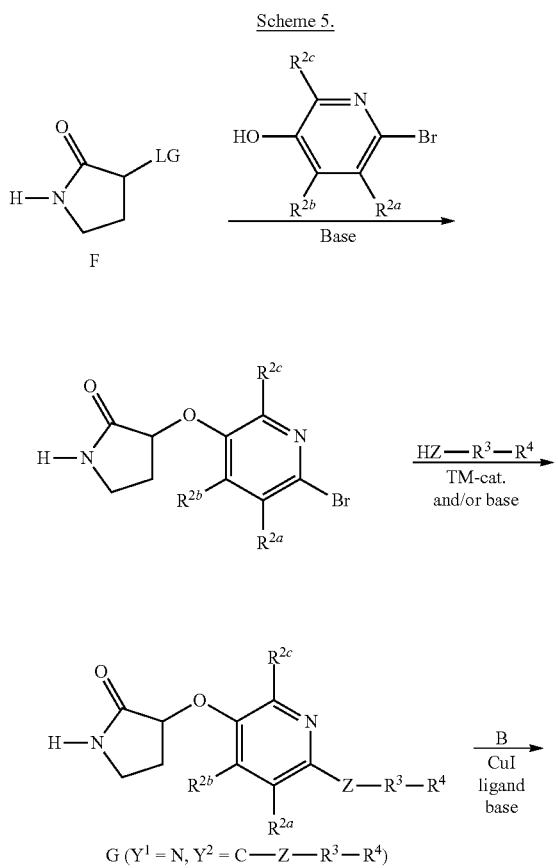

In another method to prepare compounds I the bicyclic alcohols K (obtained for example by reduction of ketones B) are used as substrates in the CuI-catalyzed coupling reaction with pyrrolidinones G. Intermediates L are oxidized (e.g. by MnO₂ or Dess-Martin periodinane) to provide the desired compounds I as illustrated in Scheme 6.

Scheme 6.

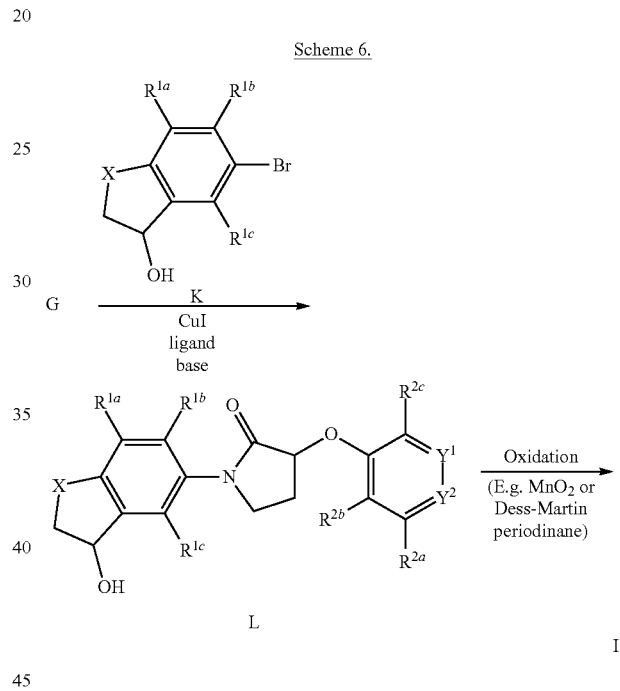

Analytical Methods

Examples were characterized by standard analytical methods. This includes at least two methods (e.g. selected from HPLC, MS, ¹H-NMR). In particular, MS and HPLC data were obtained by combined analytical HPLC/MS (LCMS). For example the following LCMS methods were used.

Method A

Column: Waters UPLC BEH C18 2.1*50 mm, 1.7 μm, mobile phase: (H₂O+0.05% FA):(MeCN+0.035% FA) 95:5 (0 min) to 5:95 (1.1 min) to 5:95 (1.7 min) to 95:5 (1.8 min) to 95:5 (2 min), flow rate: 0.9 mL/min, temperature: 55° C.; ionization method: ES⁺; UV wavelength: 220 nm.

Method B

Column: Waters UPLC BEH C18 2.1*50 mm, 1.7 pm, mobile phase: (H₂O+0.05% FA):(MeCN+0.035% FA) 98:2 (0 min) to 5:95 (2 min) to 5:95 (2.6 min) to 95:5 (2.7 min) to 95:5 (3 min), flow rate: 0.9 mL/min, column temperature: 55° C.; ionization method: ES⁺; UV wavelength: 220 nm.

Method C

Column: Waters UPLC BEH C18 2.1*50 mm; 1.7 pm, mobile phase: (H₂O+0.1% FA):(MeCN+0.08% FA) 95:5 (0 min) to 5:95 (1.1 min) to 5:95 (1.7 min) to 95:5 (1.8 min) to 95:5 (2 min), flow rate: 0.9 mL/min, column temperature: 55° C.; ionization method: ES$^+$, UV wavelength: 220 nm.

Method D

Column: Waters XBridge C18 4.6*50 mm, 2.5 pm, mobile phase: (H$_2$O+0.1% FA):(MeCN+0.1% FA) 97:3 (0 min) to 40:60 (3.5 min) to 2:98 (4 min) to 2:98 (5 min) to 97:3 (5.2 min) to 97:3 (6.5 min), flow rate: 0.9 mL/min, column temperature: 55° C.; ionization method: ES$^+$; UV wavelength: 220 nm.

In general, HPLC data is represented by the retention time (R$_t$; in min); MS data is given as the observed mass number (m/z) of the ion [M+H]$^+$ (if present) and $^1$H-NMR data is reported by lists of chemical shifts δ (in ppm vs. TMS) of the observed signals (the number of hydrogen atoms was determined using the area under the respective signal; signal multiplicity is characterized as follows: s=singlet, d=doublet, dd=doublet of doublets, t=triplet, dt=doublet of triplets, q=quartet, m=multiplet, br=broad; coupling constants J are given in Hertz (Hz)). Deuterated solvents were used for NMR spectroscopy.

EXAMPLES

The following examples are particular embodiments of the invention. They partially illustrate the scope of the invention without limiting it.

Abbreviations and chemical symbols have their usual and customary meanings unless otherwise indicated.

The examples were prepared, isolated and analyzed by the procedures and methods given. Alternatively they may be prepared by the general synthetic methods detailed above. Further variations of the synthetic procedures may be proposed by a person skilled in the art.

When example compounds containing a basic group were purified by preparative HPLC on reversed phase column material and, as customary, the eluent was a gradient mixture of water and acetonitrile containing trifluoroacetic acid (TFA), they were obtained in part in the form of their addition salt with TFA, depending on the details of the workup such as evaporation or lyophilization conditions. In the names of the example compounds and their structural formulae any such TFA present is not specified.

Preparation of Examples 1

Example 1-01 (Typical Procedure 1)

To a solution of 6-bromo-indan-1-one (70 mg) and 3-[4-(3-methyl-butoxy)-phenoxy]-pyrrolidin-2-one (70 mg) in 1,4-dioxane (2 mL) was added N,N'-dimethyl-ethane-1,2-diamine (0.325 mL) and cesium carbonate (141 mg). The mixture was purged for 5 minutes with a flow of argon and CuI (3.2 mg) was added. The mixture was heated at 100° C. for 1 hour. After cooling to r.t. insoluble material was removed by filtration and the filtrate concentrated. The residue was purified by preparative HPLC to provide example 1-01.

Following the Typical Procedure 1, the Examples 1 in Table 1 were prepared using the respective aryl bromides and 3-substituted pyrrolidinones.

TABLE 1

| Example | Structure | LCMS Method | R$_t$ [min] | ESI$^+$ m/z [amu] |
|---|---|---|---|---|
| 1-01 | 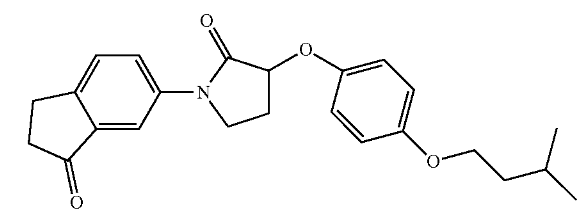 [SMILES: CC(C)CCOc1ccc(OC2CCN(c3ccc4c(c3)C(=O)CC4)C2=O)cc1] | C | 1.24 | 394.2 |
| 1-02 | 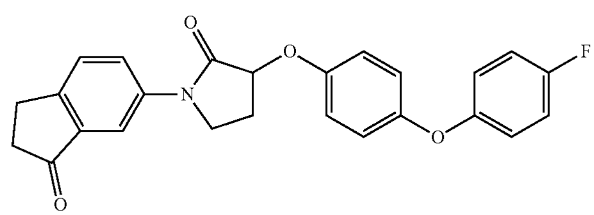 [SMILES: O=C1CCc2ccc(N3CCC(Oc4ccc(Oc5ccc(F)cc5)cc4)C3=O)cc21] | C | 1.34 | 418.2 |
| 1-03 | 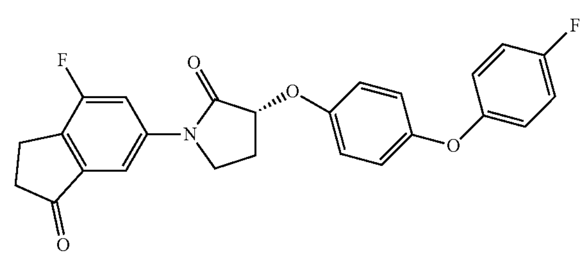 [SMILES: O=C1CCc2c(F)cc(N3CC[C@@H](Oc4ccc(Oc5ccc(F)cc5)cc4)C3=O)cc21] | A | 1.23 | 436.2 |

TABLE 1-continued
| Example | Structure | LCMS Method | R$_t$ [min] | ESI$^+$ m/z [amu] |
|---|---|---|---|---|
| 1-04 | 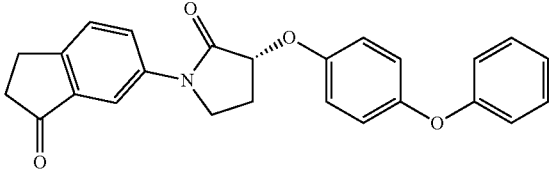 [SMILES: O=C1CCc2ccc(N3CC[C@@H](Oc4ccc(Oc5ccccc5)cc4)C3=O)cc21] | C | 1.34 | 400.2 |
| 1-05 | 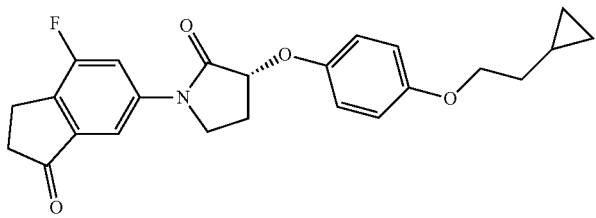 [SMILES: O=C1CCc2c(F)cc(N3CC[C@@H](Oc4ccc(OCCC5CC5)cc4)C3=O)cc21] | B | 1.96 | 410.3 |
| 1-06 | 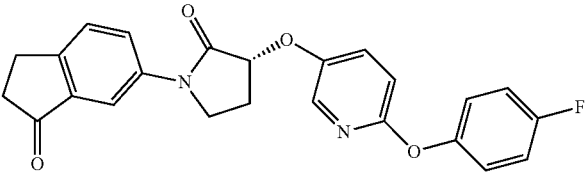 [SMILES: O=C1CCc2ccc(N3CC[C@@H](Oc4ccc(Oc5ccc(F)cc5)nc4)C3=O)cc21] | B | 1.78 | 419.2 |
| 1-07 | 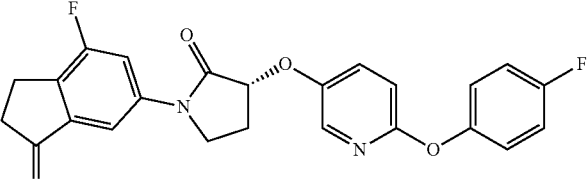 | B | 1.85 | 437.2 |
| 1-08 | 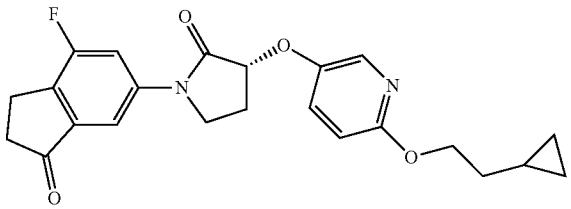 [SMILES: O=C1CCc2c(F)cc(N3CC[C@@H](Oc4ccc(OCCC5CC5)nc4)C3=O)cc21] | D | 4.79 | 411.3 |
| 1-09 | 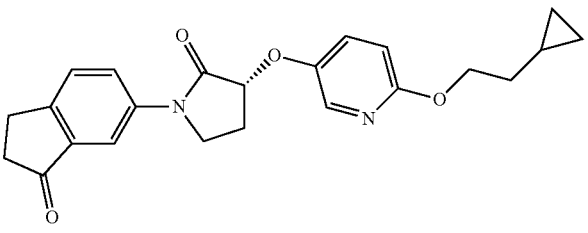 [SMILES: O=C1CCc2ccc(N3CC[C@@H](Oc4ccc(OCCC5CC5)nc4)C3=O)cc21] | B | 1.84 | 393.2 |
| 1-10 | 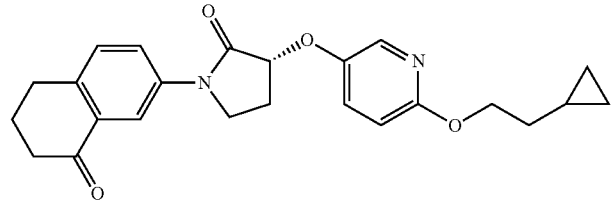 [SMILES: O=C1CCCc2ccc(N3CC[C@@H](Oc4ccc(OCCC5CC5)nc4)C3=O)cc21] | B | 1.88 | 407.3 |

TABLE 1-continued

| Example | Structure | LCMS Method | R$_t$ [min] | ESI$^+$ m/z [amu] |
|---|---|---|---|---|
| 1-11 | 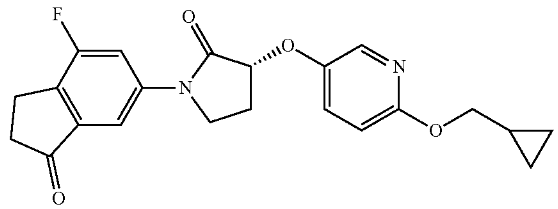 [SMILES: O=C1CCc2c(F)cc(N3CC[C@@H](Oc4ccc(OCC5CC5)nc4)C3=O)cc21] | B | 1.80 | 397.2 |
| 1-12 | 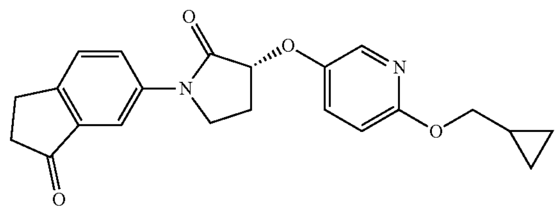 [SMILES: O=C1CCc2ccc(N3CC[C@@H](Oc4ccc(OCC5CC5)nc4)C3=O)cc21] | D | 4.37 | 379.3 |
| 1-13 | 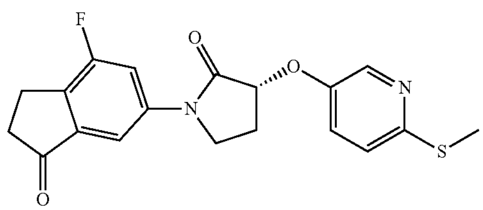 [SMILES: CSc1ccc(O[C@@H]2CCN(c3cc(F)c4c(c3)C(=O)CC4)C2=O)cn1] | B | 1.69 | 373.2 |
| 1-14 | 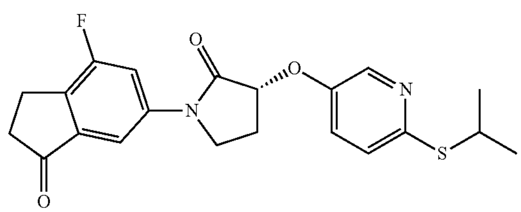 [SMILES: CC(C)Sc1ccc(O[C@@H]2CCN(c3cc(F)c4c(c3)C(=O)CC4)C2=O)cn1] | B | 1.85 | 401.2 |
| 1-15 | 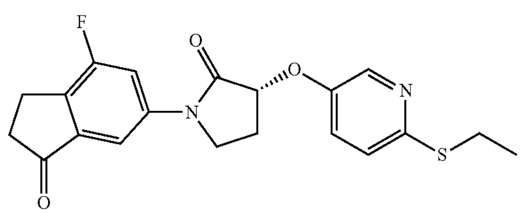 [SMILES: CCSc1ccc(O[C@@H]2CCN(c3cc(F)c4c(c3)C(=O)CC4)C2=O)cn1] | D | 4.52 | 387.2 |
| 1-16 | 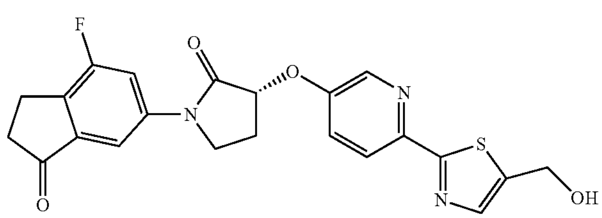 [SMILES: O=C1CCc2c(F)cc(N3CC[C@@H](Oc4ccc(-c5ncc(CO)s5)nc4)C3=O)cc21] | D | 3.61 | 440.1 |
| 1-17 | 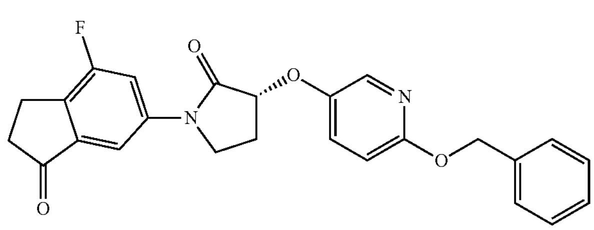 [SMILES: O=C1CCc2c(F)cc(N3CC[C@@H](Oc4ccc(OCc5ccccc5)nc4)C3=O)cc21] | B | 1.87 | 433.2 |

TABLE 1-continued

| Example | Structure | LCMS Method | R$_t$ [min] | ESI$^+$ m/z [amu] |
|---|---|---|---|---|
| 1-18 | 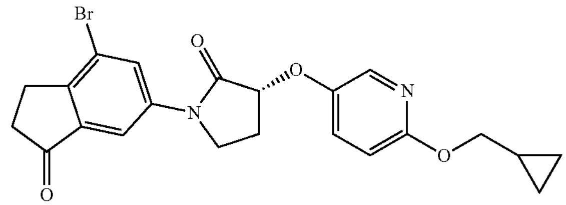 [SMILES: O=C1CCc2c(Br)cc(N3CC[C@@H](Oc4ccc(OCC5CC5)nc4)C3=O)cc21] | B | 1.90 | 457.1 |
| 1-19 | 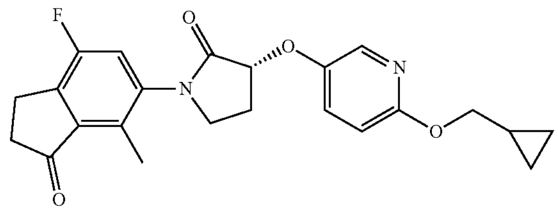 [SMILES: Cc1c(N2CC[C@@H](Oc3ccc(OCC4CC4)nc3)C2=O)cc(F)c2c1C(=O)CC2] | B | 1.76 | 411.2 |
| 1-20 | 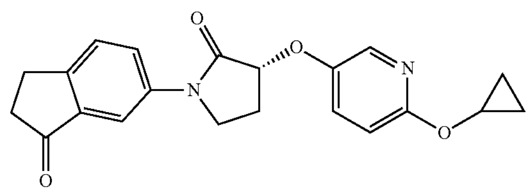 [SMILES: O=C1CCc2ccc(N3CC[C@@H](Oc4ccc(OC5CC5)nc4)C3=O)cc21] | B | 1.62 | 365.2 |

Alternative Preparation of (R)-3-[6-(2-Cyclopropyl-ethoxy)-pyridin-3-yloxy]-1-(7-fluoro-3-oxo-indan-5-yl)-pyrrolidin-2-one (Example 1-08)

A mixture of (R)-3-[6-(2-cyclopropyl-ethoxy)-pyridin-3-yloxy]-pyrrolidin-2-one (100 mg), 6-bromo-4-fluoro-2,3-dihydro-1H-inden-1-one (87 mg) and 1,4-dioxane (2 mL) was purged with argon. N,N'-Dimethyl-ethylene-diamine (336 mg), cesium carbonate (248 mg) and copper(I) iodide (7 mg) were added. The mixture was heated to 85° C. for 3 hours. After cooling to r.t. the mixture was filtered and the filtrate purified by preparative HPLC to provide Example 1-08. $^1$H-NMR (400 MHz, DMSO) 67.99 (1H, dd, J=11.3, 1.8 Hz), 7.97 (1H, d, J=3.1 Hz), 7.77 (1H, d, J=1.8 Hz), 7.53 (1H, dd, J=9.0, 3.1 Hz), 6.77 (1H, d, J=9.0 Hz), 5.22 (1H, dd, J=8.3, 8.3 Hz), 4.24 (2H, t, J=6.8 Hz), 3.96 (1H, m), 3.86 (1H, m), 3.10 (2H, m), 2.72 (2H, m), 2.69 (1H, m), 2.14 (1H, m), 1.60 (2H, dt, J=6.8, 6.8 Hz), 0.80 (1H, m), 0.42 (2H, m), 0.10 (2H, m).

Alternative Preparation of (R)-3-(6-Cyclopropyl-methoxy-pyridin-3-yloxy)-1-(7-fluoro-3-oxo-indan-5-yl)-pyrrolidin-2-one (Example 1-11)

A mixture of (R)-3-[6-(2-cyclopropyl-methoxy)-pyridin-3-yloxy]-pyrrolidin-2-one (100 mg), 6-bromo-4-fluoro-2,3-dihydro-1H-inden-1-one (92 mg) and 1,4-dioxane (2 mL) was purged with argon. N,N'-Dimethyl-ethylene-diamine (355 mg), cesium carbonate (263 mg) and copper(I) iodide (8 mg) were added. The mixture was heated to 80° C. for 4 hours. After cooling to r.t. the mixture was filtered and the filtrate purified by preparative HPLC to provide Example 1-11. $^1$H-NMR (400 MHz, DMSO) δ 7.99 (1H, dd, J=11.2, 1.8 Hz), 7.95 (1H, d, J=3.1 Hz), 7.77 (1H, d, J=1.8 Hz), 7.53 (1H, dd, J=9.0, 3.1 Hz), 6.79 (1H, d, J=9.0 Hz), 5.22 (1H, dd, J=8.3, 8.3 Hz), 4.03 (2H, d, J=7.1 Hz), 3.96 (1H, m), 3.86 (1H, m), 3.10 (2H, m), 2.72 (2H, m), 2.68 (1H, m), 2.13 (1H, m), 1.22 (1H, m), 0.54 (2H, m), 0.30 (2H, m).

Preparation of 3-Substituted Pyrrolidin-2-ones

3-[4-(3-Methyl-butoxy)-phenoxy]-pyrrolidin-2-one (Typical Procedure 2) A mixture of NaH (1.07 g) and THF (30 mL) was added 2,4-dibromo-butyramide (3.0 g) at 0° C. After 3 hours 4-(3-methyl-butoxy)-phenol (3.3 g) was added and the mixture heated to 65° C. for 4 hours. After standing at room temperature for 12 hours, water was added and the mixture was extracted with MTBE. The organic phase was washed twice (2 N NaOH), dried (Na$_2$SO$_4$) and concentrated to provide the title compound. MS ESI$^+$: m/z=264 [M+H]$^+$.

4-(3-Methyl-butoxy)-phenol

A mixture of benzene-1,4-diol (20.0 g), DMF (100 mL), cesium carbonate (59.2 g) and 1-bromo-3-methyl-butane (13.7 g) was heated to 60° C. for 12 hours. After the mixture reached room temperature, it was distributed between water and EA. The organic phase was washed twice (water), dried (Na$_2$SO$_4$) and concentrated. The residue was purified by chromatography (SiO$_2$; EA/heptane 1:2) to provide the subtitle compound.

MS ESI$^+$: m/z=181 [M+H]$^+$.

3-[4-(4-Fluoro-phenoxy)-phenoxy]-pyrrolidin-2-one

Typical Procedure 2 was followed. Reaction of 2,4-dibromo-butyramide with NaH and 4-(4-fluoro-phenoxy)-phenol provided the title compound. MS ESI$^+$: m/z=288 [M+H]$^+$.

(R)-3-[6-(4-Fluoro-phenoxy)-pyridin-3-yloxy]-pyrrolidin-2-one (Typical Procedure 3)

A mixture of THF (200 mL) and DCM (100 mL) under argon was added triphenylphosphine (polymer, 1.8 mmol/g, 20 g). Diisopropylazodicarboxylate (8.87 g) was added. After 5 minutes (S)-3-hydroxy-pyrrolidin-2-one (3.1 g) and 6-(4-fluoro-phenoxy)-pyridin-3-ol (6.0 g) were added. After 30 minutes the mixture was filtered and the filtrate concentrated. The residue was purified by chromatography ($SiO_2$; DCM/ MeOH 15:1) to provide the title compound. MS ESI$^+$: m/z=289 [M+H]$^+$.

6-(4-Fluoro-phenoxy)-pyridin-3-ol

A mixture of 6-bromo-pyridin-3-ol (8.0 g), 4-fluorophenol (15.5 g) and cesium carbonate (30 g) was heated to 170° C. for 6 hours. After the mixture reached room temperature, it was distributed between water and MTBE. The organic phase was dried ($Na_2SO_4$) and concentrated. The residue was purified by chromatography ($SiO_2$; EA/heptane 1:1.5) to provide the subtitle compound. MS ESI$^+$: m/z=206 [M+H]$^+$.

(R)-3-[4-(4-Fluoro-phenoxy)-phenoxy]-pyrrolidin-2-one

Typical Procedure 3 was followed. Reaction of (S)-3-hydroxy-pyrrolidin-2-one with 4-(4-fluoro-phenoxy)-phenol provided the title compound. MS ESI$^+$: m/z=288 [M+H]$^+$.

(R)-3-[4-(Phenoxy)-phenoxy]-pyrrolidi n-2-one

Typical Procedure 3 was followed. Reaction of (S)-3-hydroxy-pyrrolidin-2-one with 4-(phenoxy)-phenol provided the title compound. MS ESI$^+$: m/z=270 [M+H]$^+$.

(R)-3-[6-(2-Cyclopropyl-ethoxy)-pyridin-3-yloxy]-pyrrolidin-2-one

A mixture of (S)-3-hydroxy-pyrrolidin-2-one (0.79 g), 6-(2-cyclopropyl-ethoxy)-pyridin-3-ol (1.4 g), triphenylphosphine (2.25 g), DCM (30 mL) and THF (20 mL) was added DIAD (1.74 g). After 2 days the mixture was filtered and the filtrate was evaporated. The residue was purified by SGC (eluent: EA/MeOH 9:1) to provide the title compound. MS ESI$^+$: m/z=263 [M+H]$^+$.

6-(2-Cyclopropyl-ethoxy)-pyridin-3-ol (Typical Procedure 4)

A mixture of 5-bromo-2-(2-cyclopropyl-ethoxy)-pyridine (2.2 g), bis(pinacolato)diboron (2.54 g) and 1,4-dioxane (15 mL) was purged with argon. Potassium acetate (2.68 g) and Pd(dppf)$Cl_2$ (0.35 g) were added. The mixture was irradiated in a microwave instrument for 1 hour at 80° C. After the mixture reached room temperature, it was distributed between water and EA. The organic phase was dried ($Na_2SO_4$) and concentrated to obtain the crude boronate.
Typical Procedure 5
The crude boronate from above was dissolved in THF (50 mL) and NaOH (40% in water, 10 mL) and $H_2O_2$ (30% in water, 3 mL) were added. After 3 hours the mixture was neutralized and extracted with EA. The organic phase was dried ($Na_2SO_4$) and concentrated to provide the subtitle compound. MS ESI$^+$: m/z=180 [M+H]$^+$.

5-Bromo-2-(2-cyclopropyl-ethoxy)-pyridine (Typical Procedure 6)

A mixture of 2-cyclopropyl-ethanol (4.1 g) and DMF (15 mL) under argon was treated with NaH (60% in oil, 0.45 g). After 4 hours 5-bromo-2-fluoro-pyridine (3.0 g) was added at 0° C. After 4 hours at room temperature, the mixture was distributed between water and EA. The organic phase was washed twice (water), dried ($Na_2SO_4$) and concentrated. The residue was purified by chromatography ($SiO_2$; EA/heptane 1:4) to provide the subtitle compound. MS ESI$^+$: m/z=242 [M+H]$^+$.

(R)-3-[6-(2-Cyclopropyl-methoxy)-pyridin-3-yloxy]-pyrrolidin-2-one

A mixture of (S)-3-hydroxy-pyrrolidin-2-one (3.00 g), 6-(2-cyclopropyl-methoxy)-pyridin-3-ol (4.90 g), triphenylphosphine (polymer, 8.56 g), DCM (30 mL) and THF (50 mL) was added DIAD (6.60 g) keeping the reaction temperature below 30° C. After 12 hours the mixture was filtered and the filtrate was evaporated. The residue was purified by SGC (eluent: EA/MeOH 9:1) to provide the title compound. MS ESI$^+$: m/z=249 [M+H]$^+$.

6-Cyclopropylmethoxy-pyridin-3-ol

A mixture of 5-bromo-2-cyclopropylmethoxy-pyridine (8.00 g), bis(pinacolato)diboron (8.91 g) and 1,4-dioxane (53 mL) was purged with argon. Potassium acetate (3.44 g) and Pd(dppf)$Cl_2$ (2.57 g) were added and the mixture heated to 100° C. for 1 hour by microwave irradiation. The mixture was filtered and the filtrate diluted with EA, washed with water, dried ($Na_2SO_4$) and concentrated. The residue was purified by SGC (eluent: EA/heptane 1:6) to provide the crude boronate. MS ESI$^+$: m/z=276 [M+H]$^+$. The boronate was dissolved in THF (60 mL). Aqueous NaOH (5 M) was added at 0° C. Hydrogenperoxide (30% in water, 30 mL) was added slowly. The mixture was allowed to warm to r.t. and stirred for 4 hours. The mixture was extracted with MTBE. The aqueous phase was adjusted to pH 3-4 by addition of diluted HCl and extracted with EA. The organic phase was dried ($Na_2SO_4$) and concentrated to provide the subtitle compound. MS ESI$^+$: m/z=166 [M+H]$^+$.

5-Bromo-2-cyclopropylmethoxy-pyridine

To a mixture of 2-cyclopropyl-methanol (6.15 g) and DMF (12 mL) was added NaH (60% in mineral oil, 1.5 g) at 0° C. After stirring for 4 hours at r.t. the mixture was diluted with DMF (5 mL) and 5-bromo-2-fluoro-pyridine (6.00 g) was slowly added keeping the reaction temperature below 30° C. After 30 minutes at r.t. the mixture was heated to 130° C. for 1 hour by microwave irradiation. After cooling to r.t. the mixture was diluted with EA and washed with water (3 times). The organic phase was dried ($Na_2SO_4$) and concentrated. The residue was purified by SGC to provide the subtitle compound. MS ESI$^+$: m/z=228 [M+H]$^+$.

(R)-3-[6-(2-Cyclopropoxy)-pyridin-3-yloxy]-pyrrolidin-2-one

Typical Procedure 3 was followed. Reaction of 6-cyclopropoxy-pyridin-3-ol and (S)-3-hydroxy-pyrrolidin-2-one provided the title compound. MS ESI$^+$: m/z=235 [M+H]$^+$.

6-Cyclopropoxy-pyridin-3-ol

A mixture of 5-bromo-2-cyclopropoxypyridine (Milestone Pharmtech, 500 mg) in THF (10 mL) was cooled (−78° C.) and n-BuLi (2.5 M in toluene, 1.49 mL) was added dropwise within 10 minutes. After 20 minutes trimethylborate (429 µL) was added. After 2 hours peracetic acid (32% in AcOH, 786 µL) was added dropwise. After 10 minutes the reaction temperature was changed to 0° C. After 1 hour the mixture was poured into aqueous NaHSO$_3$-solution (5%, 5 mL). The mixture was extracted with EA. The organic phase was dried (Na$_2$SO$_4$), filtered and concentrated. The residue was purified by chromatography (silica gel, heptane to EA/heptane 2:3) to provide the subtitle compound. MS ESI$^+$: m/z=152 [M+H]$^+$.

(R)-3-(6-Benzyloxy-pyridin-3-yloxy)-pyrrolidin-2-one

Following the sequence described for (R)-3-[6-(2-cyclopropyl-ethoxy)-pyridin-3-yloxy]-pyrrolidin-2-one, the title compound was prepared from phenyl-methanol, 5-bromo-2-fluoro-pyridine and (S)-3-hydroxy-pyrrolidin-2-one. MS ESI$^+$: m/z=285 [M+H]$^+$.

(R)-3-[4-(2-Cyclopropyl-ethoxy)-phenoxy]-pyrrolidin-2-one

Typical Procedure 3 was followed. Reaction of (R)-3-(4-hydroxy-phenoxy)-pyrrolidin-2-one with 2-cyclopropyl-ethanol provided the title compound. MS ESI$^+$: m/z=262 [M+H]$^+$.

(R)-3-(4-Hydroxy-phenoxy)-pyrrolidin-2-one (Typical Procedure 7)

A mixture of (R)-3-(4-benzyloxy-phenoxy)-pyrrolidin-2-one (61 g), MeOH/DCM (2:1, 2 L) and Pd (10% on carbon, 6 g) was shaken under an atmosphere of hydrogen for 20 hours. The catalyst was removed by filtration and the filtrate concentrated to provide the subtitle compound. MS ESI$^+$: m/z=194 [M+H]$^+$.

(R)-3-(4-Benzyloxy-phenoxy)-pyrrolidin-2-one

Typical Procedure 3 was followed. Reaction of (S)-3-hydroxy-pyrrolidin-2-one with 4-benzyloxy-phenol provided the subtitle compound. MS ESI$^+$: m/z=284 [M+H]$^+$.

(R)-3-(6-Methylsulfanyl-pyridin-3-yloxy)-pyrrolidin-2-one (Typical Procedure 8)

A mixture of (R)-3-(6-bromo-pyridin-3-yloxy)-pyrrolidin-2-one (0.8 g), sodium methanethiolate (327 mg) and DMF (15 mL) was heated to 100° C. for 15 minutes. After the mixture reached room temperature, it was distributed between water and EA. The organic phase was dried (Na$_2$SO$_4$) and concentrated. The residue was purified by preparative HPLC to provide the title compound. MS ESI$^+$: m/z=225 [M+H]$^+$.

(R)-3-(6-Bromo-pyridin-3-yloxy)-pyrrolidin-2-one

Typical Procedure 3 was followed. Reaction of (S)-3-hydroxy-pyrrolidin-2-one with 6-bromo-pyridin-3-ol provided the subtitle compound. MS ESI$^+$: m/z=257 [M+H]$^+$.

(R)-3-(6-Ethylsulfanyl-pyridin-3-yloxy)-pyrrolidin-2-one

Typical Procedure 8 was followed. Reaction of (R)-3-(6-bromo-pyridin-3-yloxy)-pyrrolidin-2-one with lithium ethanethiolate provided the title compound. MS ESI$^+$: m/z=239 [M+H]$^+$.

(R)-3-(6-Isopropylsulfanyl-pyridin-3-yloxy)-pyrrolidin-2-one

Typical Procedure 8 was followed. Reaction of (R)-3-(6-bromo-pyridin-3-yloxy)-pyrrolidin-2-one with sodium 2-propanethiolate provided the title compound. MS ESI$^+$: m/z=253 [M+H]$^+$.

(R)-3-[6-(5-Hydroxymethyl-thiazol-2-yl)-pyridin-3-yloxy]-pyrrolidin-2-one

To a solution of (R)-methyl 2-(5-(2-oxopyrrolidin-3-yloxy)pyridin-2-yl)thiazole-5-carboxylate (360 mg) in THF (5 mL) was added LiBH$_4$ (100 mg) at 0° C. under nitrogen atmosphere. The reaction mixture was stirred at room temperature for 12 hours. After cooling to 0° C., the reaction was quenched by dropwise addition of water (until no more gas was generated). The reaction mixture was diluted with ethyl acetate (50 mL). The organic layer was washed with water (30 mL×2) and brine (20 mL) and dried over anhydrous Na$_2$SO$_4$. After filtration and evaporation of the solvent, the residue obtained was purified by silica gel column chromatography eluting with petroleum ether/ethyl acetate (4:1 to pure EA) to afford the title compound. MS ESI$^+$: m/z=292 [M+H]$^+$.

(R)-Methyl 2-(5-(2-oxopyrrolidin-3-yloxy)pyridin-2-yl)thiazole-5-carboxylate

To a round-bottomed flask was added methyl 2-(5-hydroxypyridin-2-yl)thiazole-5-carboxylate (400 mg), (S)-3-hydroxy-pyrrolidin-2-one (188 mg), PPh$_3$ (443 mg), and THF (10 mL). DEAD (299 mg) was added dropwise at 0° C. under nitrogen atmosphere. The reaction mixture was stirred at room temperature for 12 hours. After being diluted with ethyl acetate (50 mL), the organic layer was washed with water (20 mL×2) and brine (10 mL) and dried over anhydrous Na$_2$SO$_4$. After filtration and evaporation of the solvent, the residue obtained was purified by silica gel column chromatography eluting with petroleum ether/ethyl acetate (4:1 to 1:3) to afford the subtitle compound. MS ESI$^+$: m/z=320 [M-FH]$^+$.

Methyl 2-(5-hydroxypyridin-2-yl)thiazole-5-carboxylate

A solution of methyl 2-(5-(4-methoxybenzyloxy)pyridin-2-yl)thiazole-5-carboxylate (1.10 g) in TFA (10 mL) was stirred at 80° C. for 2 hours. After the reaction was complete, the mixture was evaporated. The residue was purified by silica gel column chromatography eluting with ethyl acetate/petroleum ether (1:2 to pure EA) to provide the subtitle compound. MS ESI$^+$: m/z=237 [M+H]$^+$.

2-(5-(4-Methoxybenzyloxy) pyridin-2-yl)thiazole-5-carboxylate

A mixture of 2-bromo-5-(4-methoxybenzyloxy)pyridine (1.10 g), methyl thiazole-5-carboxylate (644 mg), Pd(P(t-Bu)$_3$)$_2$ (153 mg), Cs$_2$CO$_3$ (1.20 g) and DMF (10 mL) was evacuated and refilled with nitrogen three times. The mixture was stirred at 150° C. under N$_2$ atmosphere for 3 hours. Insoluble material was removed by filtration through Celite. The filtrate was diluted with H$_2$O (100 mL). The solid obtained was collected by filtration and washed with MeOH to provide the subtitle compound. MS ESI$^+$: m/z=357 [M+H]$^+$.

2-Bromo-5-(4-methoxybenzyloxy) pyridine

To a round-bottomed flask was added 6-bromopyridin-3-ol (5.0 g), PMBCl (4.95 g), K$_2$CO$_3$ (7.93 g) and DMF (20 mL).

The resultant mixture was stirred at r.t. overnight. The reaction mixture was diluted with water (50 mL) and extracted with ethyl acetate (50 mL×2). The combined organic layers was washed with water (20 mL×2), brine (20 mL×2), and dried over anhydrous $Na_2SO_4$. After filtration and evaporation of the solvent, the residue was recrystallized from ethyl acetate and petroleum ether to provide the subtitle compound. MS ESI+: m/z=294 [M+H]+.

Preparation of Aryl Bromides

6-Bromo-4-fluoro-7-methyl-2,3-dihydroinden-1-one

To a solution of 3-(4-bromo-2-fluoro-5-methylphenyl)propanoic acid (EP1795524 A1; 8.4 g) in DCM (200 mL) was added $SOCl_2$ (19.1 g) dropwise at r.t. The mixture was stirred for 2 hours at r.t. The solvent was removed under reduced pressure. $AlCl_3$ (21.4 g) was added to the residue. The brown slurry was heated to 130° C. for 1.5 hours and then cooled to r.t. The residue was dissolved in EA (300 mL) and then washed with water and brine. The organic phase was dried over $Na_2SO_4$. The residue obtained after filtration and evaporation was purified by SGC (PE/EA 400:1) to provide the title compound. MS ESI+: m/z=243 [M+H]+.

Preparation of Examples 2

Example 2-01

A mixture of (R)-1-(7-fluoro-3-oxo-indan-5-yl)-3-(6-hydroxy-pyridin-3-yloxy)-pyrrolidin-2-one (100 mg), methanol (28 mg) and NMP/DCM/THF (1:1:1, 3 mL) was added triphenyl-phosphine (polymer, 2.39 mmol/g, 370 mg). After 5 minutes DIAD (208 mg) was added. After 2 hours insoluble material was removed by filtration. The filtrate was concentrated to provide a residue, which was purified by preparative HPLC to provide Example 2-01

Following essentially this procedure the Examples 2 in Table 2 were obtained by reacting (R)-1-(7-fluoro-3-oxo-indan-5-yl)-3-(6-hydroxy-pyridin-3-yloxy)-pyrrolidin-2-one with the respective alcohol.

TABLE 2

| Example | Structure | LCMS Method | $R_t$ [min] | ESI+ m/z [amu] |
|---------|-----------|-------------|-------------|----------------|
| 2-01 | 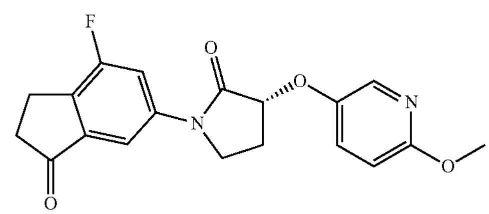 [SMILES: COc1ccc(O[C@@H]2CCN(c3cc(F)c4c(c3)C(=O)CC4)C2=O)cn1] | D | 4.02 | 357.1 |
| 2-02 | 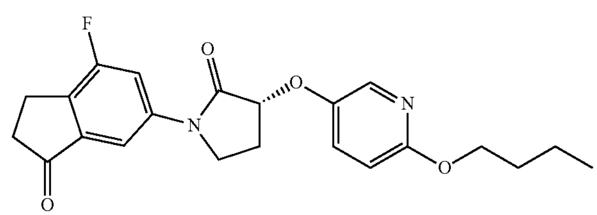 [SMILES: CCCCOc1ccc(O[C@@H]2CCN(c3cc(F)c4c(c3)C(=O)CC4)C2=O)cn1] | B | 1.90 | 399.2 |
| 2-03 | 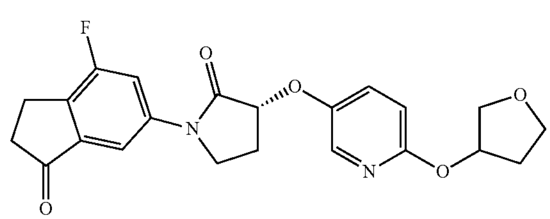 [SMILES: O=C1CCc2c(F)cc(N3CC[C@@H](Oc4ccc(OC5CCOC5)nc4)C3=O)cc21] | B | 1.78 | 413.2 |
| 2-04 | 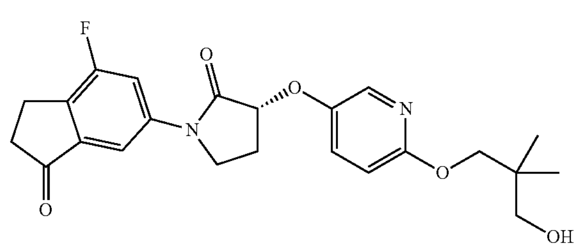 [SMILES: CC(C)(CO)COc1ccc(O[C@@H]2CCN(c3cc(F)c4c(c3)C(=O)CC4)C2=O)cn1] | B | 1.83 | 429.2 |

TABLE 2-continued

| Example | Structure | LCMS Method | R$_t$ [min] | ESI$^+$ m/z [amu] |
|---|---|---|---|---|
| 2-05 | 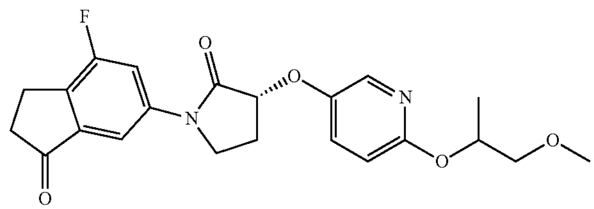 [SMILES: COCC(C)Oc1ccc(O[C@@H]2CCN(c3cc(F)c4c(c3)C(=O)CC4)C2=O)cn1] | B | 1.86 | 415.2 |
| 2-06 | 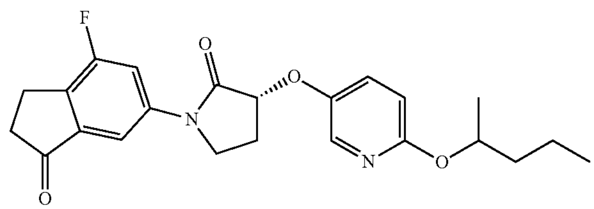 [SMILES: CCCC(C)Oc1ccc(O[C@@H]2CCN(c3cc(F)c4c(c3)C(=O)CC4)C2=O)cn1] | B | 2.09 | 413.2 |
| 2-07 | 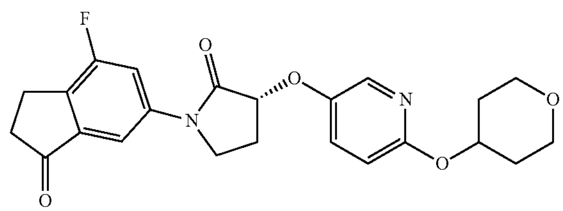 [SMILES: O=C1CCc2c(F)cc(N3CC[C@@H](Oc4ccc(OC5CCOCC5)nc4)C3=O)cc21] | B | 1.82 | 427.2 |
| 2-08 | 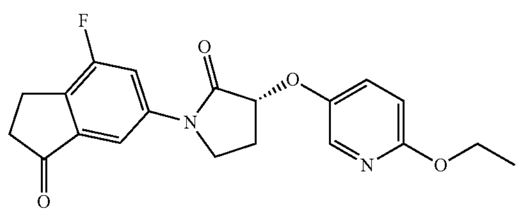 [SMILES: CCOc1ccc(O[C@@H]2CCN(c3cc(F)c4c(c3)C(=O)CC4)C2=O)cn1] | D | 4.33 | 371.2 |
| 2-09 | 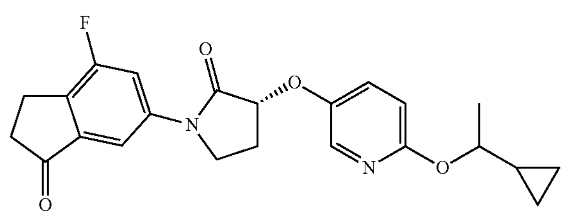 [SMILES: CC(Oc1ccc(O[C@@H]2CCN(c3cc(F)c4c(c3)C(=O)CC4)C2=O)cn1)C1CC1] | B | 2.01 | 411.2 |
| 2-10 | 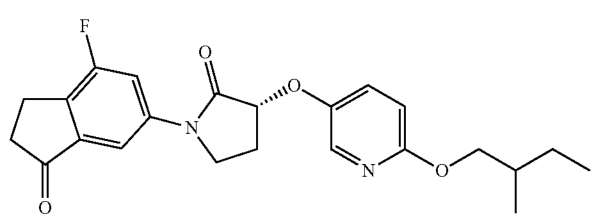 [SMILES: CCC(C)COc1ccc(O[C@@H]2CCN(c3cc(F)c4c(c3)C(=O)CC4)C2=O)cn1] | B | 2.09 | 413.3 |
| 2-11 | 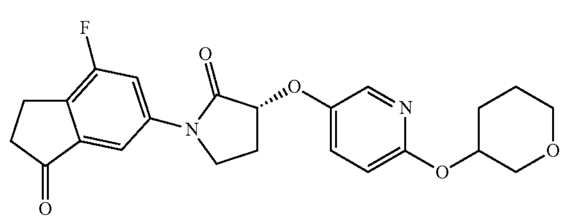 [SMILES: O=C1CCc2c(F)cc(N3CC[C@@H](Oc4ccc(OC5CCCOC5)nc4)C3=O)cc21] | B | 1.85 | 427.2 |

TABLE 2-continued

| Example | Structure | LCMS Method | R$_t$ [min] | ESI$^+$ m/z [amu] |
|---|---|---|---|---|
| 2-12 | 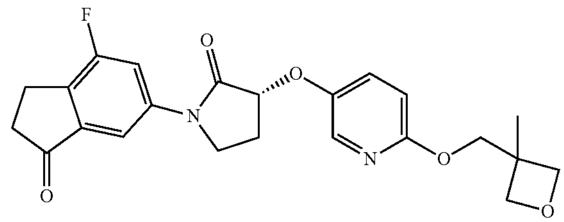 [SMILES: CC1(COc2ccc(O[C@@H]3CCN(c4cc(F)c5c(c4)C(=O)CC5)C3=O)cn2)COC1] | B | 1.81 | 427.2 |
| 2-13 | 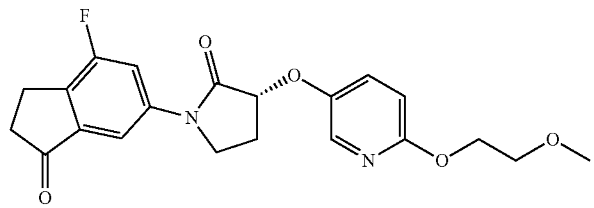 [SMILES: COCCOc1ccc(O[C@@H]2CCN(c3cc(F)c4c(c3)C(=O)CC4)C2=O)cn1] | B | 1.77 | 401.2 |
| 2-14 | 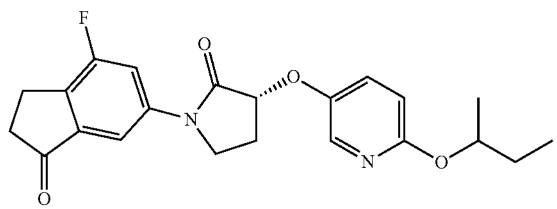 [SMILES: CCC(C)Oc1ccc(O[C@@H]2CCN(c3cc(F)c4c(c3)C(=O)CC4)C2=O)cn1] | B | 2.02 | 399.2 |
| 2-15 | 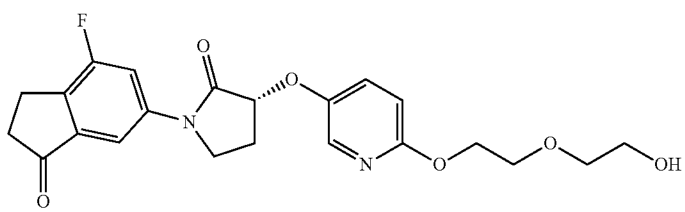 [SMILES: O=C1CCc2c(F)cc(N3CC[C@@H](Oc4ccc(OCCOCCO)nc4)C3=O)cc21] | B | 1.49 | 431.2 |
| 2-16 | 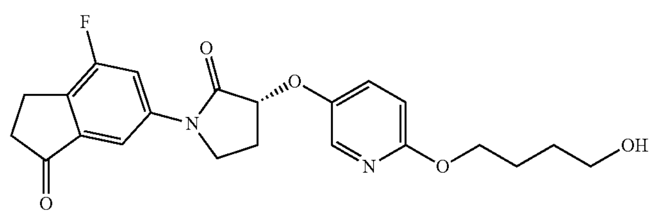 [SMILES: O=C1CCc2c(F)cc(N3CC[C@@H](Oc4ccc(OCCCCO)nc4)C3=O)cc21] | B | 1.70 | 415.2 |
| 2-17 | 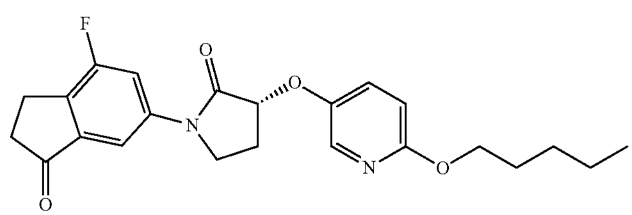 [SMILES: CCCCCOc1ccc(O[C@@H]2CCN(c3cc(F)c4c(c3)C(=O)CC4)C2=O)cn1] | B | 2.10 | 413.2 |
| 2-18 | 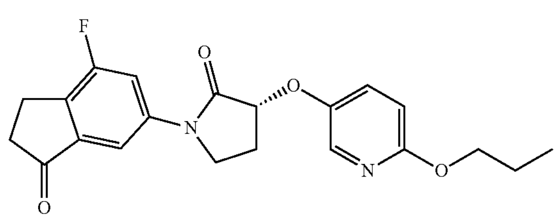 [SMILES: CCCOc1ccc(O[C@@H]2CCN(c3cc(F)c4c(c3)C(=O)CC4)C2=O)cn1] | B | 1.95 | 385.2 |

TABLE 2-continued

| Example | Structure | LCMS Method | R$_t$ [min] | ESI$^+$ m/z [amu] |
|---|---|---|---|---|
| 2-19 | 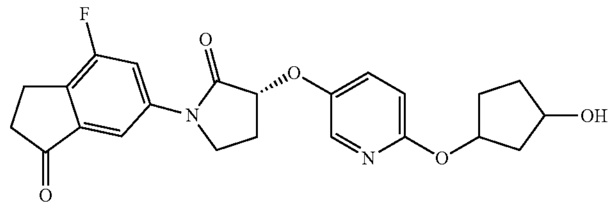 [SMILES: O=C1CCc2c(F)cc(N3CC[C@@H](Oc4ccc(OC5CCC(O)C5)nc4)C3=O)cc21] | B | 1.71 | 427.2 |
| 2-20 | 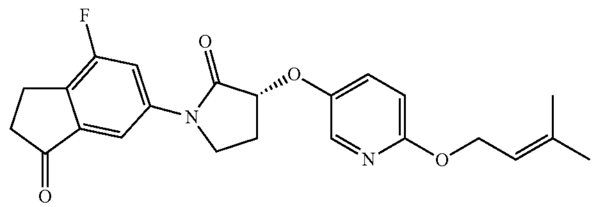 [SMILES: CC(C)=CCOc1ccc(O[C@@H]2CCN(c3cc(F)c4c(c3)C(=O)CC4)C2=O)cn1] | B | 1.77 | 411.2 |
| 2-21 | 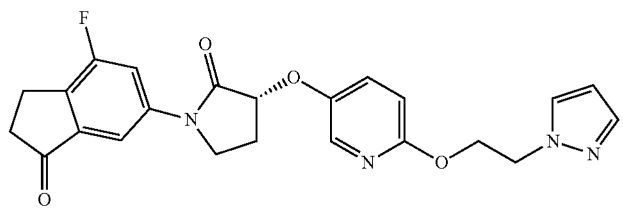 [SMILES: O=C1CCc2c(F)cc(N3CC[C@@H](Oc4ccc(OCCn5cccn5)nc4)C3=O)cc21] | B | 1.78 | 437.2 |
| 2-22 | 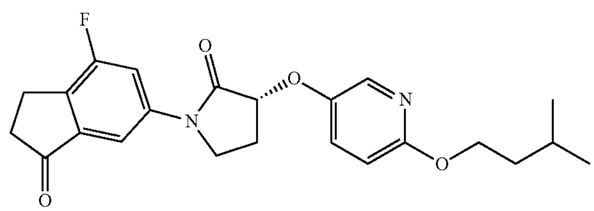 [SMILES: CC(C)CCOc1ccc(O[C@@H]2CCN(c3cc(F)c4c(c3)C(=O)CC4)C2=O)cn1] | B | 2.09 | 413.3 |
| 2-23 | 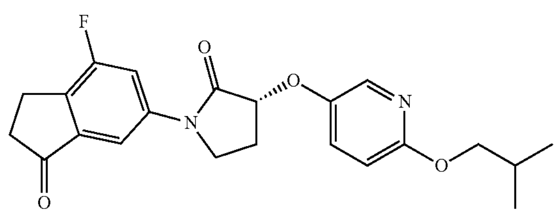 [SMILES: CC(C)COc1ccc(O[C@@H]2CCN(c3cc(F)c4c(c3)C(=O)CC4)C2=O)cn1] | B | 2.03 | 399.2 |
| 2-24 | 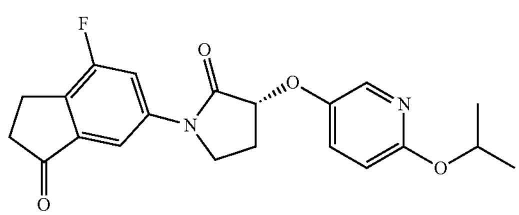 [SMILES: CC(C)Oc1ccc(O[C@@H]2CCN(c3cc(F)c4c(c3)C(=O)CC4)C2=O)cn1] | B | 1.94 | 385.2 |
| 2-25 | 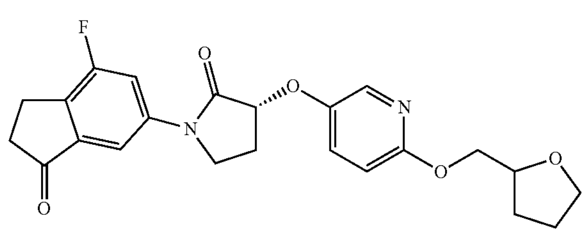 [SMILES: O=C1CCc2c(F)cc(N3CC[C@@H](Oc4ccc(OCC5CCCO5)nc4)C3=O)cc21] | B | 1.83 | 427.2 |

TABLE 2-continued
| Example | Structure | LCMS Method | R$_t$ [min] | ESI$^+$ m/z [amu] |
|---|---|---|---|---|
| 2-26 | 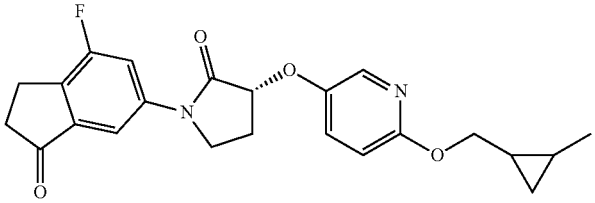 [SMILES: CC1CC1COc1ccc(O[C@@H]2CCN(c3cc(F)c4c(c3)C(=O)CC4)C2=O)cn1] | B | 2.02 | 411.2 |
| 2-27 | 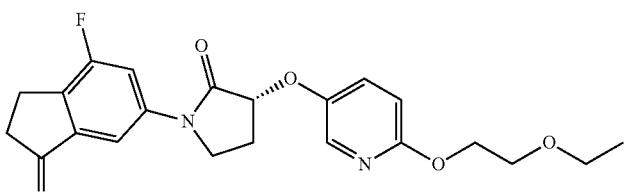 | B | 1.85 | 415.2 |
| 2-28 | 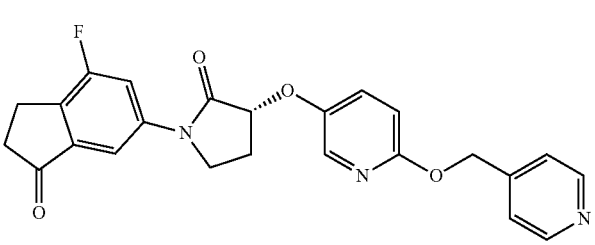 [SMILES: O=C1CCc2c(F)cc(N3CC[C@@H](Oc4ccc(OCc5ccncc5)nc4)C3=O)cc21] | B | 1.52 | 434.2 |
| 2-29 | 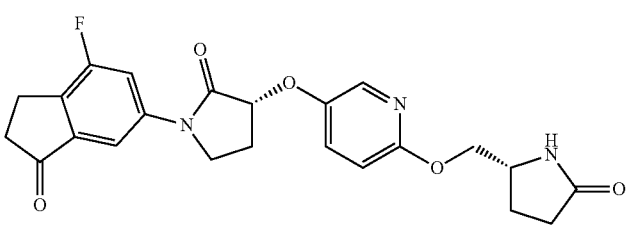 [SMILES: O=C1CC[C@H](COc2ccc(O[C@@H]3CCN(c4cc(F)c5c(c4)C(=O)CC5)C3=O)cn2)N1] | B | 1.64 | 440.2 |
| 2-30 | 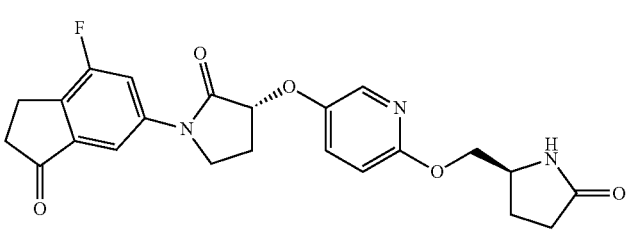 [SMILES: O=C1CC[C@@H](COc2ccc(O[C@@H]3CCN(c4cc(F)c5c(c4)C(=O)CC5)C3=O)cn2)N1] | B | 1.50 | 440.2 |
| 2-31 | 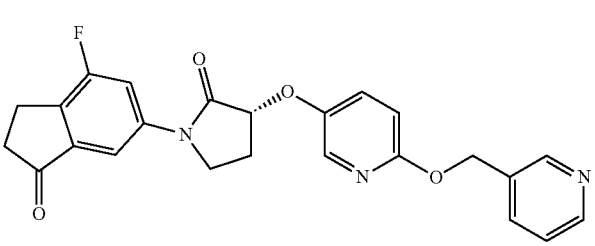 [SMILES: O=C1CCc2c(F)cc(N3CC[C@@H](Oc4ccc(OCc5cccnc5)nc4)C3=O)cc21] | D | 2.69 | 434.2 |

TABLE 2-continued

| Example | Structure | LCMS Method | R$_t$ [min] | ESI$^+$ m/z [amu] |
|---|---|---|---|---|
| 2-32 | 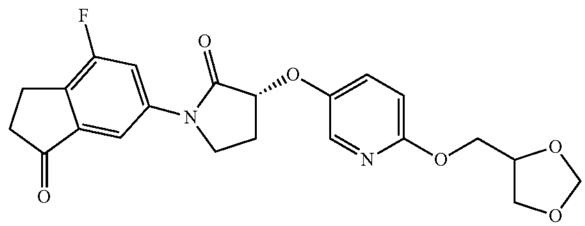 [SMILES: O=C1CCc2c(F)cc(N3CC[C@@H](Oc4ccc(OCC5COCO5)nc4)C3=O)cc21] | B | 1.63 | 429.2 |
| 2-33 | 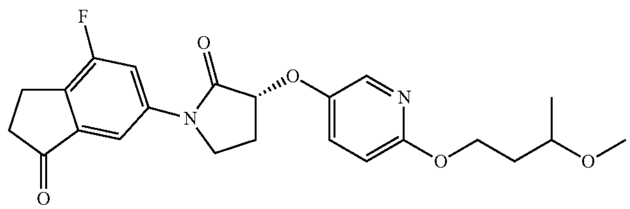 [SMILES: COC(C)CCOc1ccc(O[C@@H]2CCN(c3cc(F)c4c(c3)C(=O)CC4)C2=O)cn1] | B | 1.77 | 429.3 |
| 2-34 | 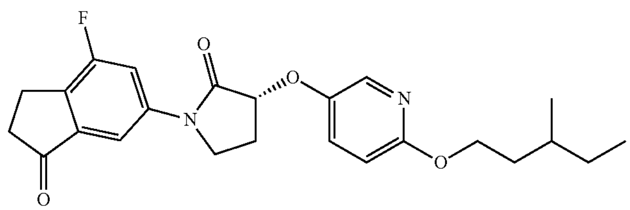 [SMILES: CCC(C)CCOc1ccc(O[C@@H]2CCN(c3cc(F)c4c(c3)C(=O)CC4)C2=O)cn1] | B | 2.04 | 427.3 |
| 2-35 | 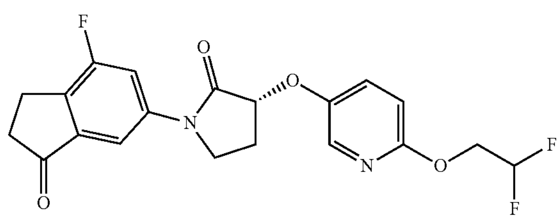 [SMILES: O=C1CCc2c(F)cc(N3CC[C@@H](Oc4ccc(OCC(F)F)nc4)C3=O)cc21] | B | 1.76 | 407.2 |
| 2-36 | 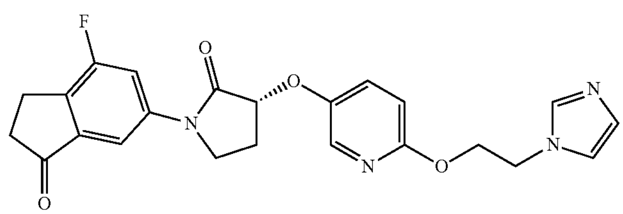 [SMILES: O=C1CCc2c(F)cc(N3CC[C@@H](Oc4ccc(OCCn5ccnc5)nc4)C3=O)cc21] | B | 1.25 | 437.2 |
| 2-37 | 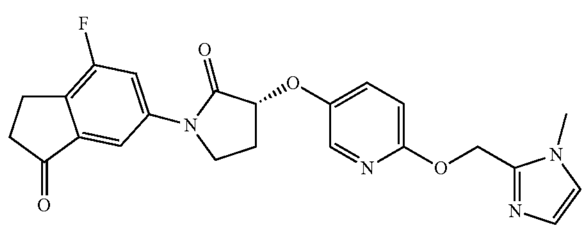 [SMILES: Cn1ccnc1COc1ccc(O[C@@H]2CCN(c3cc(F)c4c(c3)C(=O)CC4)C2=O)cn1] | B | 1.27 | 437.2 |
| 2-38 | 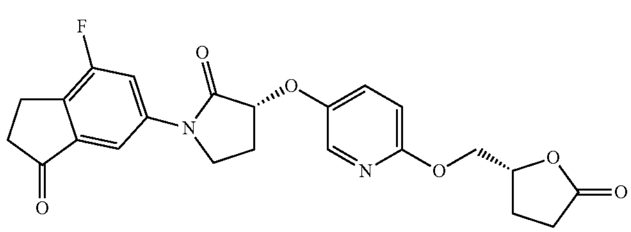 [SMILES: O=C1CC[C@H](COc2ccc(O[C@@H]3CCN(c4cc(F)c5c(c4)C(=O)CC5)C3=O)cn2)O1] | B | 1.60 | 441.2 |

TABLE 2-continued

| Example | Structure | LCMS Method | R$_t$ [min] | ESI$^+$ m/z [amu] |
|---|---|---|---|---|
| 2-39 | 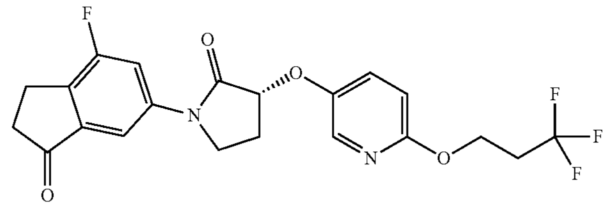 [SMILES: O=C1CCc2c(F)cc(N3CC[C@@H](Oc4ccc(OCCC(F)(F)F)nc4)C3=O)cc21] | B | 1.85 | 439.2 |
| 2-40 | 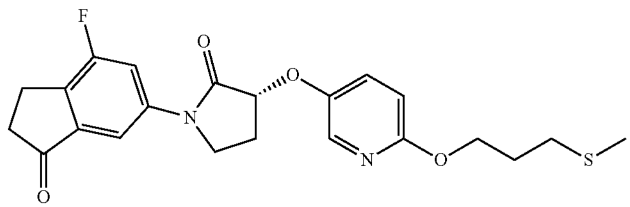 [SMILES: CSCCCOc1ccc(O[C@@H]2CCN(c3cc(F)c4c(c3)C(=O)CC4)C2=O)cn1] | B | 1.84 | 431.2 |
| 2-41 | 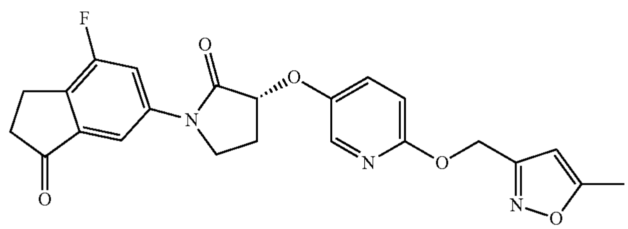 [SMILES: Cc1cc(COc2ccc(O[C@@H]3CCN(c4cc(F)c5c(c4)C(=O)CC5)C3=O)cn2)no1] | B | 1.74 | 438.2 |
| 2-42 | 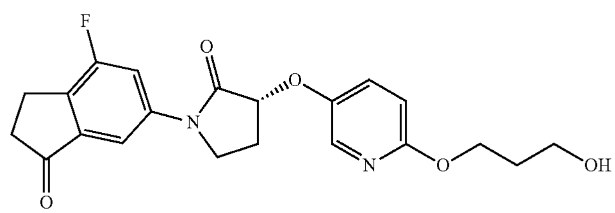 [SMILES: O=C1CCc2c(F)cc(N3CC[C@@H](Oc4ccc(OCCCO)nc4)C3=O)cc21] | B | 1.52 | 401.2 |
| 2-43 | 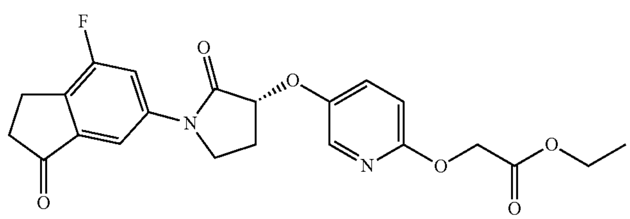 [SMILES: CCOC(=O)COc1ccc(O[C@@H]2CCN(c3cc(F)c4c(c3)C(=O)CC4)C2=O)cn1] | B | 1.74 | 429.2 |
| 2-44 | 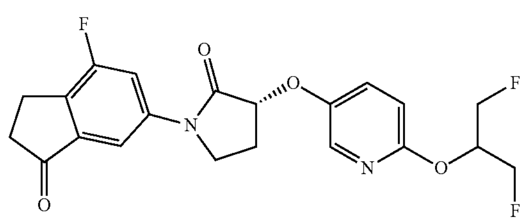 [SMILES: O=C1CCc2c(F)cc(N3CC[C@@H](Oc4ccc(OC(CF)CF)nc4)C3=O)cc21] | B | 1.76 | 421.2 |
| 2-45 | 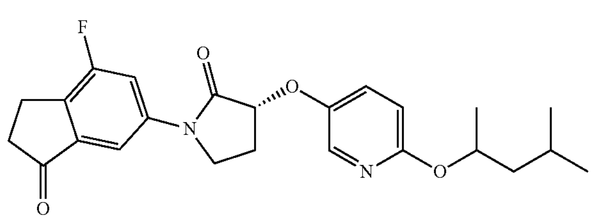 [SMILES: CC(C)CC(C)Oc1ccc(O[C@@H]2CCN(c3cc(F)c4c(c3)C(=O)CC4)C2=O)cn1] | B | 2.03 | 427.3 |

TABLE 2-continued
| Example | Structure | LCMS Method | R$_t$ [min] | ESI$^+$ m/z [amu] |
|---|---|---|---|---|
| 2-46 | 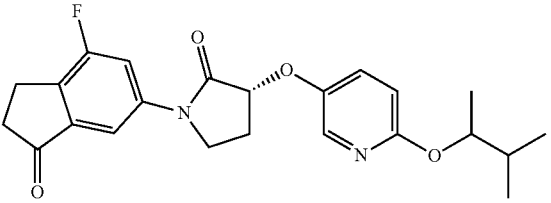 [SMILES: CC(C)C(C)Oc1ccc(O[C@@H]2CCN(c3cc(F)c4c(c3)C(=O)CC4)C2=O)cn1] | B | 1.97 | 413.3 |
| 2-47 | 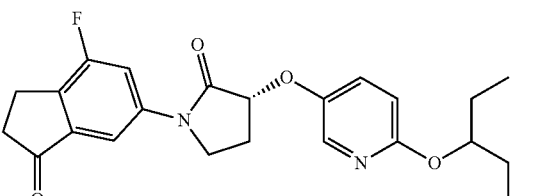 | B | 1.82 | 429.3 |
| 2-48 | 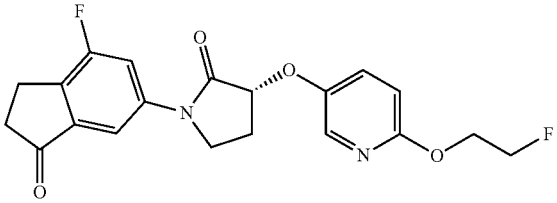 [SMILES: O=C1CCc2c(F)cc(N3CC[C@@H](Oc4ccc(OCCF)nc4)C3=O)cc21] | B | 1.68 | 389.2 |
| 2-49 | 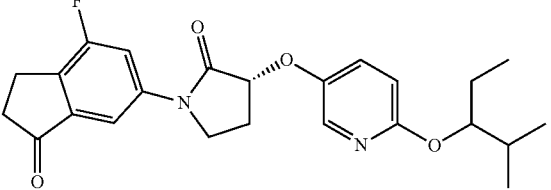 | B | 2.04 | 427.3 |
| 2-50 | 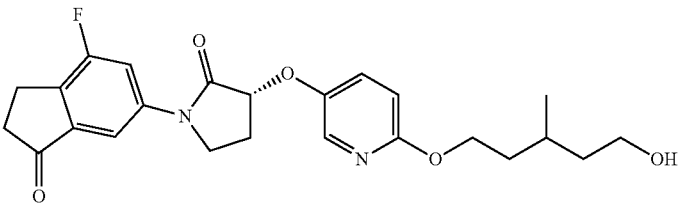 [SMILES: CC(CCO)CCOc1ccc(O[C@@H]2CCN(c3cc(F)c4c(c3)C(=O)CC4)C2=O)cn1] | B | 1.70 | 443.3 |
| 2-51 | 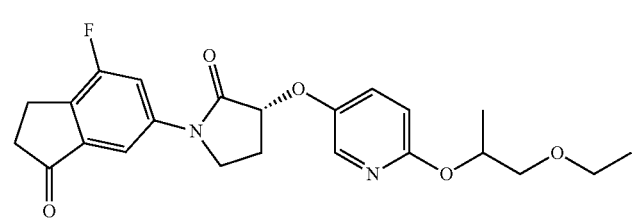 [SMILES: CCOCC(C)Oc1ccc(O[C@@H]2CCN(c3cc(F)c4c(c3)C(=O)CC4)C2=O)cn1] | B | 1.81 | 429.3 |
| 2-52 | 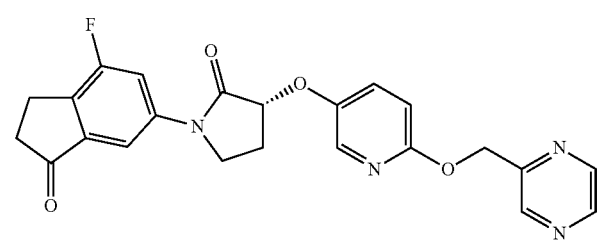 [SMILES: O=C1CCc2c(F)cc(N3CC[C@@H](Oc4ccc(OCc5cnccn5)nc4)C3=O)cc21] | B | 1.61 | 435.2 |

TABLE 2-continued

| Example | Structure | LCMS Method | R$_t$ [min] | ESI$^+$ m/z [amu] |
|---|---|---|---|---|
| 2-53 | 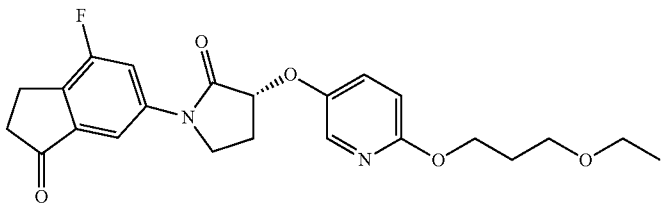 [SMILES: CCOCCCOc1ccc(O[C@@H]2CCN(c3cc(F)c4c(c3)C(=O)CC4)C2=O)cn1] | B | 1.92 | 429.2 |
| 2-54 | 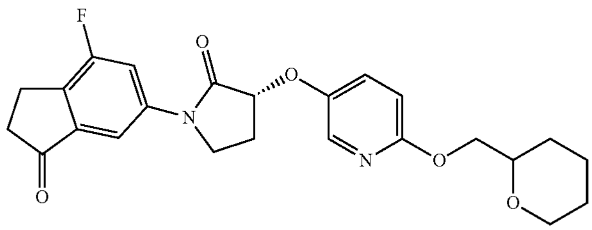 [SMILES: O=C1CCc2c(F)cc(N3CC[C@@H](Oc4ccc(OCC5CCCCO5)nc4)C3=O)cc21] | B | 1.92 | 441.2 |
| 2-55 | 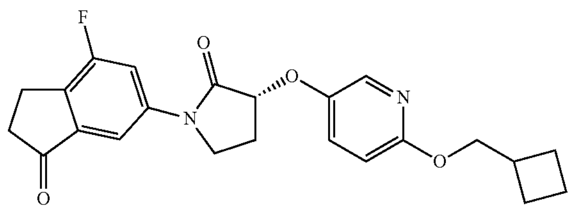 [SMILES: O=C1CCc2c(F)cc(N3CC[C@@H](Oc4ccc(OCC5CCC5)nc4)C3=O)cc21] | B | 2.06 | 411.2 |
| 2-56 | 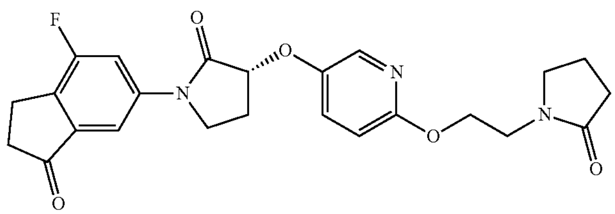 [SMILES: O=C1CCc2c(F)cc(N3CC[C@@H](Oc4ccc(OCCN5CCCC5=O)nc4)C3=O)cc21] | B | 1.71 | 454.2 |
| 2-57 | 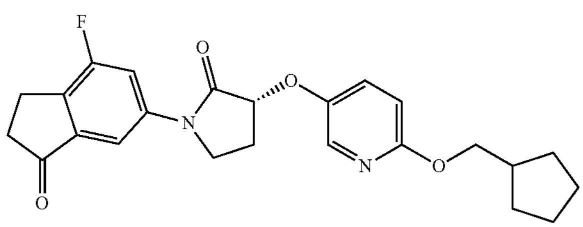 [SMILES: O=C1CCc2c(F)cc(N3CC[C@@H](Oc4ccc(OCC5CCCC5)nc4)C3=O)cc21] | B | 2.12 | 425.2 |
| 2-58 | 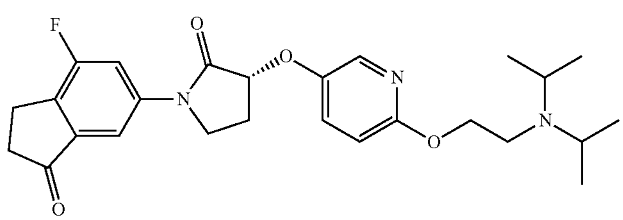 [SMILES: CC(C)N(CCOc1ccc(O[C@@H]2CCN(c3cc(F)c4c(c3)C(=O)CC4)C2=O)cn1)C(C)C] | B | 1.44 | 470.3 |
| 2-59 | 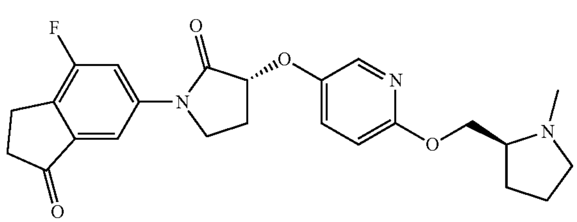 [SMILES: CN1CCC[C@H]1COc1ccc(O[C@@H]2CCN(c3cc(F)c4c(c3)C(=O)CC4)C2=O)cn1] | B | 1.47 | 440.2 |

TABLE 2-continued

| Example | Structure | LCMS Method | R$_t$ [min] | ESI$^+$ m/z [amu] |
|---|---|---|---|---|
| 2-60 | 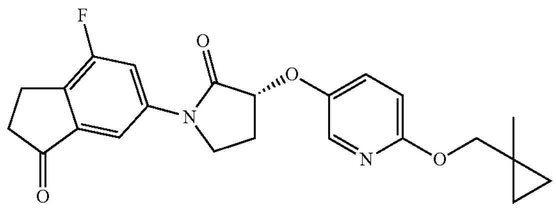 [SMILES: CC1(COc2ccc(O[C@@H]3CCN(c4cc(F)c5c(c4)C(=O)CC5)C3=O)cn2)CC1] | B | 4.77 | 411.2 |
| 2-61 | 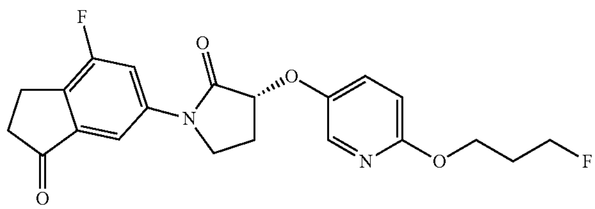 [SMILES: O=C1CCc2c(F)cc(N3CC[C@@H](Oc4ccc(OCCCF)nc4)C3=O)cc21] | B | 1.88 | 403.2 |
| 2-62 | 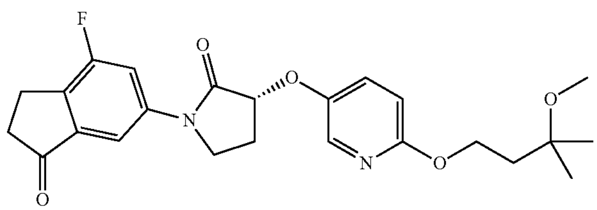 [SMILES: COC(C)(C)CCOc1ccc(O[C@@H]2CCN(c3cc(F)c4c(c3)C(=O)CC4)C2=O)cn1] | B | 1.95 | 443.2 |
| 2-63 | 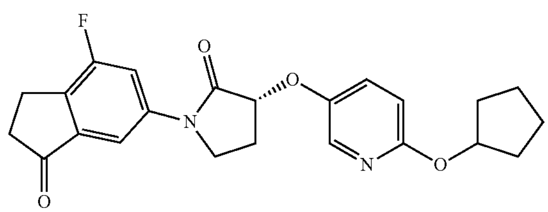 [SMILES: O=C1CCc2c(F)cc(N3CC[C@@H](Oc4ccc(OC5CCCC5)nc4)C3=O)cc21] | B | 2.04 | 411.2 |
| 2-64 | 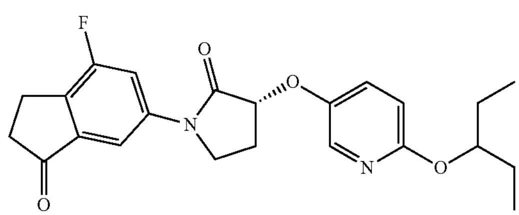 [SMILES: CCC(CC)Oc1ccc(O[C@@H]2CCN(c3cc(F)c4c(c3)C(=O)CC4)C2=O)cn1] | B | 2.09 | 413.2 |
| 2-65 | 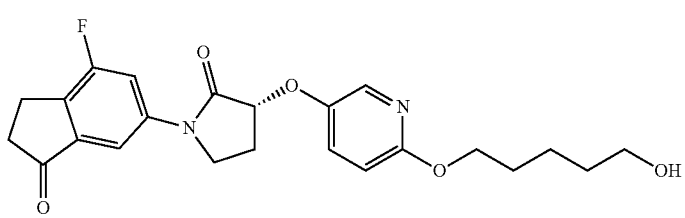 [SMILES: O=C1CCc2c(F)cc(N3CC[C@@H](Oc4ccc(OCCCCCO)nc4)C3=O)cc21] | B | 1.77 | 429.2 |
| 2-66 | 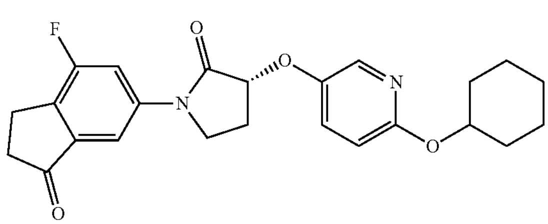 [SMILES: O=C1CCc2c(F)cc(N3CC[C@@H](Oc4ccc(OC5CCCCC5)nc4)C3=O)cc21] | B | 2.10 | 425.2 |

TABLE 2-continued

| Example | Structure | LCMS Method | R$_t$ [min] | ESI$^+$ m/z [amu] |
|---|---|---|---|---|
| 2-67 | 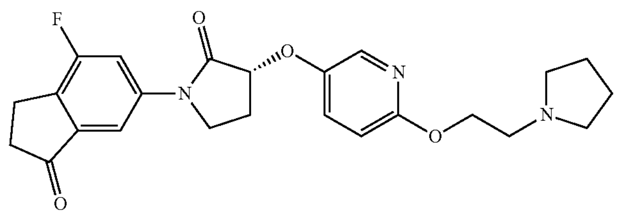 [SMILES: O=C1CCc2c(F)cc(N3CC[C@@H](Oc4ccc(OCCN5CCCC5)nc4)C3=O)cc21] | B | 1.46 | 440.2 |
| 2-68 | 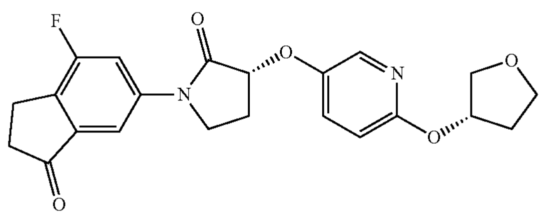 [SMILES: O=C1CCc2c(F)cc(N3CC[C@@H](Oc4ccc(O[C@H]5CCOC5)nc4)C3=O)cc21] | B | 1.79 | 413.1 |
| 2-69 | 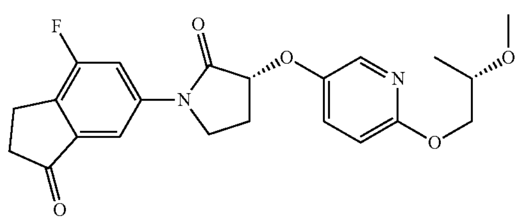 [SMILES: CO[C@@H](C)COc1ccc(O[C@@H]2CCN(c3cc(F)c4c(c3)C(=O)CC4)C2=O)cn1] | B | 1.84 | 415.2 |
| 2-70 | 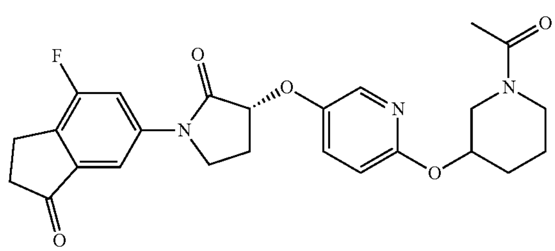 [SMILES: CC(=O)N1CCCC(Oc2ccc(O[C@@H]3CCN(c4cc(F)c5c(c4)C(=O)CC5)C3=O)cn2)C1] | B | 1.74 | 468.2 |
| 2-71 | 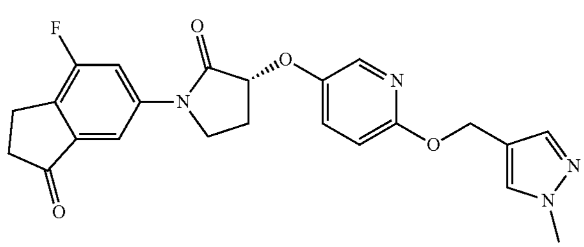 [SMILES: Cn1cc(COc2ccc(O[C@@H]3CCN(c4cc(F)c5c(c4)C(=O)CC5)C3=O)cn2)cn1] | B | 1.76 | 437.1 |
| 2-72 | 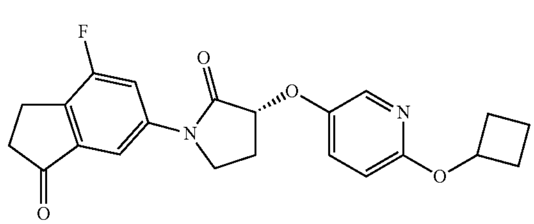 [SMILES: O=C1CCc2c(F)cc(N3CC[C@@H](Oc4ccc(OC5CCC5)nc4)C3=O)cc21] | D | 1.97 | 397.2 |

TABLE 2-continued

| Example | Structure | LCMS Method | R$_t$ [min] | ESI$^+$ m/z [amu] |
|---|---|---|---|---|
| 2-73 | 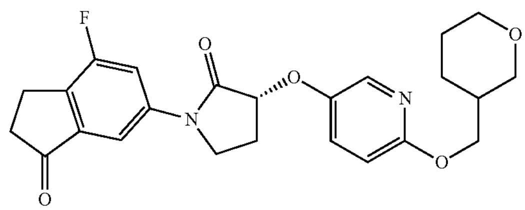 [SMILES: O=C1CCc2c(F)cc(N3CC[C@@H](Oc4ccc(OCC5CCCOC5)nc4)C3=O)cc21] | B | 1.90 | 441.2 |
| 2-74 | 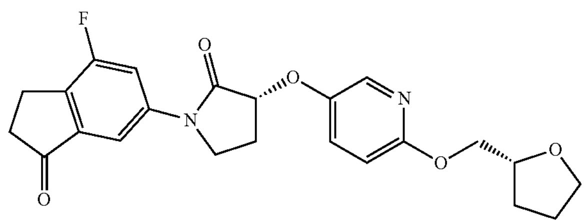 [SMILES: O=C1CCc2c(F)cc(N3CC[C@@H](Oc4ccc(OC[C@H]5CCCO5)nc4)C3=O)cc21] | B | 1.84 | 427.2 |
| 2-75 | 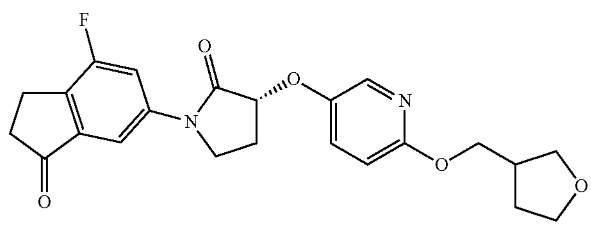 [SMILES: O=C1CCc2c(F)cc(N3CC[C@@H](Oc4ccc(OCC5CCOC5)nc4)C3=O)cc21] | B | 1.82 | 427.2 |
| 2-76 | 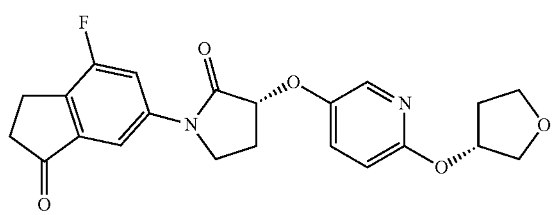 [SMILES: O=C1CCc2c(F)cc(N3CC[C@@H](Oc4ccc(O[C@@H]5CCOC5)nc4)C3=O)cc21] | B | 1.79 | 413.2 |
| 2-77 | 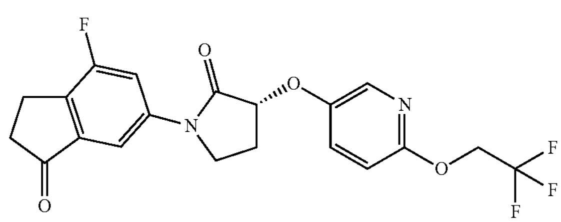 [SMILES: O=C1CCc2c(F)cc(N3CC[C@@H](Oc4ccc(OCC(F)(F)F)nc4)C3=O)cc21] | B | 4.69 | 425.2 |
| 2-78 | STEREOMER 1 | B | 1.72 | 427.2 |

TABLE 2-continued

| Example | Structure | LCMS Method | R$_t$ [min] | ESI$^+$ m/z [amu] |
|---|---|---|---|---|
| 2-79 | STEREOMER 2 | B | 1.72 | 427.2 |

Alternative Preparation of (R)-1-(7-Fluoro-3-oxo-indan-5-yl)-3-[6-(tetrahydro-pyran-4-yloxy)-pyridin-3-yloxy]-pyrrolidin-2-one (Example 2-07)

To a mixture of (R)-1-(7-fluoro-3-oxo-indan-5-yl)-3-(6-hydroxy-pyridin-3-yloxy)-pyrrolidin-(60 mg), tetrahydro-pyran-4-ol (51 mg) and solvent (THF/DCM/NMP 4:4:1, 5 mL) under argon was added triphenylphosphine (polymer, 0.4 mmol). After 5 minutes DIAD (51 mg) was added. The mixture was shaken at 40° C. for 12 hours. The mixture was filtered and the filtrate was concentrated. The residue was purified by preparative HPLC to provide Example 2-07. $^1$H-NMR (400 MHz, DMSO) δ 7.99 (1H, dd, J=11.2, 1.8 Hz), 7.97 (1H, d, J=3.1 Hz), 7.78 (1H, d, J=1.8 Hz), 7.54 (1H, dd, J=9.0, 3.1 Hz), 6.78 (1H, d, J=9.0 Hz), 5.23 (1H, dd, J=8.3, 8.3 Hz), 5.08 (1H, m), 3.96 (1H, m), 3.86 (1H, m), 3.86 (2H, m), 3.10 (2H, m), 2.73 (2H, m), 2.70 (1H, m), 2.13 (1H, m), 1.98 (2H, m), 1.60 (2H, m).

Alternative Preparation of (R)-3-(6-Ethoxy-pyridin-3-yloxy)-1-(7-fluoro-3-oxo-indan-5-yl)-pyrrolidin-2-one (Example 2-08)

To a mixture of (R)-1-(7-fluoro-3-oxo-indan-5-yl)-3-(6-hydroxy-pyridin-3-yloxy)-pyrrolidin-2-one (60 mg), ethanol (23 mg) and solvent (THF/DCM/NMP 4:4:1, 5 mL) under argon was added triphenylphosphine (polymer, 0.4 mmol). After 5 minutes DIAD (51 mg) was added. The mixture was shaken at 40° C. for 12 hours. The mixture was filtered and the filtrate was concentrated. The residue was purified by preparative HPLC to provide Example 2-08.

In a further alternative preparation a mixture of (R)-3-((6-ethoxypyridin-3-yl)oxy)pyrrolidin-2-one (2.00 g), 6-bromo-4-fluoro-2,3-dihydro-1H-inden-1-one (2.30 g), N,N'-dimethyl-ethylene-diamine (10 mL) and 1,4-dioxane (20 mL) was purged with argon and cesium carbonate (3.8 g) and copper(I) iodide (100 mg) were added. The mixture was heated to 100° C. for 1.5 hours. After cooling to r.t. the mixture was diluted with EA and washed with water (5 times) and brine. The organic layer was dried (Na$_2$SO$_4$) and concentrated. The residue was purified by SGC (eluent: heptane with 0 to 70% EA) to provide Example 2-08. $^1$H-NMR (400 MHz, DMSO) δ 7.99 (1H, dd, J=11.3, 1.8 Hz), 7.97 (1H, d, J=3.1 Hz), 7.77 (1H, d, J=1.8 Hz), 7.53 (1H, dd, J=8.9, 3.1 Hz), 6.76 (1H, d, J=8.9 Hz), 5.22 (1H, dd, J=8.3, 8.3 Hz), 4.24 (2H, q, J=7.0 Hz), 3.96 (1H, m), 3.86 (1H, m), 3.11 (2H, m), 2.72 (2H, m), 2.69 (1H, m), 2.13 (1H, m), 1.30 (3H, t, J=7.0 Hz).

(R)-3((6-Ethoxypyridin-3-yl)oxy)pyrrolidin-2-one

A mixture of (S)-3-hydroxy-pyrrolidin-2-one (8.07 g), 6-ethoxypyridin-3-ol (11.0 g) and THF (100 mL) was purged with argon. Triphenylphosphine (20.7 g) was added followed by slow addition of DIAD (16.0 g). After 2 hours the mixture was concentrated and the residue purified by SGC (eluent: EA) to provide the subtitle compound. MS ESI$^+$: m/z=223 [M+H]$^+$.

Alternative Preparation of (R)-1-(7-Fluoro-3-oxo-indan-5-yl)-3-(6-isopropoxy-pyridin-3-yloxy)-pyrrolidin-2-one (Example 2-24)

To a mixture of (R)-1-(7-fluoro-3-oxo-indan-5-yl)-3-(6-hydroxy-pyridin-3-yloxy)-pyrrolidin-2-one (60 mg), isopropanol (30 mg) and solvent (THF/DCM/NMP 4:4:1, 5 mL) under argon was added triphenylphosphine (polymer, 0.4 mmol). After 5 minutes DIAD (51 mg) was added. The mixture was shaken at 40° C. for 12 hours. The mixture was filtered and the filtrate was concentrated. The residue was purified by preparative HPLC to provide Example 2-24. $^1$H-NMR (400 MHz, DMSO) δ 7.99 (1H, dd, J=11.1, 1.8 Hz), 7.97 (1H, d, J=3.1 Hz), 7.77 (1H, d, J=1.8 Hz), 7.51 (1H, dd, J=9.0, 3.1 Hz), 6.71 (1H, d, J=9.0 Hz), 5.22 (1H, dd, J=8.3, 8.3 Hz), 5.14 (1H, m), 3.96 (1H, m), 3.85 (1H, m), 3.10 (2H, m), 2.72 (2H, m), 2.69 (1H, m), 2.14 (1H, m), 1.27 (6H, d, J=6.2 Hz).

Preparation of (R)-1-(7-Fluoro-3-oxo-indan-5-yl)-3-(6-hydroxy-pyridin-3-yloxy)-pyrrolidin-2-one Typical Procedure 7 was followed. Hydrogenation of (R)-3-(6-benzyloxy-pyridin-3-yloxy)-1-(7-fluoro-3-oxo-indan-5-yl)-pyrrolidin-2-one over Pd/C provided the title compound. MS ESI$^+$: m/z=343 [M+H]$^+$.

Preparation of Examples 3

Example 3-01

Typical Procedure 3 was followed. Reaction of (S)-1-(7-fluoro-3-oxo-indan-5-yl)-3-hydroxy-pyrrolidin-2-one with 4-trifluoromethoxy-phenol provided Example 3-01. Following this procedure the Examples 3 in Table 3 were obtained by reacting 1-(7-fluoro-3-oxo-indan-5-yl)-3-hydroxy-pyrrolidin-2-one (R- or S-isomer) with the respective phenol or hydroxy-pyridine.

TABLE 3

| Example | Structure | LCMS Method | R_t [min] | ESI+ m/z [amu] |
|---|---|---|---|---|
| 3-01 | 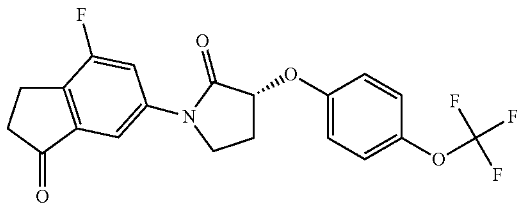 [SMILES: O=C1CCc2c(F)cc(N3CC[C@@H](Oc4ccc(OC(F)(F)F)cc4)C3=O)cc21] | D | 4.79 | 410.3 |
| 3-02 | 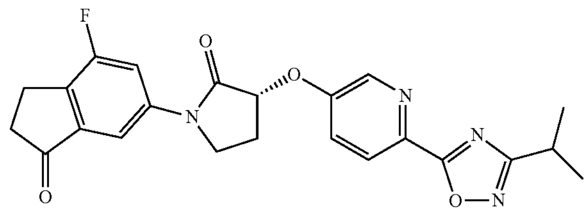 [SMILES: CC(C)c1noc(-c2ccc(O[C@@H]3CCN(c4cc(F)c5c(c4)C(=O)CC5)C3=O)cn2)n1] | B | 1.91 | 437.2 |
| 3-03 | 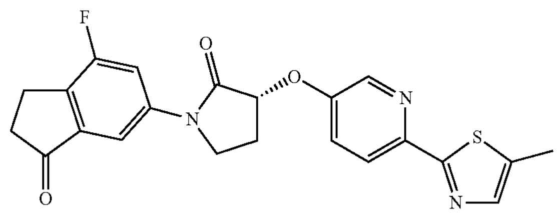 [SMILES: Cc1cnc(-c2ccc(O[C@@H]3CCN(c4cc(F)c5c(c4)C(=O)CC5)C3=O)cn2)s1] | D | 4.46 | 424.1 |
| 3-04 | 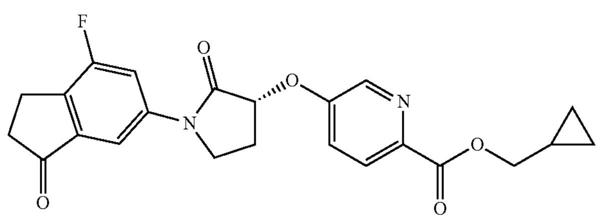 [SMILES: O=C(OCC1CC1)c1ccc(O[C@@H]2CCN(c3cc(F)c4c(c3)C(=O)CC4)C2=O)cn1] | B | 1.84 | 425.1 |
| 3-05 | 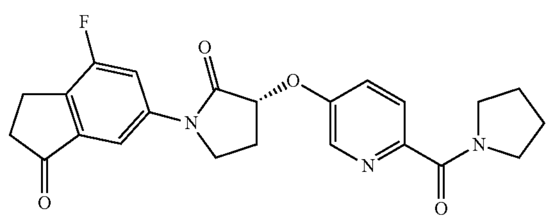 [SMILES: O=C1CCc2c(F)cc(N3CC[C@@H](Oc4ccc(C(=O)N5CCCC5)nc4)C3=O)cc21] | B | 1.71 | 424.2 |
| 3-06 | 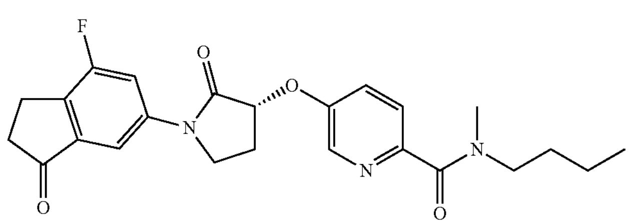 [SMILES: CCCCN(C)C(=O)c1ccc(O[C@@H]2CCN(c3cc(F)c4c(c3)C(=O)CC4)C2=O)cn1] | B | 1.83 | 440.2 |
| 3-07 | 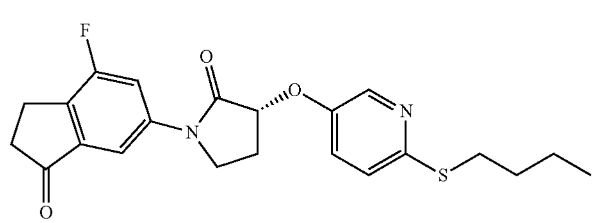 [SMILES: CCCCSc1ccc(O[C@@H]2CCN(c3cc(F)c4c(c3)C(=O)CC4)C2=O)cn1] | B | 1.95 | 415.2 |

TABLE 3-continued

| Example | Structure | LCMS Method | R$_t$ [min] | ESI$^+$ m/z [amu] |
|---|---|---|---|---|
| 3-08 | 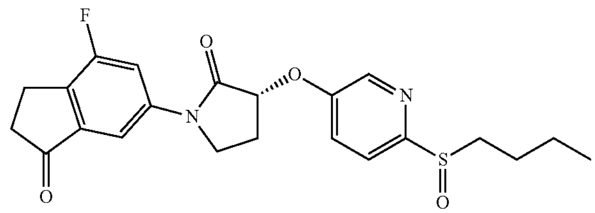 [SMILES: CCCCS(=O)c1ccc(O[C@@H]2CCN(c3cc(F)c4c(c3)C(=O)CC4)C2=O)cn1] | B | 1.66 | 431.2 |
| 3-09 | 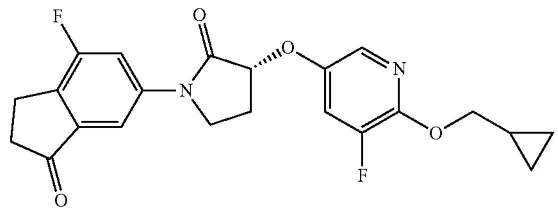 [SMILES: O=C1CCc2c(F)cc(N3CC[C@@H](Oc4cnc(OCC5CC5)c(F)c4)C3=O)cc21] | D | 4.74 | 415.2 |
| 3-10 | 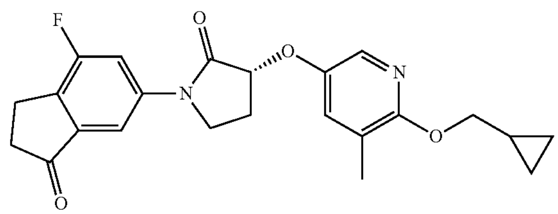 | B | 1.92 | 411.2 |
| 3-11 | 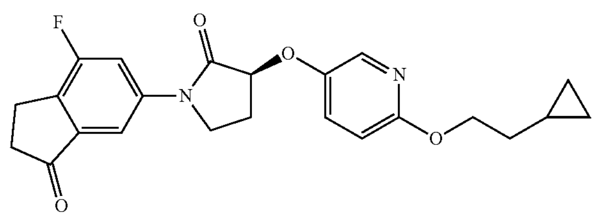 [SMILES: O=C1CCc2c(F)cc(N3CC[C@H](Oc4ccc(OCCC5CC5)nc4)C3=O)cc21] | B | 1.91 | 411.2 |
| 3-12 | 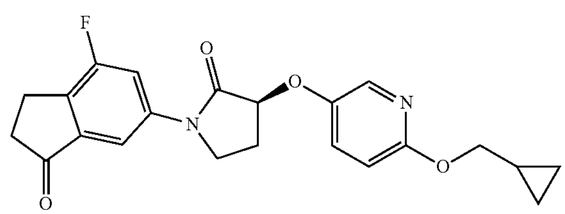 [SMILES: O=C1CCc2c(F)cc(N3CC[C@H](Oc4ccc(OCC5CC5)nc4)C3=O)cc21] | B | 1.79 | 397.2 |
| 3-13 | 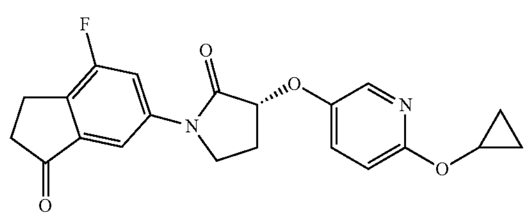 [SMILES: O=C1CCc2c(F)cc(N3CC[C@@H](Oc4ccc(OC5CC5)nc4)C3=O)cc21] | B | 1.67 | 383.2 |
| 3-14 | 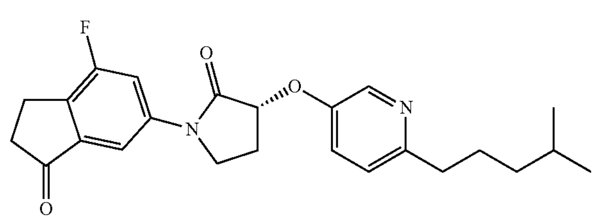 [SMILES: CC(C)CCCc1ccc(O[C@@H]2CCN(c3cc(F)c4c(c3)C(=O)CC4)C2=O)cn1] | B | 1.71 | 411.3 |

TABLE 3-continued

| Example | Structure | LCMS Method | R_t [min] | ESI+ m/z [amu] |
|---|---|---|---|---|
| 3-15 | 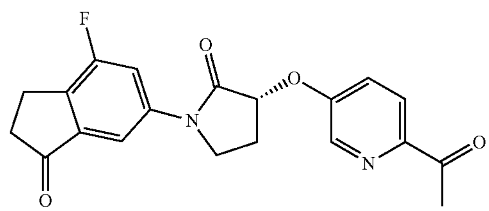 [SMILES: CC(=O)c1ccc(O[C@@H]2CCN(c3cc(F)c4c(c3)C(=O)CC4)C2=O)cn1] | B | 3.96 | 369.1 |
| 3-16 | 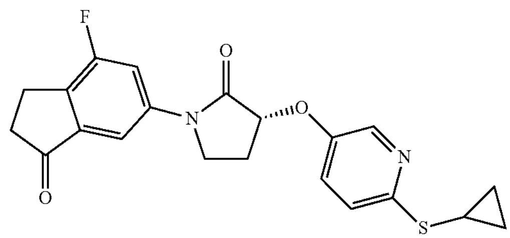 [SMILES: O=C1CCc2c(F)cc(N3CC[C@@H](Oc4ccc(SC5CC5)nc4)C3=O)cc21] | B | 1.73 | 399.3 |
| 3-17 | 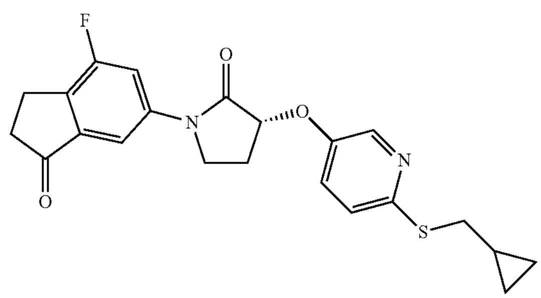 [SMILES: O=C1CCc2c(F)cc(N3CC[C@@H](Oc4ccc(SCC5CC5)nc4)C3=O)cc21] | B | 1.85 | 413.3 |
| 3-18 | 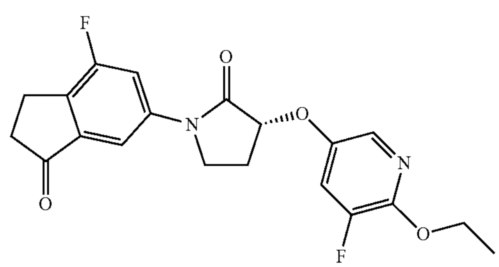 [SMILES: CCOc1ncc(O[C@@H]2CCN(c3cc(F)c4c(c3)C(=O)CC4)C2=O)cc1F] | B | 1.75 | 389.2 |
| 3-19 | 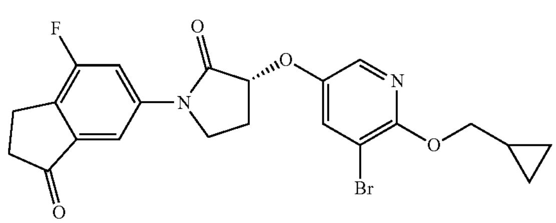 | B | 1.99 | 475.3 |
| 3-20 | 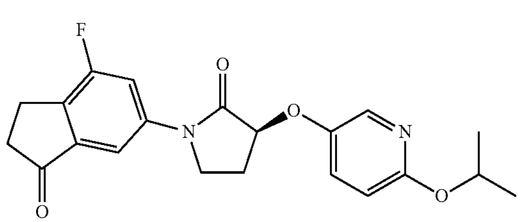 [SMILES: CC(C)Oc1ccc(O[C@H]2CCN(c3cc(F)c4c(c3)C(=O)CC4)C2=O)cn1] | B | 1.78 | 385.2 |

| Example | Structure | LCMS Method | $R_t$ [min] | ESI⁺ m/z [amu] |
|---|---|---|---|---|
| 3-21 | 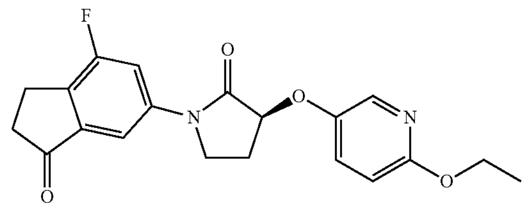 [SMILES: CCOc1ccc(O[C@H]2CCN(c3cc(F)c4c(c3)C(=O)CC4)C2=O)cn1] | B | 1.69 | 371.2 |

Alternative Preparation of (R)-3-(6-Cyclopropoxy-pyridin-3-yloxy)-1-(7-fluoro-3-oxo-indan-5-yl)-pyrrolidin-2-one (Example 3-13)

To a mixture of (S)-1-(7-fluoro-3-oxo-2,3-dihydro-1H-inden-5-yl)-3-hydroxy-pyrrolidin-2-one (80 mg), 6-cyclopropoxy-pyridine-3-ol (53.4 mg), triphenylphosphine (polymer, 126 mg) and THF (1.5 mL) was added DIAD (97 mg). The mixture was shaken for 2 hours and filtered. The filtrate was concentrated and the residue purified by preparative HPLC to provide Example 3-13. ¹H-NMR (400 MHz, DMSO) δ 8.02 (1H, d, J=3.1 Hz), 7.99 (1H, d, J=11.1 Hz), 7.78 (1H, s), 7.55 (1H, dd, J=9.0, 3.1 Hz), 6.83 (1H, d, J=9.0 Hz), 5.25 (1H, dd, J=8.3, 8.3 Hz), 4.13 (1H, m), 3.97 (1H, m), 3.86 (1H, m), 3.10 (2H, m), 2.72 (2H, m), 2.70 (1H, m), 2.14 (1H, m), 0.74 (2H, m), 0.64 (2H, m).

Preparation of 1-(7-Fluoro-3-oxo-indan-5-yl)-3-hydroxy-pyrrolidin-2-ones

(S)-1-(7-Fluoro-3-oxo-indan-5-yl)-3-hydroxy-pyrrolidin-2-one

A mixture of 6-bromo-4-fluoro-indan-1-one (Enamine, 453 mg), (S)-3-hydroxy-pyrrolidin-2-one (200 mg) and 1,4-dioxane (3 mL) was purged with argon. Cesium carbonate (645 mg), N,N'-dimethyl-ethylene-diamine (2.24 mL) and copper(I) iodide (38 mg) were added and the mixture was heated to 80° C. for 3 hours. After cooling to r.t. the mixture was filtered and the filtrate evaporated. The residue was purified by SGC (eluent: heptane/EA 1:1 with 0 to 20% MeOH) to provide the title compound. MS ESI⁺: m/z=250 [M+H]⁺.

(R)-1-(7-Fluoro-3-oxo-indan-5-yl)-3-hydroxy-pyrrolidin-2-one

Reaction of (S)-1-(7-fluoro-3-oxo-indan-5-yl)-3-hydroxy-pyrrolidin-2-one with chloro-acetic acid (Typical Procedure 3) provided the expected ester, which was treated with 3 equivalents of triethylamine in MeOH/water (1:1) to provide the title compound. MS ESI⁺: m/z=250 [M+H]⁺. Alternatively the title compound can be obtained from the reaction of 6-bromo-4-fluoro-indan-1-one with (R)-3-hydroxy-pyrrolidin-2-one following Typical Procedure 1 as exemplified for (S)-1-(7-Fluoro-3-oxo-indan-5-yl)-3-hydroxy-pyrrolidin-2-one (see above).

Preparation of Hydroxy-pyridines

6-(5-Methylthiazol-2-yl)pyridin-3-ol

A solution of 2-(5-(4-methoxybenzyloxy)pyridin-2-yl)-5-methylthiazole (2.0 g) in TFA (10 mL) was stirred at 80° C. for 2 hours. After the reaction was complete, the mixture was evaporated. The residue was purified by chromatography (silica gel, EA/PE 1:2 to EA) to provide the title compound. MS ESI⁺: m/z=193 [M+H]⁺.

2-(5-(4-Methoxybenzyloxy)pyridin-2-yl)-5-methylthiazole

A mixture was prepared from 2-bromo-5-(4-methoxybenzyloxy)pyridine (2.0 g), 5-methylthiazole (614 mg), Pd(P(t-Bu)₃)₂ (253 mg), Cs₂CO₃ (2.02 g) and DMF (10 mL). The system was evacuated and refilled with nitrogen three times. The mixture was stirred at 150° C. under N₂ atmosphere for 3 hours. After cooling, insoluble material was removed by filtration over Celite. The resulting solution was added water (100 mL). The precipitate obtained was filtered off and washed with MeOH three times to provide the subtitle compound. MS ESI⁺: m/z=313 [M+H]⁺.

6-(3-Isopropyl-[1,2,4]oxadiazol-5-yl)-pyridin-3-ol

To DMSO (25 mL) was added 5-hydroxy-pyridine-2-carboxylic acid (1.0 g) and CDI (1.3 g). After 15 minutes N-hydroxy-isobutyramidine (820 mg) was added. After 1 hour the mixture was heated to 90° C. for 1 hour. After the mixture reached room temperature, it was diluted with EA and washed three times with HCl (0.1 M). The organic phase was dried (Na₂SO₄) and concentrated to provide the title compound. MS ESI⁺: m/z=206 [M+H]⁺.

5-Hydroxy-pyridine-2-carboxylic acid cyclopropylmethyl ester (Typical Procedure 9)

To DMF (10 mL) was added 5-hydroxy-pyridine-2-carboxylic acid (1.0 g) followed by EDC (1.38 g), HOBt (971 mg) and DIPEA (1.22 mL). After 15 minutes cyclopropylmethanol (520 mg) was added. After 12 hours the mixture was diluted with water and extracted three times with EA. The combined organic phases were washed with brine, dried (Na₂SO₄) and concentrated to provide the title compound. MS ESI⁺: m/z=194 [M+H]⁺.

(5-Hydroxy-pyridin-2-yl)-pyrrolidin-1-yl-methanone

Typical Procedure 9 was followed. Coupling of 5-hydroxy-pyridine-2-carboxylic acid with pyrrolidine provided the title compound. MS ESI⁺: m/z=193 [M+H]⁺.

5-Hydroxy-pyridine-2-carboxylic acid butyl-methyl-amide

Typical Procedure 9 was followed. Coupling of 5-hydroxy-pyridine-2-carboxylic acid with butyl-methyl-amine provided the title compound. MS ESI⁺: m/z=210 [M+H]⁺.

6-Butylsulfanyl-pyridin-3-ol and 6-(Butane-1-sulfinyl)-pyridin-3-ol

Typical Procedure 4 was followed to convert 5-bromo-2-butylsulfanyl-pyridine into the corresponding boronate.

Typical Procedure 5a: The crude boronate (1.03 g) was mixed with THF/water (1:3, 10 mL) and sodium perborate tetrahydrate (1.0 g) was added. After 1 hour the mixture was adjusted to pH 5-6 by addition of HCl (0.1 M) and extracted three times with EA. The combined organic phases were washed with brine, dried ($Na_2SO_4$) and concentrated. The residue was separated by preparative HPLC to provide both of the title compounds. MS ESI$^+$: m/z=184 [M+H]$^+$ and m/z=200 [M+H]$^+$ respectively.

5-Bromo-2-butylsulfanyl-pyridine

A mixture of 5-bromo-2-chloro-pyridine (2.0 g), 1-butanethiol (1.3 mL), cesium carbonate (4.5 g) and DMF (5 mL) was heated to 60° C. for 3 hours. The mixture was diluted with water and extracted three times with EA. The combined organic phases were washed with brine, dried ($Na_2SO_4$) and concentrated to provide the subtitle compound. MS ESI$^+$: m/z=246 [M+H]$^+$.

6-(Cyclopropylmethylthio)pyridin-3-ol

Typical Procedures 4 and 5a were followed to convert 5-bromo-2-(cyclopropylmethylthio)pyridine to the title compound. MS ESI$^+$: m/z=182 [M+H]$^+$.

5-Bromo-2-(cyclopropylmethylthio)pyridine

To a solution of 5-bromopyridine-2-thiol (3.9 g) in THF (100 mL) was added NaH (1.24 g) at 0° C. and the mixture was stirred at 0° C. for 0.5 h. Then (bromomethyl)cyclopropane (2.79 g) was added. The mixture was allowed to warm to r.t. and stirred for 6 hours. The mixture was poured into ice water (200 mL) and extracted with EA (100 mL×3). The combined organic phases were washed with brine (50 mL) and then dried over $Na_2SO_4$. After filtration and evaporation of the solvent, the residue was purified by SGC (eluent: PE) to provide the subtitle compound. MS ESI$^+$: m/z=244 [M+H]$^+$.

6-(Cyclopropylthio)pyridin-3-ol

Typical Procedures 4 and 5a were followed to convert 5-bromo-2-(cyclopropylthio)pyridine to the title compound. MS ESI$^+$: m/z=168 [M+H]$^+$.

5-Bromo-2-(cyclopropylthio)pyridine

To a suspension of NaH (60% in mineral oil, 2.40 g) in THF (100 mL) was added dropwise cyclopropanethiol (0.25 M in $Et_2O$, 160 mL) at 0° C. After stirring for 30 min, 5-bromo-2-fluoropyridine (3.52 g) was added in portions at 0° C. and then warmed to r.t. slowly. The reaction mixture was stirred at r.t. overnight. The reaction mixture was quenched with water (30 mL) and extracted with ethyl acetate (50 mL×3). The combined organic layers were washed with brine (50 mL) and dried over $Na_2SO_4$. After filtration and evaporation of the solvent, the crude product was obtained and used in next step without further purification.

MS ESI$^+$: m/z=230 [M+H]$^+$.

6-Cyclopropylmethoxy-5-fluoro-pyridin-3-ol

Following Typical Procedures 4 and 5a, conversion of 5-bromo-2-cyclopropylmethoxy-3-fluoro-pyridine to the boronate and oxidation with NaBO3 provided the title compound.

MS ESI$^+$: m/z=184 [M+H]$^+$.

5-Bromo-2-cyclopropylmethoxy-3-fluoro-pyridine

Following Typical Procedure 6, reaction of 5-bromo-2,3-difluoro-pyridine with cyclopropyl-methanol provided the subtitle compound. MS ESI$^+$: m/z=246 [M+H]$^+$.

6-Ethoxy-5-fluoro-pyridin-3-ol

Following the procedures given for 6-cyclopropylmethoxy-5-fluoro-pyridin-3-ol, the title compound was obtained starting with 5-bromo-2,3-difluoro-pyridine and ethanol. MS ESI$^+$: m/z=158 [M+H]$^+$.

6-Ethoxy-pyridin-3-ol

Following the procedures given for 6-cyclopropylmethoxy-5-fluoro-pyridin-3-ol, the title compound was obtained starting with 5-bromo-2-fluoro-pyridine and ethanol. MS ESI$^+$: m/z=140 [M+H]$^+$.

6-Isopropoxy-pyridin-3-ol

Following the procedures given for 6-cyclopropylmethoxy-5-fluoro-pyridin-3-ol, the title compound was obtained starting with 5-bromo-2-fluoro-pyridine and isopropanol. MS ESI$^+$: m/z=154 [M+H]$^+$.

5-Bromo-6-(cyclopropylmethoxy)pyridin-3-ol

To a solution of 3-bromo-2-(cyclopropylmethoxy)-5-iodopyridine (12.5 g) in dry THF (300 mL) was added i-PrMgCl*LiCl (30 mL, 38.3 mmol) dropwise at 0° C. The mixture was stirred at 0° C. for 20 min and then B(OMe)$_3$ (5.5 g) was added at 0° C. The mixture was allowed to warm to r.t. and stirred for 3 h. The mixture was quenched by the addition of brine (50 mL). The organic phase was separated and the aqueous phase was extracted with EA (50 mL×3). The organic phases were combined and the solvent was removed under reduced pressure. The residue was treated according Typical Procedure 5a to obtain the title compound. MS ESI$^+$: m/z=244 [M+H]$^+$.

3-Bromo-2-(cyclopropylmethoxy)-5-iodopyridine

To a suspension of NaH (60% in mineral oil, 4.32 g) in THF (300 mL) was added cyclopropylmethanol (5.83 g) at 0° C. and the mixture was stirred for 30 min at 0° C. A solution of 3-bromo-2-fluoro-5-iodopyridine (16.3 g) in THF (50 mL) was added to the suspension at 0° C. The suspension was allowed to warm to r.t. and stirred for 18 h. The suspension was poured into ice water and then extracted with EA (200 mL×3). The combined organic layers were washed with brine and dried over $Na_2SO_4$. After filtration and evaporation of the solvent, the residue was purified by SGC (eluent: PE) to give the subtitle compound. MS ESI$^+$: m/z=354 [M+H]$^+$.

6-Cyclopropylmethoxy-5-methyl-pyridin-3-ol

Following Typical Procedures 4 and 5a, conversion of 5-bromo-2-cyclopropylmethoxy-3-methyl-pyridine to the boronate and oxidation with NaBO₃ provided the title compound. MS ESI⁺: m/z=180 [M+H]⁺.

5-Bromo-2-cyclopropylmethoxy-3-methyl-pyridine

Following Typical Procedure 6, reaction of 5-bromo-2,3-difluoro-pyridine with cyclopropyl-methanol provided the subtitle compound. MS ESI⁺: m/z=242 [M+H]⁺.

6-(4-Methyl-pentyl)-pyridin-3-ol

Typical Procedure 7 was followed. Hydrogenation of 5-(4-methylpent-1-yn-1-yl)pyridin-2-ol over Pd/C provided the title compound. MS ESI⁺: m/z=180 [M+H]⁺.

5-(4-Methylpent-1-yn-1-yl)pyridin-2-ol

To a mixture of 6-bromo-pyridin-3-ol (1.0 g), 4-methyl-pent-1-yne (872 µL) and DMF (5 mL) under argon was added cesium carbonate (3.28 g), CuI (137 mg) and Pd(dppf)Cl₂. The mixture was heated to 80° C. for 4 hours. After reaching room temperature the mixture was filtered and concentrated. The residue was purified by chromatography (silica gel, EA/heptane 1:1 to EA/heptane/MeOH 9:9:2) to provide the subtitle compound. MS ESI⁺: m/z=176 [M+H]⁺.

1-(5-Hydroxy-pyridin-2-yl)-ethanone

Typical Procedure 7 was followed. Hydrogenation of 1-(5-benzyloxy-pyridin-2-yl)-ethanone over Pd/C at ambient pressure provided the title compound. MS ESI⁺: m/z=138 [M+H]⁺.

1-(5-Benzyloxy-pyridin-2-yl)-ethanone

A mixture of 5-benzyloxy-2-bromo-pyridine (1.0 g), N-methoxy-N-methyl-acetamide (780 mg) and THF (20 mL) under argon at −60° C. was added n-BuLi (2.6 M in toluene, 2.9 mL). After 1 hour the cooling bath was removed. After reaching room temperature the mixture was quenched by addition of saturated NH₄Cl-solution. The mixture was distributed between EA and brine. The organic phase was dried (Na₂SO₄), filtered and concentrated. The residue was purified by chromatography (silica gel, heptane to EA/heptane 3:7) to provide the subtitle compound. MS ESI⁺: m/z=228 [M+H]⁺.

Preparation of Examples 4

TABLE 4

| Example | Structure | LCMS Method | R_t [min] | ESI⁺ m/z [amu] |
|---------|-----------|-------------|-----------|----------------|
| 4-01 | 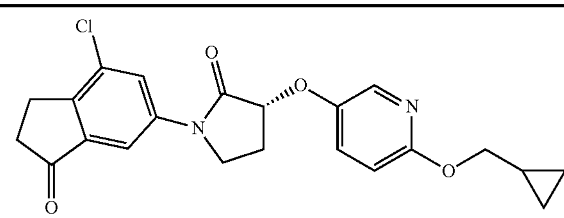 | B | 1.88 | 413.2 |
| 4-02 | 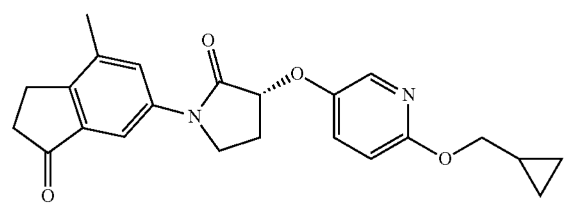 [SMILES: Cc1cc(N2CC[C@@H](Oc3ccc(OCC4CC4)nc3)C2=O)cc2c1CCC2=O] | B | 1.80 | 393.3 |
| 4-03 | 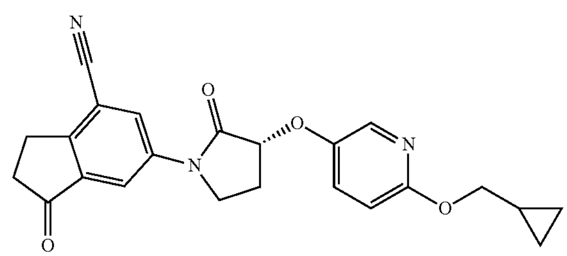 [SMILES: N#Cc1cc(N2CC[C@@H](Oc3ccc(OCC4CC4)nc3)C2=O)cc2c1CCC2=O] | D | 4.47 | 404.2 |

Example 4-01

A mixture of (R)-1-(7-bromo-3-oxo-indan-5-yl)-3-(6-cyclopropylmethoxy-pyridin-3-yloxy)-pyrrolidin-2-one (50 mg), nickel(II) chloride (140 mg) and DMF (1 mL) was heated in a microwave instrument to 170° C. for 10 minutes. The cooled mixture was separated by preparative HPLC to provide Example 4-01.

Example 4-02

A mixture of (R)-1-(7-bromo-3-oxo-indan-5-yl)-3-(6-cyclopropylmethoxy-pyridin-3-yloxy)-pyrrolidin-2-one (52 mg), trimethyl boroxine (3.5 M in water, 32 µL), Pd(dppf)Cl₂

(83 mg), potassium carbonate (18 mg) and 1,4-dioxane/water (5:1; 1.5 mL) under argon was heated in a microwave instrument to 130° C. for 30 minutes. The cooled mixture was filtered and the filtrate separated by preparative HPLC to provide Example 4-02.

Example 4-03

A mixture of (R)-1-(7-bromo-3-oxo-indan-5-yl)-3-(6-cyclopropylmethoxy-pyridin-3-yloxy)-pyrrolidin-2-one (50 mg), zinc(II) cyanide (26 mg) and DMF (0.25 mL) was purged with argon. To the vial Pd(dppf)Cl$_2$ (10 mg) and Pd$_2$dba$_3$ (10 mg) were added and it was heated in a microwave instrument to 120° C. for 1 hour. The cooled mixture was filtered and the filtrate separated by preparative HPLC to provide Example 4-03.

Preparation of Examples 5

Example 5-01 (Typical Procedure 10)

A mixture of (R)-3-(2-bromo-pyridin-4-yloxy)-1-(7-fluoro-3-oxo-indan-5-yl)-pyrrolidin-2-one (80 mg), 2-cyclopropyl-ethanol (85 mg), cesium carbonate (129 mg) and toluene (1.6 mL) under argon was added Pd(OAc)$_2$ (443 µg) and 5-(di-tert-butylphosphino)-1',3',5'-triphenyl-1'H-[1,4']bipyrazole (2.0 mg). The mixture was heated to 90° C. for 2 hours by microwave irradiation. After cooling to room temperature the mixture was filtered and concentrated. The residue was purified by preparative HPLC to provide Example 5-01. Following Typical Procedure 10, the examples in Table 5 were obtained by reacting (R)-3-(2-bromo-pyridin-4-yloxy)-1-(7-fluoro-3-oxo-indan-5-yl)-pyrrolidin-2-one with the respective alcohols.

TABLE 5

| Example | Structure | LCMS Method | R$_t$ [min] | ESI$^+$ m/z [amu] |
|---|---|---|---|---|
| 5-01 | 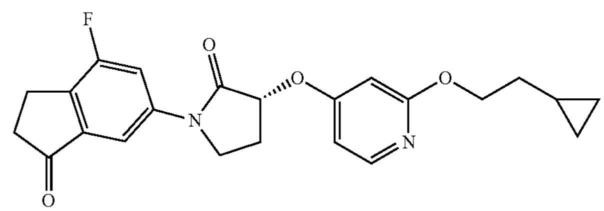 [SMILES: O=C1CCc2c(F)cc(N3CC[C@@H](Oc4ccnc(OCCC5CC5)c4)C3=O)cc21] | B | 1.80 | 411.2 |
| 5-02 | 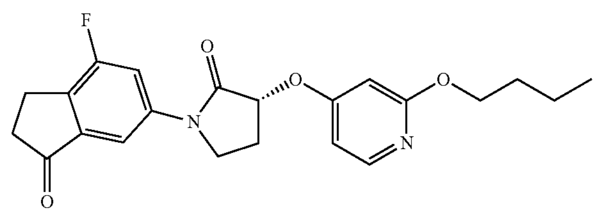 [SMILES: CCCCOc1cc(O[C@@H]2CCN(c3cc(F)c4c(c3)C(=O)CC4)C2=O)ccn1] | B | 1.79 | 399.2 |
| 5-03 | 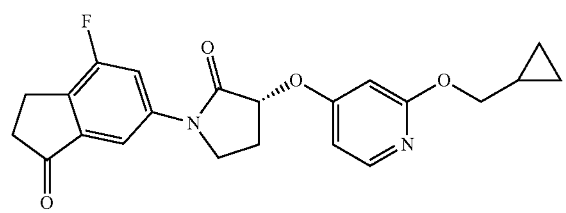 [SMILES: O=C1CCc2c(F)cc(N3CC[C@@H](Oc4ccnc(OCC5CC5)c4)C3=O)cc21] | B | 1.71 | 397.2 |
| 5-04 | 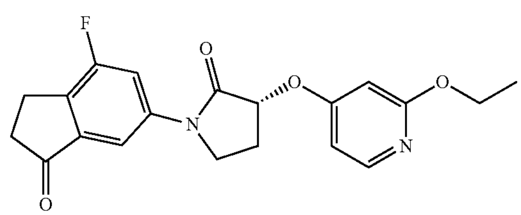 [SMILES: CCOc1cc(O[C@@H]2CCN(c3cc(F)c4c(c3)C(=O)CC4)C2=O)ccn1] | D | 3.50 | 371.2 |
| 5-05 | 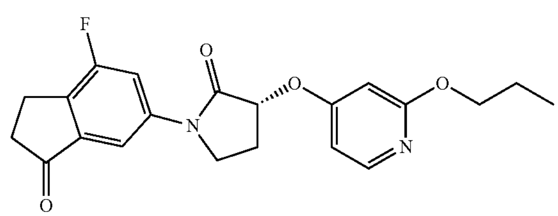 [SMILES: CCCOc1cc(O[C@@H]2CCN(c3cc(F)c4c(c3)C(=O)CC4)C2=O)ccn1] | D | 3.89 | 385.2 |

TABLE 5-continued

| Example | Structure | LCMS Method | R$_t$ [min] | ESI$^+$ m/z [amu] |
|---------|-----------|-------------|-------------|-------------------|
| 5-06 | 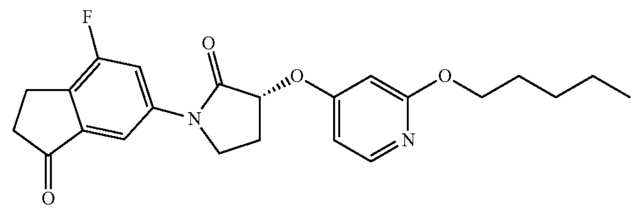 [SMILES: CCCCCOc1cc(O[C@@H]2CCN(c3cc(F)c4c(c3)C(=O)CC4)C2=O)ccn1] | B | 1.88 | 413.3 |
| 5-07 | 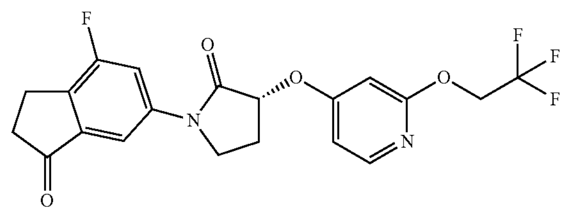 [SMILES: O=C1CCc2c(F)cc(N3CC[C@@H](Oc4ccnc(OCC(F)(F)F)c4)C3=O)cc21] | B | 1.81 | 425.1 |
| 5-08 | 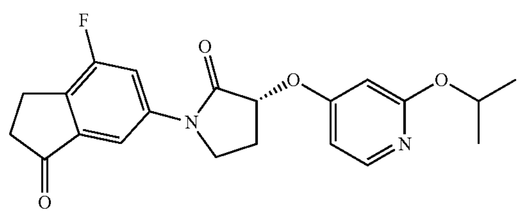 [SMILES: CC(C)Oc1cc(O[C@@H]2CCN(c3cc(F)c4c(c3)C(=O)CC4)C2=O)ccn1] | B | 1.62 | 385.2 |
| 5-09 | 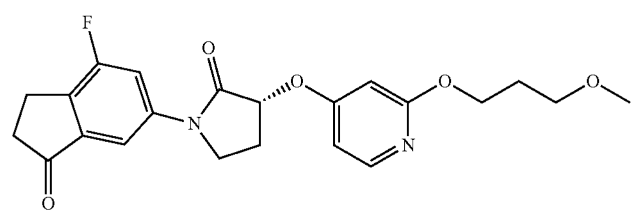 [SMILES: COCCCOc1cc(O[C@@H]2CCN(c3cc(F)c4c(c3)C(=O)CC4)C2=O)ccn1] | B | 1.57 | 415.2 |
| 5-10 | 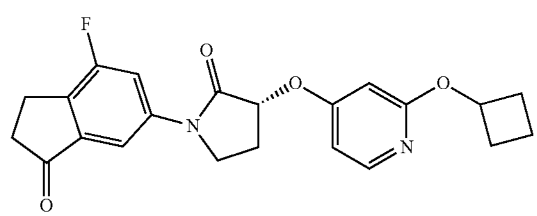 [SMILES: O=C1CCc2c(F)cc(N3CC[C@@H](Oc4ccnc(OC5CCC5)c4)C3=O)cc21] | B | 1.68 | 397.2 |

60

(R)-3-(2-Bromo-pyridin-4-yloxy)-1-(7-fluoro-3-oxo-indan-5-yl)-pyrrolidin-2-one

Typical Procedure 3 was followed. Reaction of (S)-1-(7-fluoro-3-oxo-indan-5-yl)-3-hydroxy-pyrrolidin-2-one with 2-bromo-pyridin-4-ol provided the title compound. MS ESI$^+$: m/z=405 [M+H]$^+$.

Preparation of Example 6-01 and Example 7-01

TABLE 6

| Example | Structure | LCMS Method | R$_t$ [min] | ESI$^+$ m/z [amu] |
|---|---|---|---|---|
| 6-01 | 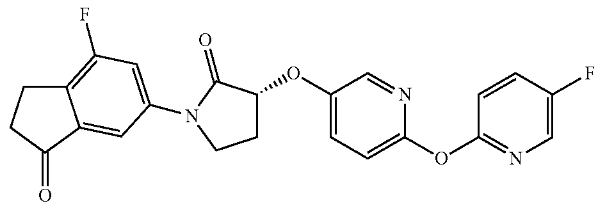 [SMILES: O=C1CCc2c(F)cc(N3CC[C@@H](Oc4ccc(Oc5ccc(F)cn5)nc4)C3=O)cc21] | B | 1.66 | 438.2 |
| 7-01 | 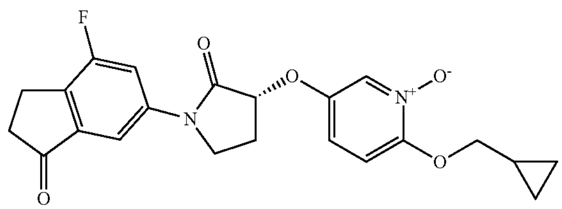 [SMILES: O=C1CCc2c(F)cc(N3CC[C@@H](Oc4ccc(OCC5CC5)[n+]([O-])c4)C3=O)cc21] | B | 1.42 | 413.3 |

Example 6-01

A mixture of (R)-1-(7-fluoro-3-oxo-2,3-dihydro-1H-inden-5-yl)-3-((6-hydroxypyridin-3-yl)oxy)pyrrolidin-2-one (300 mg), 2,5-difluoropyridine (192 mg), cesium carbonate (350 mg) and DMF (2 mL) was heated to 80° C. for 1 hour. The reaction mixture was filtered and separated by preparative HPLC to provide Example 6-01.

Example 7-01

A mixture of (R)-3-((6-(cyclopropylmethoxy)pyridin-3-yl)oxy)-1-(7-fluoro-3-oxo-2,3-dihydro-1H-inden-5-yl)pyrrolidin-2-one (80 mg), 3-chloro-perbenzoic acid (54 mg) and 1,2-dichlorethane (1 mL) was stirred for 72 hours. The solvent was removed. The residue was purified preparative HPLC to provide Example 7-01.

Preparation of Examples 8

TABLE 7

| Example | Structure | LCMS Method | R$_t$ [min] | ESI$^+$ m/z [amu] |
|---|---|---|---|---|
| 8-01 | 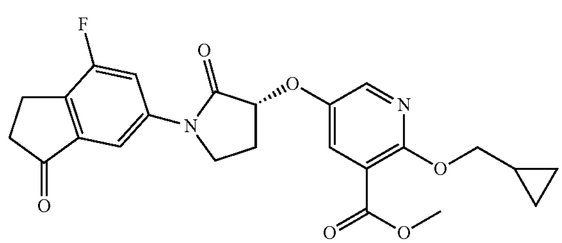 [SMILES: COC(=O)c1cc(O[C@@H]2CCN(c3cc(F)c4c(c3)C(=O)CC4)C2=O)cnc1OCC1CC1] | B | 1.82 | 455.2 |

TABLE 7-continued

| Example | Structure | LCMS Method | R_t [min] | ESI+ m/z [amu] |
|---|---|---|---|---|
| 8-02 | 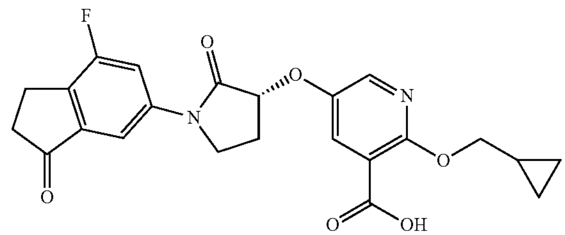 [SMILES: O=C(O)c1cc(O[C@@H]2CCN(c3cc(F)c4c(c3)C(=O)CC4)C2=O)cnc1OCC1CC1] | B | 1.68 | 441.1 |
| 8-03 | 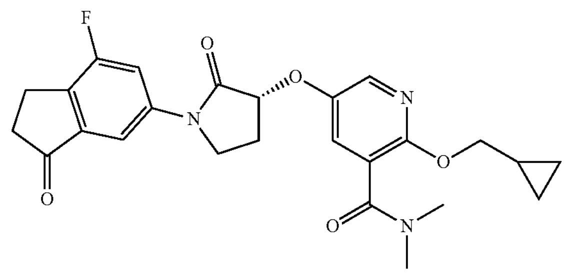 [SMILES: CN(C)C(=O)c1cc(O[C@@H]2CCN(c3cc(F)c4c(c3)C(=O)CC4)C2=O)cnc1OCC1CC1] | B | 1.73 | 468.3 |
| 8-04 | 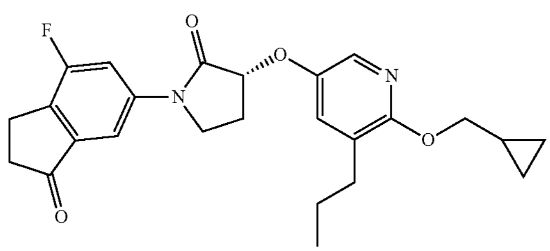 [SMILES: CCCc1cc(O[C@@H]2CCN(c3cc(F)c4c(c3)C(=O)CC4)C2=O)cnc1OCC1CC1] | B | 2.00 | 439.2 |
| 8-05 | 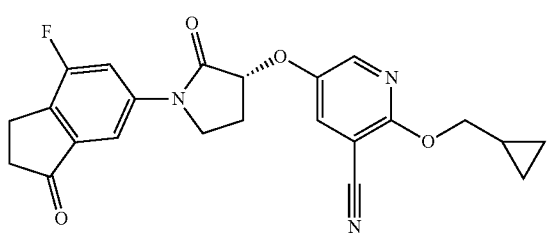 [SMILES: N#Cc1cc(O[C@@H]2CCN(c3cc(F)c4c(c3)C(=O)CC4)C2=O)cnc1OCC1CC1] | B | 1.83 | 422.1 |

Example 8-01

To a mixture of (R)-3-((5-bromo-6-(cyclopropylmethoxy)pyridin-3-yl)oxy)-1-(7-fluoro-3-oxo-2,3-dihydro-1H-inden-5-yl)pyrrolidin-2-one (0.50 g), DMF (5 mL), methanol (0.85 mL) and triethylamine (0.3 mL) under argon was added Pd(dppf)Cl$_2$ (0.23 g). The mixture was stirred under a carbon monoxide atmosphere (5 atm, 70° C., 15 h). After cooling to r.t. and pressure release, the mixture was distributed between EA and water. The organic phase was washed (two times with water and with brine), dried (Na$_2$SO$_4$) and concentrated to give a residue which was purified by SGC (eluent: PE with 0 to 65% EA). Example 8-01 was obtained.

Example 8-02

A mixture of Example 8-01 (0.20 g), LiOH (2 M in water, 0.22 mL) and THF (3 mL) was stirred at r.t. for 18 h. Diluted hydrochloric acid was used to adjust the pH to 3-4. The mixture was extracted with EA. The organic phase was concentrated and the residue purified by HPLC to provide Example 8-02.

Example 8-03

To DMF (1 mL) was added Example 8-02 (50 mg) followed by HATU (30 mg) and DIPEA (30 µL). After 30 minutes dimethylamine (2 M in THF, 50 µL) was added. After 1 hour the mixture was directly purified by HPLC to provide Example 8-03.

Example 8-04

To a mixture of Example 8-02 (150 mg) and toluene (7 mL) under argon was added a suspension of propylboronic acid, cesium carbonate and toluene (7 mL). After 30 minutes Pd(PPh$_3$)$_4$ (15 mg) was added and the mixture heated to 95° C. for 12 hours. After cooling to r.t. HCl (1 N) was added and the mixture diluted with EA. The organic layer was washed with sodium bicarbonate solution and filtered over a short pad of silica gel. The filtrate was concentrated and the residue purified by HPLC to provide Example 8-04.

Example 8-05

To a mixture of Example 8-02 (100 mg), zinc cyanide (50 mg) and DMF (1 mL) under argon was added $Pd_2(dba)_3$ (20 mg) and dppf (20 mg). The mixture was heated to 120° C. for 1 hour and to 150° C. for another hour by microwave irradiation. After cooling to r.t. DMF (3 mL) was added and the mixture was filtered. The filtrate was purified by HPLC to provide Example 8-05.

Preparation of Examples 9

6-Bromo-4,7-difluoro-2,3-dihydro-1H-inden-1-ol

To a mixture of 6-bromo-4,7-difluoro-2,3-dihydro-1H-inden-1-one (0.5 g), THF (1 mL) and EtOH (1 mL) was added $NaBH_4$ (100 mg). After 1 hour the reaction mixture was concentrated and the residue distributed between water and EA. The organic phase was washed with water (3 times), dried ($Na_2SO_4$), filtered and concentrated. The residue was purified by preparative HPLC to provide the subtitle compound. MS $ESI^+$: m/z=249 $[M+H]^+$.

6-Bromo-4,7-difluoro-2,3-dihydro-1H-inden-1-one

To a solution of 3-(4-bromo-2,5-difluorophenyl)propanoic acid (1.10 g) in DCM (20 mL) was added $SOCl_2$ (2.45 g). The

TABLE 8

| Example | Structure | LCMS Method | $R_t$ [min] | $ESI^+$ m/z [amu] |
|---|---|---|---|---|
| 9-01 | 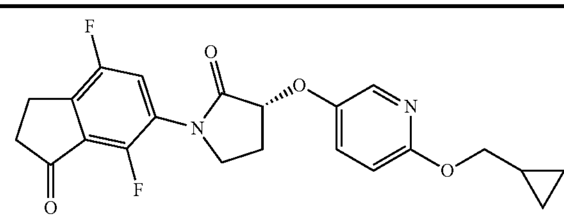 | B | 1.75 | 415.2 |
| 9-02 | 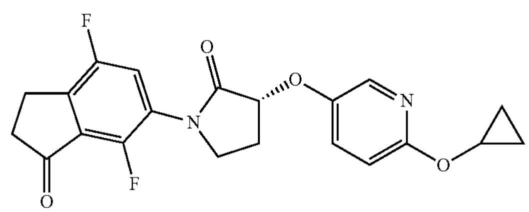 [SMILES: O=C1CCc2c(F)cc(N3CC[C@@H](Oc4ccc(OC5CC5)nc4)C3=O)c(F)c21] | B | 1.60 | 401.1 |
| 9-03 | 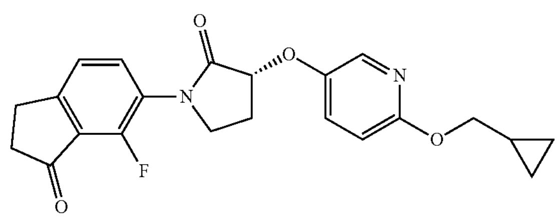 [SMILES: O=C1CCc2ccc(N3CC[C@@H](Oc4ccc(OCC5CC5)nc4)C3=O)c(F)c21] | B | 1.68 | 397.1 |

Example 9-01

A mixture of (3R)-3-((6-(cyclopropylmethoxy)pyridin-3-yl)oxy)-1-(4,7-difluoro-3-hydroxy-2,3-dihydro-1H-inden-5-yl)pyrrolidin-2-one (96 mg), DCM (3 mL) and $MnO_2$ (236 mg) was stirred at r.t. for 5 days. After filtration the mixture was concentrated and purified by HPLC to provide Example 9-01.

(3R)-3-((6-(cyclopropylmethoxy)pyridin-3-yl)oxy)-1-(4,7-difluoro-3-hydroxy-2,3-dihydro-1H-inden-5-yl)pyrrolidin-2-one Following Typical Procedure 1 (R)-3-((6-(cyclopropylmethoxy)pyridin-3-yl)oxy)pyrrolidin-2-one was reacted with 6-bromo-4,7-difluoro-2,3-dihydro-1H-inden-1-ol to provide the subtitle compound. MS $ESI^+$: m/z=417 $[M+H]^+$.

mixture was stirred at room temperature for 18 hours. The solvent was removed by evaporation under reduced pressure. The residue was dried under high vacuum to give a crude solid. To the residue was added $AlCl_3$ (2.76 g) and the mixture heated to 130° C. The mixture was stirred at 130° C. for 2 hours and then cooled to room temperature. The resulting mixture was treated with ice water and then extracted with ethyl acetate (50 mL×3). The organic phase was washed with brine, dried over $Na_2SO_4$, and concentrated. The residue was purified by silica gel column chromatography eluting with petroleum ether/ethyl acetate (5:1) to give the subtitle compound as a light yellow solid. MS $ESI^+$: m/z=247 $[M+H]^+$.

3-(4-Bromo-2,5-difluorophenyl)propanoic acid

To a solution of 3-(4-bromo-2,5-difluorophenyl)acrylic acid (4.20 g) in THF was added chlorotris-(triphenylphosphine)rhodium (400 mg). The mixture was stirred at room temperature under $H_2$-atmosphere for 48 hours. The mixture was filtered and the filtrate was concentrated. The residue was purified by silica gel column chromatography eluting with DCM/petroleum ether (7:1) to give the subtitle compound as a white solid. MS ESI$^+$: m/z=265 [M+H]$^+$.

3-(4-Bromo-2,5-difluorophenyl)acrylic acid

To a solution of 4-bromo-2,5-difluorobenzaldehyde (15.0 g) in triethylamine formiate (80 mL) at room temperature was added 2,2-dimethyl-1,3-dioxane-4,6-dione (9.77 g). After being stirred for 1 h, the mixture was heated at 95° C. with stirring for 15 hours. After cooling down, ice water was added. The mixture was adjusted to pH ~1 with HCl (6 M) and then extracted with ethyl acetate (200 mL×3). The organic phase was washed with brine (50 mL) and dried over Na$_2$SO$_4$. The solvent was removed under reduced pressure and the residue was purified by silica gel column chromatography eluting with DCM/petroleum ether (7:1) to give the subtitle compound as a white solid. MS ESI$^+$: m/z=263 [M+H]$^+$.

Example 9-02

A mixture of (3R)-3-((6-(cyclopropoxy)pyridin-3-yl)oxy)-1-(4,7-difluoro-3-hydroxy-2,3-dihydro-1H-inden-5-yl)pyrrolidin-2-one (230 mg), DCM (10 mL) and Dess-Martin periodinane (495 mg) was stirred at r.t. for 2 hours. The residue obtained after concentration was purified by HPLC to provide Example 9-02.

(3R)-3-((6-(Cyclopropyl methoxy)pyridin-3-yl)oxy)-1-(4,7-difluoro-3-hydroxy-2,3-dihydro-1H-inden-5-yl)pyrrolidin-2-one Following Typical Procedure 1 (R)-3-((6-(cyclopropoxy)pyridin-3-yl)oxy)pyrrolidin-2-one was reacted with 6-bromo-4,7-difluoro-2,3-dihydro-1H-inden-1-ol to provide the subtitle compound. MS ESI$^+$: m/z=403 [M+H]$^+$.

Example 9-03

A mixture of (3R)-3-((6-(cyclopropylmethoxy)pyridin-3-yl)oxy)-1-(4-fluoro-3-hydroxy-2,3-dihydro-1H-inden-5-yl)pyrrolidin-2-one (50 mg), DCM (5 mL) and Dess-Martin periodinane (53 mg) was stirred at r.t. for 12 hours. The residue obtained after concentration was purified by HPLC to provide Example 9-03.

(3R)-3-((6-(Cyclopropylmethoxy)pyridin-3-yl)oxy)-1-(4-fluoro-3-hydroxy-2,3-dihydro-1H-inden-5-yl)pyrrolidin-2-one Following Typical Procedure 1 (R)-3-((6-(cyclopropylmethoxy)pyridin-3-yl)oxy)pyrrolidin-2-one was reacted with 6-bromo-4-fluoro-2,3-dihydro-1H-inden-1-ol to provide the subtitle compound. MS ESI$^+$: m/z=399 [M+H]$^+$.

6-Bromo-4-fluoro-2,3-dihydro-1H-inden-1-ol

To a solution of 6-bromo-7-fluoro-2,3-dihydro-1H-inden-1-one (620 mg) in THF (20 mL) was added LiAlH$_4$ (103 mg) in portions at 0° C. and the mixture was stirred at 0° C. for 0.5 h. The mixture was quenched by the addition of brine (10 mL), and the aqueous phase was extracted with EA (10 mL×3). The combined organic phases were dried over Na$_2$SO$_4$. After filtration and evaporation of the solvent, the residue obtained was purified by reverse phase chromatography eluting with H$_2$O/MeCN (0.01% NH$_4$HCO$_3$, 5% to 60% within 20 min) to give the subtitle compound. MS ESI$^+$: m/z=231 [M+H]$^+$.

6-Bromo-7-fluoro-2,3-dihydroinden-1-one 1-(3-Bromo-2-fluorophenyl)-3-chloropropan-1-one (3.3 g) was added to a slurry of AlCl$_3$ (16.6 g) and NaCl (4.3 g) at 130° C. The resulting mixture was stirred at 180° C. for 2 hours. The reaction was cooled to r.t. and the residue was dissolved in EA (200 mL). The solution was washed with water (300 mL) and brine (50 mL) and finally dried over Na$_2$SO$_4$. After filtration, the solvent was removed under reduced pressure. The residue was purified by column chromatography on silica gel (eluent: EA/PE 1:10) to provide the subtitle compound. MS ESI$^+$: m/z=229 [M+H]$^+$.

1-(3-Bromo-2-fluorophenyl)-3-chloropropan-1-one

To a solution of 3-bromo-2-fluorobenzoic acid (15 g) in toluene (200 mL) was added SOCl$_2$ (12.2 g) at r.t. and the suspension was heated to reflux with stirring for 2.5 h. The volatiles were removed under reduced pressure. The residue was taken up in DCM (20 mL) and added to a solution of AlCl$_3$ (9.1 g) in dichloroethane at 10-20° C. Ethylene was bubbled through the solution for 4 hours after which the resulting mixture was stirred for 15 hours and then quenched with 4 N HCl (100 mL). The resulting layers were separated and the aqueous phase was extracted with DCM (100 mL×3). The combined organic layers were washed with water (50 mL×3), brine (50 mL) and dried over Na$_2$SO$_4$. After filtration, the solvent was removed under reduced pressure. The residue was purified by column chromatography on silica gel (eluent: DCM/PE 1:200) to provide the subtitle compound. MS ESI$^+$: m/z=265 [M+H]$^+$.

Following the general methods, typical procedures and examples outlined above, the examples in Table 9 were prepared.

TABLE 9

| Example | Structure |
|---|---|
| 9-01 | (structure) |
| 1-19 | (structure) |
| 9-03 | (structure) |

TABLE 9-continued

| Example | Structure |
|---|---|
| 3-16 | 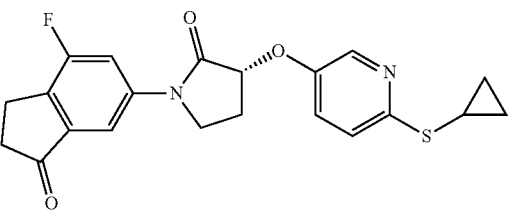 [SMILES: O=C1CCc2c(F)cc(N3CC[C@@H](Oc4ccc(SC5CC5)nc4)C3=O)cc21] |
| 3-17 | 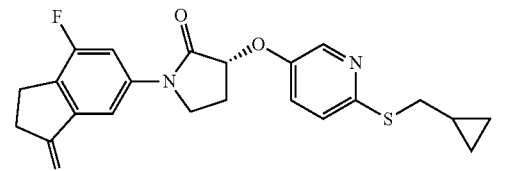 |
| 8-05 | 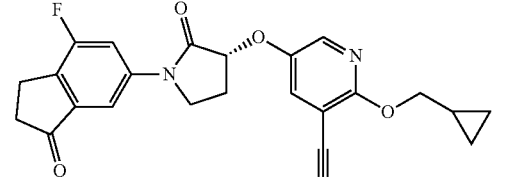 |
| 8-02 | 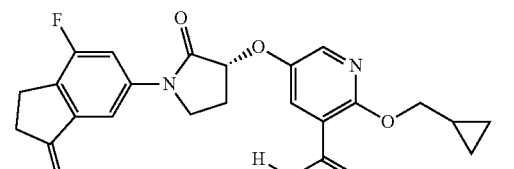 |
| 3-18 | 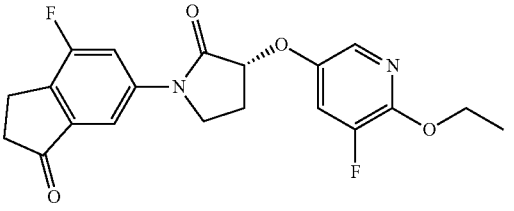 [SMILES: CCOc1ncc(O[C@@H]2CCN(c3cc(F)c4c(c3)C(=O)CC4)C2=O)cc1F] |

Pharmacological Utility

The biological activity of the compounds of the invention may be demonstrated by known in vitro assays. Examples include in vitro cellular assays for recombinant and non-recombinant GPR119 as described in the following.

Functional Cellular Assays Measuring GPR119-Mediated cAMP Release.

Compounds of the invention, which are agonists of GPR119, were characterized by functional assays measuring the cAMP response of HEK-293 cell lines stably expressing recombinant GPR119 from man, mouse or rat, or by using a hamster cell line HIT-T15 expressing GPR119 endogenously. The cAMP content was determined using a kit based on homogenous time-resolved fluorescence (HTRF) from Cisbio Corp. (cat. no. 62AM4PEC). For preparation, cells were split into T175 culture flasks and grown to near confluency in medium (DMEM/10% FCS for HEK-293 cells, and F-12K medium/10% horse serum/2.5% FCS for HIT-T15 cells, respectively). Medium was then removed and cells washed with PBS lacking calcium and magnesium ions, followed by proteinase treatment with accutase (Sigma-Aldrich, cat. no. A6964). Detached cells were washed and resuspended in assay buffer (1×HBSS; 20 mM HEPES, 0.1% BSA, 2 mM IBMX) and cellular density determined. They were then diluted to 400000 cells/mL and 25 µL-aliquots dispensed to the wells of 96-well plates. For measurement, 25 µL of test compound in assay buffer was added and incubated for 30 minutes at room temperature. After addition of HTRF reagents diluted in lysis buffer, the plates were incubated for 1 hour, followed by measuring the fluorescence ratio at 665 vs. 620 nm. Potency of the agonists was quantified by determining the concentrations that caused 50% of the maximal response/activation ($EC_{50}$). See Table 10 for exemplary data obtained using the cell line expressing human GPR119.

Compounds of the invention show $EC_{50}$ values typically in the range of about 0.001 to 100 µM, preferably from about 0.001 to 10 µM, more preferably from about 0.001 to 1 µM and most preferably from about 0.001 to 0.3 µM.

TABLE 10

| Example | $EC_{50}$ [µM] |
|---|---|
| 1-01 | 0.385 |
| 1-02 | 0.895 |
| 1-03 | 0.033 |
| 1-04 | 0.145 |
| 1-05 | 0.045 |
| 1-06 | 0.274 |
| 1-07 | 0.087 |
| 1-08 | 0.008 |
| 1-09 | 0.064 |
| 1-10 | 0.699 |
| 1-11 | 0.008 |
| 1-12 | 0.327 |
| 1-13 | 0.368 |
| 1-14 | 0.033 |
| 1-15 | 0.070 |
| 1-16 | 3.810 |
| 1-17 | 0.039 |
| 1-18 | 0.287 |
| 1-19 | 0.692 |
| 1-20 | 0.087 |
| 2-01 | 0.223 |
| 2-02 | 0.027 |
| 2-03 | 0.063 |
| 2-04 | 0.233 |
| 2-05 | 0.077 |
| 2-06 | 0.018 |
| 2-07 | 0.045 |
| 2-08 | 0.017 |
| 2-09 | 0.016 |
| 2-10 | 0.005 |
| 2-11 | 0.029 |
| 2-12 | 0.099 |
| 2-13 | 0.141 |
| 2-14 | 0.012 |
| 2-15 | 0.289 |
| 2-16 | 0.832 |
| 2-17 | 0.016 |
| 2-18 | 0.005 |
| 2-19 | 0.858 |
| 2-20 | 0.033 |
| 2-21 | 0.456 |
| 2-22 | 0.009 |
| 2-23 | 0.007 |
| 2-24 | 0.013 |
| 2-25 | 13.000 |
| 2-26 | 0.011 |
| 2-27 | 0.277 |
| 2-28 | 1.410 |
| 2-29 | 11.600 |
| 2-30 | 16.300 |
| 2-31 | 1.470 |
| 2-32 | 0.103 |
| 2-33 | 0.071 |
| 2-34 | 0.023 |

TABLE 10-continued

| Example | EC$_{50}$ [μM] |
|---|---|
| 2-35 | 0.026 |
| 2-36 | 44.200 |
| 2-37 | 24.300 |
| 2-38 | 0.947 |
| 2-39 | 0.018 |
| 2-40 | 0.103 |
| 2-41 | 0.360 |
| 2-42 | 1.310 |
| 2-43 | 0.062 |
| 2-44 | 0.046 |
| 2-45 | 0.025 |
| 2-46 | 0.037 |
| 2-47 | 0.138 |
| 2-48 | 0.064 |
| 2-49 | 0.094 |
| 2-50 | 1.050 |
| 2-51 | 0.077 |
| 2-52 | 1.190 |
| 2-53 | 0.021 |
| 2-54 | 0.154 |
| 2-55 | 0.007 |
| 2-56 | 9.300 |
| 2-57 | 0.009 |
| 2-58 | 7.530 |
| 2-59 | 2.220 |
| 2-60 | 0.011 |
| 2-61 | 0.015 |
| 2-62 | 0.068 |
| 2-63 | 0.005 |
| 2-64 | 0.054 |
| 2-65 | 2.380 |
| 2-66 | 0.016 |
| 2-67 | 15.000 |
| 2-68 | 0.090 |
| 2-69 | 0.029 |
| 2-70 | 3.010 |
| 2-71 | 2.500 |
| 2-72 | 0.016 |
| 2-73 | 0.159 |
| 2-74 | 0.084 |
| 2-75 | 0.095 |
| 2-76 | 0.094 |
| 2-77 | 0.044 |
| 2-78 | 0.033 |
| 2-79 | 0.064 |
| 3-01 | 0.086 |
| 3-02 | 0.141 |
| 3-03 | 0.062 |
| 3-04 | 0.138 |
| 3-05 | 3.180 |
| 3-06 | 0.978 |
| 3-07 | 0.011 |
| 3-08 | 0.558 |
| 3-09 | 0.012 |
| 3-10 | 0.018 |
| 3-11 | 0.258 |
| 3-12 | 0.281 |
| 3-13 | 0.019 |
| 3-14 | 0.081 |
| 3-15 | 29.000 |
| 3-16 | 0.019 |
| 3-17 | 0.011 |
| 3-18 | 0.045 |
| 3-19 | 0.012 |
| 3-20 | 1.050 |
| 3-21 | 1.980 |
| 4-01 | 0.064 |
| 4-02 | 0.283 |
| 4-03 | 0.097 |
| 5-01 | 0.022 |
| 5-02 | 0.190 |
| 5-03 | 0.040 |
| 5-04 | 0.169 |
| 5-05 | 0.065 |
| 5-06 | 0.032 |
| 5-07 | 0.030 |
| 5-08 | 0.072 |
| 5-09 | 0.126 |
| 5-10 | 0.028 |
| 6-01 | 0.216 |
| 7-01 | 5.590 |
| 8-01 | 0.064 |
| 8-02 | 2.690 |
| 8-03 | >100 |
| 8-04 | 0.109 |
| 8-05 | 0.242 |
| 9-01 | 0.019 |
| 9-02 | 0.069 |
| 9-03 | 0.046 |
| empty | empty |

Based on the demonstrated ability of the compounds of the invention to activate GPR119 it is predicted that said compounds are useful for treatment of diseases and/or prevention of conditions which are modulated by GPR119.

Especially, the compounds of the invention may be useful to treat GPR119-related diseases and/or prevent GPR119-mediated conditions in humans.

The compounds of the invention are especially suitable for the treatment and/or prevention of:

1a) Disorders of fatty acid metabolism and glucose utilization disorders
1b) Disorders in which insulin resistance is involved
2) Diabetes mellitus, especially type 2 diabetes mellitus, including the prevention of the sequelae associated therewith. Particular aspects in this context are:
   a) Improvement of hyperglycemia
   b) Improvement of insulin resistance
   c) Improvement of glucose tolerance
   d) Protection of pancreatic beta cells
   e) Improvement of beta cell function
   f) Prevention of micro- and macrovascular disorders, such as
      a. Retinopathy
      b. Atherosclerosis
      c. Nephropathy and microalbuminuria
      d. Neuropathy
   g) Chronic low grade inflammation
3) Various other conditions which may be associated with the metabolic syndrome or the syndrome X, such as
   a) Increased abdominal girth
   b) Obesity
   c) Liver disorders
      a. Fatty liver
      b. Steatosis
      c. Steatohepatitis
      d. Cirrhosis
   d) Dyslipidemia (e.g. hypertriglyceridemia, hypercholesterolemia, hyperlipoproteinemia and/or low HDL)
   e) Insulin resistance
   f) Hypercoagulability
   g) Hyperuricemia
   h) Thromboses, hypercoagulable and prothrombotic states (arterial and venous)
   i) High blood pressure
   j) Endothelial dysfunction
   k) Heart failure, for example (but not limited to) following myocardial infarction, hypertensive heart disease or cardiomyopathy
4) Cardiovascular diseases, for example (but not limited to) myocardial infarction and stroke 5) Bone-related diseases and disorders characterized by reduced bone mass, such as:
   a) Osteoporosis
   b) Rheumatoid arthritis
   c) Osteoarthritis.

The invention claimed is:
1. A compound of the formula I

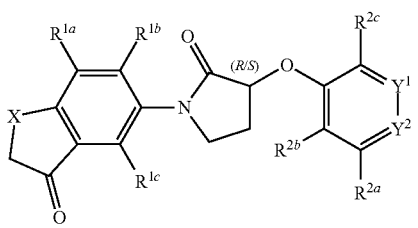

in which
X is selected from the group consisting of $CH_2$ and $CH_2$-$CH_2$;
$R^{1a}$ is selected from the group consisting of H, F, Cl, Br, $(C_1-C_6)$-alkyl and CN;
$R^{1b}$ is selected from the group consisting of H, F, Cl and $(C_1-C_6)$-alkyl;
$R^{1c}$ is selected from the group consisting of H, F, Cl and $(C_1-C_6)$-alkyl;
$R^{2a}$ is selected from the group consisting of H, F, Cl, Br, $(C_1-C_6)$-alkyl, CN, $CO_2R^5$ and $CONR^5R^{5'}$;
$R^{2b}$ is selected from the group consisting of H, F, Cl and $(C_1-C_6)$-alkyl;
$R^{2c}$ is selected from the group consisting of H, F, Cl and $(C_1-C_6)$-alkyl;
$R^5$, $R^{5'}$ are independently of each other selected from the group consisting of H and $(C_1-C_4)$-alkyl;
one of the groups $Y^1$ and $Y^2$ is N, N-oxide or $CR^{2d}$, the other is C—Z—$R^3$—$R^4$;
$R^{2d}$ is selected from the group consisting of H, F, Cl and $(C_1-C_4)$-alkyl;
Z is selected from the group consisting of a bond, O, CO, COO, S, SO and $SO_2$;
$R^3$ is selected from the group consisting of a bond and $(CR6R6')_n$;
$R^6$, $R^{6'}$ are independently of each other selected from the group consisting of H and $(C_1-C_6)$-alkyl, which is unsubstituted or monofluorinated and the overall number of carbon atoms in a $(CR^6R^{6'})_n$ group is below or equal to eight (8);
n is selected from the group consisting of 1, 2, 3, 4 and 5;
$R^4$ is selected from the group consisting of $(C_1-C_6)$-alkyl, mono-, di- or trifluorinated $(C_1-C_6)$-alkyl, $(C_2-C_6)$-alkenyl, $(C_2-C_6)$-alkynyl, $CO_2R^5$, $OR^7$, $NR^8R^{8'}$, $SR^9$, $(C_3-C_8)$-cycloalkyl, a 4- to 6-membered heterocycle, which comprises one or two identical or different ring heteroatoms selected from the group consisting of N and O, phenyl, a 5- to 6-membered heteroaryl, which comprises one, two or three identical or different ring heteroatoms selected from the group consisting of N, O and S, wherein all cyclic groups within $R^4$ are unsubstituted or substituted by one to three identical or different substituents selected from the group consisting of $(C_1-C_4)$-alkyl, $(C_1-C_4)$-alkanoyl, hydroxy-$(C_0-C_4)$-alkyl, $(C_1-C_3)$-alkoxy-$(C_0-C_4)$-alkyl, oxo (=O), F and Cl;

$R^7$ is selected from the group consisting of H, $(C_1-C_6)$-alkyl, hydroxy-$(C_1-C_4)$-alkyl and $(C_1-C_3)$-alkoxy-$(C_1-C_4)$-alkyl;
$R^8$, $R^{8'}$ are independently of each other selected from the group consisting of H and $(C_1-C_6)$-alkyl and
$R^9$ is $(C_1-C_6)$-alkyl;
in any of its stereoisomeric forms, or a mixture of stereoisomeric forms in any ratio, or a physiologically acceptable salt thereof, or a physiologically acceptable solvate of any of them.

2. The compound of claim 1, wherein
the 3-position of the pyrrolidinone ring has (R)-configuration.

3. The compound of claim 1, wherein
X is $CH_2$.

4. The compound of claim 1, wherein
$R^{1a}$ is selected from the group consisting of H, F, Cl, methyl and CN;
$R^{1b}$ is H and
$R^{1c}$ is selected from the group consisting of H, F and methyl.

5. The compound of claim 1, wherein
$R^{2a}$ is selected from the group consisting of H, F, Cl, methyl and CN;
$R^{2b}$ is H and
$R^{2c}$ is H.

6. The compound of claim 1, which is a compound of the formula Ia

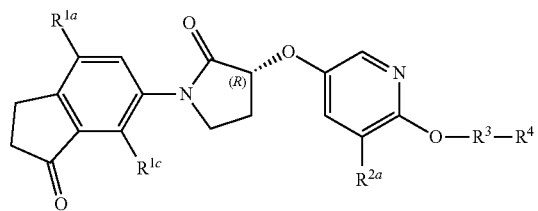

wherein
$R^{1a}$ is selected from the group consisting of H, F, Cl, $(C_1-C_4)$-alkyl and CN;
$R^{1c}$ is selected from the group consisting of H, F and $(C_1-C_4)$-alkyl;
$R^{2a}$ is selected from the group consisting of H, F, Cl, $(C_1-C_4)$-alkyl and CN;
$R^3$ is selected from the group consisting of a bond and $(CR^6R^{6'})_n$;
n is selected from the group consisting of 1, 2 and 3;
$R^6$, $R^{6'}$ are independently of each other H or $(C_1-C_2)$-alkyl, and the overall number of carbon atoms in a $(CR^6R^{6'})_n$ group is below or equal to eight (8) and
$R^4$ is selected from the group consisting of $(C_1-C_6)$-alkyl, mono-, di- or trifluorinated $(C_1-C_6)$-alkyl, $O(C_1-C_4)$-alkyl, $(C_3-C_8)$-cycloalkyl, a 4- to 6-membered heterocycle, which comprises one or two ring oxygen atoms, wherein all cyclic groups within $R^4$ are unsubstituted or substituted by $(C_1-C_4)$-alkyl.

7. The compound of claim 1, wherein
X is selected from the group consisting of $CH_2$ and $CH_2$-$CH_2$;
$R^{1a}$ is selected from the group consisting of H, F, Cl, Br, $(C_1-C_4)$-alkyl and CN;

$R^{1b}$ is H;

$R^{1c}$ is selected from the group consisting of H, F and methyl;

$R^{2a}$ is selected from the group consisting of H, F and $(C_1-C_4)$-alkyl;

$R^{2b}$ is H;

$R^{2c}$ is H;

one of the groups $Y^1$ and $Y^2$ is N, N-oxide or $CR^{2d}$, the other is C—Z—$R^3$—$R^4$;

$R^{2d}$ is H;

Z is selected from the group consisting of a bond, O, CO, COO, S and SO;

$R^3$ is selected from the group consisting of a bond and $(CR^6R^{6'})_n$ n is selected from the group consisting of 1, 2, 3, 4 and 5;

$R^6$, $R^{6'}$ are independently of each other selected from the group consisting of H, methyl, ethyl and 2-fluoro-ethyl, and the overall number of carbon atoms in a $(CR^6R^{6'})_n$ group is below or equal to eight (8);

$R^4$ is selected from the group consisting of $(C_1-C_6)$-alkyl, mono-, di- or trifluorinated $(C_1-C_6)$-alkyl, $(C_4-C_6)$-alkenyl, $CO_2R^5$, $OR^7$, $NR^8R^{8'}$, $SR^9$, $(C_3-C_6)$-cycloalkyl, a 4- to 6-membered heterocycle, which comprises one or two oxygen atoms or one nitrogen atom, phenyl, a 5- to 6-membered heteroaryl, which comprises one or two nitrogen atoms, one nitrogen and one oxygen atom, one nitrogen and one sulfur atom or two nitrogen atoms and one oxygen atom, wherein all cyclic groups within $R^4$ are unsubstituted or mono-substituted by substituents selected from the group consisting of F, $(C_1-C_4)$-alkyl, hydroxymethyl, acetyl, hydroxyl and oxo (═O);

$R^5$ is $(C_1-C_4)$-alkyl;

$R^7$ is selected from the group consisting of H, methyl, ethyl and hydroxy-ethyl;

$R^8$, $R^{8'}$ are independently of each other $(C_1-C_4)$-alkyl and $R^9$ is methyl.

8. The compound of claim 6, wherein $R^{1a}$ is selected from the group consisting of H, F, Cl, Br, $(C_1-C_4)$-alkyl and CN;

$R^{1c}$ is selected from the group consisting of H, F and methyl;

$R^{2a}$ is selected from the group consisting of H, F and $(C_1-C_4)$-alkyl;

$R^3$ is selected from the group consisting of a bond and $(CR^6R^{6'})_n$;

n is selected from the group consisting of 1, 2, 3, 4 and 5;

$R^6$, $R^{6'}$ are independently of each other selected from the group consisting of H, methyl, ethyl and 2-fluoro-ethyl, and the overall number of carbon atoms in a $(CR^6R^{6'})_n$ group is below or equal to eight (8);

$R^4$ is selected from the group consisting of $(C_1-C_6)$-alkyl, mono-, di- or trifluorinated $(C_1-C_6)$-alkyl, $(C_4-C_6)$-alkenyl, $CO_2R^5$, $OR^7$, $NR^8R^{8'}$, $SR^9$, $(C_3-C_6)$-cycloalkyl, a 4- to 6-membered heterocycle, which comprises one or two oxygen atoms or one nitrogen atom, phenyl, a 5- to 6-membered heteroaryl, which comprises one or two nitrogen atoms, one nitrogen and one oxygen atom, one nitrogen and one sulfur atom or two nitrogen atoms and one oxygen atom, wherein all cyclic groups within $R^4$ are unsubstituted or mono-substituted by substituents selected from the group consisting of F, $(C_1-C_4)$-alkyl, hydroxymethyl, acetyl, hydroxyl and oxo (═O);

$R^5$ is $(C_1-C_4)$-alkyl;

$R^7$ is selected from the group consisting of H, methyl, ethyl and hydroxy-ethyl;

$R^8$, $R^{8'}$ are independently of each other $(C_1-C_4)$-alkyl and $R^9$ is methyl.

9. A compound selected from the group consiting of (R)-3-[4-(2-Cyclopropyl-ethoxy)-phenoxy]-1-(7-fluoro-3-oxo-indan-5-yl)-pyrrolidin-2-one, (R)-3-(6-Cyclopropylmethoxy-pyridin-3-yloxy)-1-(7-fluoro-3-oxo-indan-5-yl)-pyrrolidin-2-one, (R)-1-(7-Fluoro-3-oxo-indan-5-yl)-3-[6-(tetrahydro-pyran-4-yloxy)-pyridin-3-yloxy]-pyrrolidin-2-one, (R)-3-(6-Ethoxy-pyridin-3-yloxy)-1-(7-fluoro-3-oxo-indan-5-yl)-pyrrolidin-2-one, (R)-1-(7-Fluoro-3-oxo-indan-5-yl)-3-(6-isopropoxy-pyridin-3-yloxy)-pyrrolidin-2-one and (R)-3-(6-Cyclopropoxy-pyridin-3-yloxy)-1-(7-fluoro-3-oxo-indan-5-yl)-pyrrolidin-2-one;

or a pharmaceutically acceptable salt thereof.

10. A pharmaceutical composition comprising at least one compound as claimed in claim 1 or a physiologically acceptable salt thereof.

11. The pharmaceutical composition as claimed in claim 10, comprising additionally one or more active ingredients selected from the group of:

Insulin and insulin derivatives, GLP-1, GLP-1 analogues and GLP-1 receptor agonists, polymer bound GLP-1 and GLP-1 analogues, dual GLP-1/GIP agonists, dual GLP-1/glucagon receptor agonists, PYY3-36 or analogues thereof, pancreatic polypeptide or analogues thereof, glucagon receptor agonists or antagonists, GIP receptor agonists or antagonists, ghrelin antagonists or inverse agonists, xenin and analogues thereof, DDP-IV inhibitors, SGLT-2 inhibitors, dual SGLT-2/SGLT-1 inhibitors, biguanides, thiazolidinediones, PPAR agonists, PPAR modulators, sulfonylureas, meglitinides, alpha-glucosidase inhibitors, amylin and amylin analogues, GPR119 agonists, GPR40 agonists, GPR120 agonists, GPR142 agonists, TGR5 agonists, AMPK stimulants, AMPK activators, inhibitors of 11-beta-HSD, activators of glucokinase, inhibitors of DGAT, inhibitors of protein tyrosine phosphatase 1, inhibitors of glucose-6-phosphatase, inhibitors of fructose-1,6-bisphosphatase, inhibitors of glycogen phosphorylase, inhibitors of phosphoenol pyruvate carboxykinase, inhibitors of glycogen synthase kinase, inhibitors of pyruvate dehydrogenase kinase, alpha2 adrenergic receptor antagonists, CCR-2 antagonists, modulators of glucose transporter-4, somatostatin receptor 3 agonists, HMG-CoA-reductase inhibitors, fibrates, nicotinic acid and derivatives thereof, nicotinic acid receptor 1 agonists, ACAT inhibitors, cholesterol absorption inhibitors, bile acid-binding substances, IBAT inhibitors, MTP inhibitors, modulators of PCSK9, LDL receptor up-regulators (liver selective thyroid hormone receptor beta agonists), HDL-raising compounds, lipid metabolism modulators, PLA2 inhibitors, ApoA-I enhancers, cholesterol synthesis inhibitors, omega-3 fatty acids and derivatives thereof, active substances for the treatment of obesity, CB1 receptor antagonists, MCH-1 antagonists, MC4 receptor agonists and partial agonists, NPY5 or NPY2 antagonists, NPY4 agonists, beta-3 adrenergic receptor agonists, leptin or leptin mimetics, 5HT2c receptor agonists, lipase inhibitors, angiogenesis inhibitors, H3 antagonists, AgRP inhibitors, triple monoamine uptake inhibitors, MetAP2 inhibitors, antisense oligonucleotides against production of fibroblast growth factor receptor 4 or prohibitin targeting peptide-1, drugs for influencing high blood pressure, chronic heart failure or atherosclerosis, angiotensin II receptor antagonists, ACE inhibitors, ECE inhibitors, diuretics, beta-blockers, calcium antagonists, centrally acting antihypertensives, antagonists of the alpha-2 adrenergic receptor, inhibitors of neutral endopeptidase and thrombocyte aggregation inhibitors, drugs for influencing high blood pressure, chronic heart failure or atherosclerosis, nitric oxide donors, angiotensin II receptor antagonists, dual ARB agonists, ACE inhibitors, ACE-2 activators, AT1 antagonists, AT2 receptor agonists, renin inhibitors, prorenin inhibitors, ECE inhibitors, endothelin receptor blockers, endothelin antagonists, diuretics, aldosterone antagonists, aldosterone synthase inhibitors, alpha-blockers, antagonists of the alpha-2 adrenergic receptor, beta-blockers, mixed alpha-/beta-blockers, calcium antagonists/calcium channel blockers, nasal formulations of calcium channel blockers, dual mineralocorticoid/CCBs, centrally acting antihypertensives, antagonists of the alpha-2 adrenergic receptor, inhibitors of neutral endopeptidase, aminopeptidase-A inhibitors, vasopeptide inhibitors, dual vasopeptide inhibitors, neprilysin-ACE inhibitors, neprilysin-ECE inhibitors, dual-acting AT receptor-neprilysin inhibitors, dual AT1/ETA antagonists, advanced glycation end-product breakers, recombinant renalase, blood pressure vaccines, anti-RAAS vaccines, AT1- or AT2-vaccines, modulators of genetic polymorphisms with antihypertensive response and thrombocyte aggregation inhibitors.

12. The pharmaceutical composition as claimed in claim 10, comprising additionally one or more active ingredients selected from the group of:

Insulin and insulin derivatives, GLP-1, GLP-1 analogues and GLP-1 receptor agonists, polymer bound GLP-1 and GLP-1 analogues, dual GLP-1/GIP agonists, dual GLP-1/ glucagon receptor agonists, PYY3-36 or analogues thereof, pancreatic polypeptide or analogues thereof, glucagon receptor agonists or antagonists, GIP receptor agonists or antagonists, ghrelin antagonists or inverse agonists, xenin and analogues thereof, DDP-IV inhibitors, SGLT-2 inhibitors, dual SGLT-2/SGLT-1 inhibitors, biguanides, thiazolidinediones, dual PPAR agonists, sulfonylureas, meglitinides, alpha-glucosidase inhibitors, amylin and amylin analogues, GPR119 agonists, GPR40 agonists, GPR120 agonists, GPR142 agonists, systemic or low-absorbable TGR5 agonists, Cycloset, inhibitors of 11-beta-HSD, activators of glucokinase, inhibitors of DGAT, inhibitors of protein tyrosinephosphatase 1, inhibitors of glucose-6-phosphatase, inhibitors of fructose-1,6-bisphosphatase, inhibitors of glycogen phosphorylase, inhibitors of phosphoenol pyruvate carboxykinase, inhibitors of glycogen synthase kinase, inhibitors of pyruvate dehydrogenase kinase, alpha2 adrenergic receptor antagonists, CCR-2 antagonists, modulators of glucose transporter-4, somatostatin receptor 3 agonists, HMG-CoA-reductase inhibitors, fibrates, nicotinic acid and derivatives thereof, nicotinic acid receptor 1 agonists, PPAR (-alpha, -gamma or -alpha/gamma) agonists or modulators, PPAR-delta agonists, ACAT inhibitors, cholesterol absorption inhibitors, bile acid-binding substances, IBAT inhibitors, MTP inhibitors, modulators of PCSK9, LDL receptor up-regulators (liver selective thyroid hormone receptor beta agonists), HDL-raising compounds, lipid metabolism modulators, PLA2 inhibitors, ApoA-I enhancers, cholesterol synthesis inhibitors, omega-3 fatty acids and derivatives thereof, active substances for the treatment of obesity, such as sibutramine, tesofensine, orlistat, CB1 receptor antagonists, MCH-1 antagonists, MC4 receptor agonists and partial agonists, NPY5 or NPY2 antagonists, NPY4 agonists, beta-3 adrenergic receptor agonists, leptin or leptin mimetics, 5HT2c receptor agonists, or the combinations of bupropione/naltrexone (Contrave), bupropione/zonisamide (Empatic), bupropione/phentermine or pramlintide/metreleptin, phentermine/topiramate (Qsymia), lipase inhibitors, angiogenesis inhibitors, H3 antagonists, AgRP inhibitors, triple monoamine uptake inhibitors, MetAP2 inhibitors, nasal formulations of the calcium channel blocker diltiazem, antisense oligonucleotides against production of fibroblast growth factor receptor 4 or prohibitin targeting peptide-1, drugs for influencing high blood pressure, chronic heart failure or atherosclerosis, such as angiotensin II receptor antagonists, ACE inhibitors, ECE inhibitors, diuretics, beta-blockers, calcium antagonists, centrally acting antihypertensives, antagonists of the alpha-2 adrenergic receptor, inhibitors of neutral endopeptidase and thrombocyte aggregation inhibitors.

13. The pharmaceutical composition as claimed in claim 10, comprising additionally metformin.

14. The pharmaceutical composition as claimed in claim 10, comprising additionally at least one DPP-IV inhibitor.

15. The pharmaceutical composition as claimed in claim 14, wherein the DPP-IV inhibitor is selected from the group consisting of alogliptin, linagliptin, saxagliptin, sitagliptin, anagliptin, teneligliptin, trelagliptin, vildagliptin, gemigliptin, omarigliptin, evogliptin and dutogliptin.

16. The pharmaceutical composition as claimed in claim 10, comprising additionally at least one SGLT-2 inhibitor.

17. The pharmaceutical composition as claimed in claim 16, wherein the SGLT-2 inhibitor is selected from the group consisting of canagliflozin, dapagliflozin, remogliflozin, remogliflozin etabonate, sergliflozin, empagliflozin, ipragliflozin, tofogliflozin, luseogliflozin and ertugliflozin.

18. The pharmaceutical composition as claimed in claim 10, comprising additionally at least one GPR40 agonist.

19. The pharmaceutical composition as claimed in claim 18, wherein the GPR40 agonist is selected from the group consisting of fasiglifam (TAK-875), TUG-424, P-1736, P-11187, JTT-851, GW9508, CNX-011-67, AM-1638 and AM-5262.

20. The pharmaceutical composition as claimed in claim 10, comprising additionally ezetimibe.

21. The pharmaceutical composition as claimed in claim 10, comprising additionally at least one HMG-CoA reductase inhibitor.

22. The pharmaceutical composition as claimed in claim 21, wherein the HMG-CoA reductase inhibitor is selected from the group consisting of simvastatin, atorvastatin, rosuvastatin, pravastatin, fluvastatin, pitavastatin, lovastatin, mevastatin, rivastatin and cerivastatin.

23. The pharmaceutical composition as claimed in claim 10, comprising additionally at least one PPAR agonist or PPAR modulator.

24. The pharmaceutical composition as claimed in claim 23, in wherein the PPAR agonist or PPAR modulator is selected from the group consisting of aleglitazar, muraglitazar, tesaglitazar and saroglitazar.

25. The pharmaceutical composition as claimed in claim 23, in wherein the PPAR agonist or PPAR modulator is selected from the group consisting of pioglitazone, rivoglitazone, rosiglitazone, troglitazone and lobeglitazone.

26. The pharmaceutical composition as claimed in claim 10, comprising additionally acarbose.

27. A method for treating type 2 diabetes, obesity or dyslipidemia in a patient in need thereof comprising adminstering to said patient a therapeutically effective amount of the compound claim 1.

28. A method for treating type 2 diabetes, obesity or dyslipidemia in a patient in need thereof comprising administering to said patient a therapeutically effective amount of the pharmaceutical composition of claim 10.

29. A method for treating type 2 diabetes, obesity or dyslipidemia in a patient, the method comprising administering to the patient an effective amount of at least one compound of claim 1 and an effective amount of at least one other compound useful for treating type 2 diabetes, obesity or dyslipidemia.

30. The method as claimed in claim 29 wherein the effective amount of said compounds are adminstered to the patient simultaneously.

31. The method as claimed in claim 29 wherein the effective amount of said compounds are adminstered to the patient sequentially.

* * * * *